(12) United States Patent
Kim et al.

(10) Patent No.: US 11,618,897 B2
(45) Date of Patent: Apr. 4, 2023

(54) METHODS, COMPOSITIONS, AND SYSTEMS FOR CAPTURING PROBES AND/OR BARCODES

(71) Applicant: 10x Genomics, Inc., Pleasanton, CA (US)

(72) Inventors: Hanyoup Kim, Pleasanton, CA (US); David Sukovich, Pleasanton, CA (US); Layla Katiraee, Pleasanton, CA (US); Augusto Manuel Tentori, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/871,525

(22) Filed: Jul. 22, 2022

(65) Prior Publication Data

US 2022/0356464 A1 Nov. 10, 2022

Related U.S. Application Data

(63) Continuation of application No. PCT/US2021/061401, filed on Dec. 1, 2021.

(60) Provisional application No. 63/252,323, filed on Oct. 5, 2021, provisional application No. 63/148,825, filed on Feb. 12, 2021, provisional application No. 63/128,796, filed on Dec. 21, 2020.

(51) Int. Cl.
*C12Q 1/6837* (2018.01)
*C12N 15/10* (2006.01)

(52) U.S. Cl.
CPC .................. *C12N 15/1065* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Homes |
| 5,512,462 A | 4/1996 | Cheng |
| 5,559,032 A | 9/1996 | Porneroy |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,716,825 A | 2/1998 | Hancock et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,958,775 A | 9/1999 | Wicksttrom |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,083,761 A | 7/2000 | Kedar et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |

(Continued)

FOREIGN PATENT DOCUMENTS

| | | |
|---|---|---|
| CA | 3054046 | 3/2020 |
| CN | 1680604 | 10/2005 |

(Continued)

OTHER PUBLICATIONS

Arslan et al., "Engineering of a superhelicase through conformational control (Supplementary Materials)," Science, Apr. 17, 2015, 348(6232):344-347, 18 pages.

(Continued)

*Primary Examiner* — Christopher M Gross
(74) *Attorney, Agent, or Firm* — Fish & Richardson P.C.

(57) ABSTRACT

Provided herein are methods for capturing a connected probe and/or a capture handle sequence to a capture domain of a capture probe.

30 Claims, 60 Drawing Sheets

(56) References Cited

U.S. PATENT DOCUMENTS

| | | |
|---|---|---|
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,544,790 B1 | 4/2003 | Sabatini |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,673,620 B1 | 1/2004 | Loeffler |
| 6,699,710 B1 | 3/2004 | Kononen |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,098,041 B2 | 8/2006 | Kaylor et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,700,286 B2 | 4/2010 | Stroun et al. |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,207,093 B2 | 6/2012 | Szostak |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,951,781 B2 | 2/2015 | Reed |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,557,330 B2 | 1/2017 | Siciliano et al. |
| 9,574,230 B2 | 2/2017 | Van Eijk |
| 9,582,877 B2 | 2/2017 | Fu |

(56) References Cited

U.S. PATENT DOCUMENTS

| | | |
|---|---|---|
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,273,541 B2 | 4/2019 | Hindson et al. |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 2001/0055764 A1 | 12/2001 | Empedocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0150909 A1 | 10/2002 | Stuelpnagel |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0040035 A1 | 2/2003 | Slamon |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0175844 A1 | 9/2003 | Nadler et al. |
| 2003/0215936 A1 | 11/2003 | Kallioniemi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0112442 A1 | 6/2004 | Maerkl |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0100900 A1 | 5/2005 | Kawashima et al. |
| 2005/0116161 A1 | 6/2005 | Hafeman et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0179746 A1 | 8/2005 | Roux et al. |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0164490 A1 | 7/2006 | Kim et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |

(56) References Cited

U.S. PATENT DOCUMENTS

| | | |
|---|---|---|
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0116612 A1 | 5/2007 | Williamson |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0145616 A1 | 6/2008 | Gharib et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2009/0321262 A1 | 12/2009 | Adachi et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120043 A1 | 5/2010 | Sood et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2010/0282617 A1 | 11/2010 | Rothberg et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0177518 A1 | 7/2011 | Kartalov et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0035239 A1 | 2/2013 | Kong et al. |
| 2013/0052331 A1 | 2/2013 | Kram et al. |
| 2013/0065768 A1 | 3/2013 | Zheng et al. |
| 2013/0079232 A1 | 3/2013 | Kain et al. |
| 2013/0096033 A1 | 4/2013 | Routenberg |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0274731 A1 | 9/2014 | Raymond et al. |
| 2014/0323330 A1 | 10/2014 | Glezer et al. |
| 2014/0342921 A1 | 11/2014 | Weiner |
| 2015/0000854 A1 | 1/2015 | Gann-Fetter et al. |
| 2015/0148239 A1 | 5/2015 | Jon |
| 2015/0219618 A1 | 8/2015 | Krishnan et al. |
| 2015/0292988 A1 | 10/2015 | Bharadwaj et al. |
| 2016/0019337 A1 | 1/2016 | Roberts et al. |
| 2016/0024576 A1 | 1/2016 | Chee |
| 2016/0033496 A1 | 2/2016 | Chou et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0299165 A1 | 10/2016 | Zhou |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0166962 A1 | 6/2017 | Van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0275669 A1 | 9/2017 | Weissleder et al. |
| 2017/0283860 A1 | 10/2017 | Kool et al. |
| 2017/0335297 A1 | 11/2017 | Ha et al. |
| 2017/0335410 A1 | 11/2017 | Driscoll et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0094316 A1 | 4/2018 | Oliphant et al. |
| 2018/0095067 A1 | 4/2018 | Huff et al. |
| 2018/0104694 A1 | 4/2018 | Huff et al. |
| 2018/0104964 A1 | 4/2018 | Uemura et al. |
| 2018/0112261 A1 | 4/2018 | Van Driel et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0217094 A1 | 8/2018 | Herr et al. |
| 2018/0237864 A1 | 8/2018 | Imler et al. |
| 2018/0245142 A1 | 8/2018 | So et al. |
| 2018/0247017 A1 | 8/2018 | van Eijk et al. |

(56) References Cited

U.S. PATENT DOCUMENTS

| | | |
|---|---|---|
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2019/0032128 A1 | 1/2019 | Chen et al. |
| 2019/0055594 A1 | 2/2019 | Samusik et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249248 A1 | 8/2019 | Beechem et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0352708 A1 | 11/2019 | Gaige et al. |
| 2019/0360043 A1 | 11/2019 | Pham et al. |
| 2019/0367969 A1 | 12/2019 | Belhocine et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0199565 A1 | 6/2020 | Chen et al. |
| 2020/0199572 A1 | 6/2020 | Kuersten et al. |
| 2020/0002242 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0363408 A1 | 11/2020 | Chou et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333192 A1 | 10/2022 | Uytingco |

(56) References Cited

U.S. PATENT DOCUMENTS

| | | |
|---|---|---|
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0364163 A1 | 11/2022 | Stahl et al. |
| 2022/0389491 A1 | 12/2022 | Chee |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |

FOREIGN PATENT DOCUMENTS

| | | |
|---|---|---|
| CN | 1981188 | 6/2007 |
| CN | 101221182 | 7/2008 |
| CN | 108949924 | 12/2018 |
| EP | 0961110 | 12/1999 |
| EP | 0901631 | 8/2004 |
| EP | 1712623 | 10/2006 |
| EP | 1782737 | 5/2007 |
| EP | 1878502 | 1/2008 |
| EP | 1910562 | 4/2008 |
| EP | 1923471 | 5/2008 |
| EP | 1929039 | 6/2008 |
| EP | 2002017 | 12/2008 |
| EP | 2292788 | 3/2011 |
| EP | 2302070 | 3/2011 |
| EP | 2580351 | 4/2013 |
| EP | 2881465 | 6/2015 |
| EP | 3013983 | 5/2016 |
| EP | 3013984 | 5/2016 |
| EP | 2350648 | 7/2017 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/17390 | 3/2000 |
| WO | WO 2000/063437 | 10/2000 |
| WO | WO 2001/06012 | 1/2001 |
| WO | WO 2001/009363 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/056861 | 6/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/093098 | 8/2008 |
| WO | WO 2008/157801 | 12/2008 |
| WO | WO 2009/032167 | 3/2009 |
| WO | WO 2009/036525 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/102903 | 8/2011 |
| WO | WO 2011/127006 | 12/2011 |
| WO | WO 2011/155833 | 12/2011 |
| WO | WO 2012/049316 | 4/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/130576 | 8/2014 |
| WO | WO 2014/142841 | 9/2014 |
| WO | WO 2014/144713 | 9/2014 |
| WO | WO 2014/152397 | 9/2014 |
| WO | WO 2014/210223 | 12/2014 |
| WO | WO 2014/210225 | 12/2014 |
| WO | WO 2015/069374 | 5/2015 |
| WO | WO 2015/161173 | 10/2015 |
| WO | WO 2016/077763 | 5/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/027367 | 2/2017 |
| WO | WO 2017/048871 | 3/2017 |
| WO | WO 2017/075293 | 5/2017 |
| WO | WO 2017/112957 | 6/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/091676 | 5/2018 |
| WO | WO 2018/136856 | 7/2018 |
| WO | WO 2018/144582 | 8/2018 |
| WO | WO 2018/148471 | 8/2018 |
| WO | WO 2018/209398 | 11/2018 |
| WO | WO 2019/012005 | 1/2019 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/140334 | 7/2019 |
| WO | WO 2019/165318 | 8/2019 |
| WO | WO 2019/213254 | 11/2019 |
| WO | WO 2019/213294 | 11/2019 |
| WO | WO 2020/028194 | 2/2020 |

(56) References Cited

FOREIGN PATENT DOCUMENTS

| | | |
|---|---|---|
| WO | WO 2020/047002 | 3/2020 |
| WO | WO 2020/047004 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/176788 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/240025 | 12/2020 |
| WO | WO 2020/243579 | 12/2020 |
| WO | WO 2020/254519 | 12/2020 |
| WO | WO 2021/016379 | 1/2021 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/119320 | 6/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2.022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/098810 | 5/2022 |
| WO | WO 2022/099037 | 5/2022 |
| WO | WO 2022/109181 | 5/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/256503 | 12/2022 |

OTHER PUBLICATIONS

Arslan et al., "Engineering of a superhelicase through conformational control," Science, Apr. 17, 2015, 348(6232):344-347.

Gao et al., "A highly homogeneous expansion microscopy polymer composed of tetrahedron-like monomers," bioRxiv, Oct. 22, 2019, 23 pages (Preprint).

Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.

U.S. Appl. No. 16/353,937, filed Mar. 14, 2019, Frisen et al.

U.S. Appl. No. 16/876,709, filed May 18, 2020, Schnall-Levin et al.

U.S. Appl. No. 17/707,189, filed Mar. 29, 2022, Chell et al.

U.S. Appl. No. 60/416,118, filed Oct. 3, 2002, Fan et al.

U.S. Appl. No. 61/267,363, filed Dec. 7, 2009, Fan et al.

U.S. Appl. No. 61/839,313, filed Jun. 25, 2013, Chee et al.

U.S. Appl. No. 61/839,320, filed Jun. 25, 2013, Chee et al.

U.S. Appl. No. 61/902,105, filed Nov. 8, 2013, Kozlov et al.

[No. Author Listed], "Chromium Next GEM Single Cell 3' Reagent Kits v3.1—User Guide," 10x Genomics, Document No. CG000204, Nov. 2019, 58 pages.

[No. Author Listed], "Chromium Next GEM Single Cell 3' Reagent Kits v3.1 (Dual Index)—User Guide," 10x Genomics, Mar. 2021, Document No. CG000315, 61 pages.

[No. Author Listed], "HuSNP Mapping Assay User's Manual," Affymetrix Part No. 90094 (Affymetrix, Santa Clara, Calif.), GeneChip, 2000, 104 pages.

[No. Author Listed], "Microarray technologies have excellent possibilities in genomics-related researches," Science Tools From Amersham Pharmacia Biotech, 1998, 3(4): 8 pages (with English Translation).

[No. Author Listed], "Proseek® Multiplex 96x96 User Manual," Olink Proteomics, Olink Bioscience, Uppsala, Sweden, 2017, 20 pages.

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwdl9It/e54d99fb08a8f1500aba503005a04a56/CG000238_VisiumSpatialTissueOptimizationUserGuide_RevD.pdf>, 42 pages.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwdl9It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 69 pages.

10xGenomics.com, [online], "Visimn Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.

Adessi el al., "Solid phase DNA amplification: characterisation of primer attachment and amplification mechanisms," Nucl. Acids Res., 2000, 28(20):E87, 8 pages.

(56) References Cited

OTHER PUBLICATIONS

Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgul33_datasheet.pdf, retrieved on Feb. 26, 2003, 2 pages.
Affymetrix, "Human Genome U95 Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amidzadeh et al., "Assessment of different penneabilization methods of minimizing damage to the adherent cells for detection of intracellular RNA by flow cytometry," Avicenna J Med Biotechnol., Jan. 2014, 6(1):38-46.
Andresen el al., "Helicase-dependent amplification: use in OnChip amplification and potential for point-of-care diagnostics," Expert Rev Mol Diagn., Oct. 2009, 9(7):645-650.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Asp et al., "Spatially Resolved Transcriptomes—Next Generation Tools for Tissue Exploration," Bioessays, Oct. 2020, 42(10):e1900221, 16 pages.
Assets.ctassets.net [online], "Technical Note—Visium Spatial Gene Expression Imaging Guidelines," CG000241 Rev A, 2019, retrieved on Jul. 29, 2022, retrieved from URL <https://assets.ctfassets.net/an68im79xiti/76JHgFQo6aLq8UPvfL0u2c/fc39e46f86bf75676d3f7dadc721fad/CG000241_VisiumImaging-GuidelinesTN_Rev_A.pdf>, 8 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Inunuo-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.

Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "Scalable in situ single-cell profiling by electrophoretic capture of mRNA," bioRxiv, Jan. 2022, 32 pages.
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech, 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzvme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Caliari et al., "A practical guide to hydrogels for cell culture," Nat Methods., Apr. 2016, 13(5):405-14.
Cardona et al., "TrakEM2 0.9a User Manual," Sep. 8, 2011, retrieved on Jul. 29, 2022, retreieved from URL <https://www.ini.uzh.ch/~acardona/trakem2_manual.html>, 38 pages.
Carter et al. "Stabilization of an optical microscope to 0.1 nm in three dimensions," Applied Optics, 2007, 46:421-427.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.

(56) References Cited

OTHER PUBLICATIONS

Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen ei al.. "Spatially resolved, highly multiplexed RNA profiling in single cells," Science, 2015, 348(6233):aaa6090, 21 pages.
Chen et al., "µCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-fiee DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Damianis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase,"J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.

Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the tanscriptome with RNA SPOTs," Nat Methods., 2017, 14(12):1153-1155.
Evers et al., "The effect of formaldehyde fixation on RNA: optimization of formaldehyde adduct removal," J Mol Diagn., May 2011, 13(3):282-8.
Fahy et al., "Design and synthesis of polyacrylamide-based oligonucleotide supports for use in nucleic acid diagnostics," Nucleic Acids Res., Apr. 1993, 21(8):1819-26.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Fredriksson et al., "Protein detection using proximity-dependent DNA ligation assays," Nature Biotech., 20: 473-77, 2002.
Frese et al., "Formylglycine aldehyde Tag-protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gill et al., "Nucleic acid isothermal amplification technologies: a review," Nucleosides Nucleotides Nucleic Acids, Mar. 2008, 27(3):224-43.
Github.com [online], "ST Spot Detector Usage Guide: A Guide to Using the Spatial Transcriptomics Spot Detector 2.0," Jun. 2018,

(56) References Cited

OTHER PUBLICATIONS retrieved on Jul. 29, 2022, retrieved from URL <https://github.com/SpatialTranscriptomicsResearch/st_spot_detector/wiki/ST-Spot-Detector-Usage-Guide, 6 pages.
Glass et al., "SIMPLE: a sequential immunoperoxidase labeling and erasing method," J. Histochem. Cytochem., Oct. 2009, 57(10):899-905.
Gloor, "Gene targeting in Drosophila," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount Arabidopsis samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hua et al., "Multi-level transcriptome sequencing identifies COL1A1 as a candidate marker in human heart failure progression," BMC Med., Jan. 2020, 18(1):2, 16 pages.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Penneabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of Mycobacterium avium: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.

(56) References Cited

OTHER PUBLICATIONS

Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmacogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Lamture el al., "Direct detection of nucleic acid hybridization on the surface of a charge coupled device," Nucleic Acid Res., Jun. 1994, 22(11):2121-5.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Leriche et al.. "Cleavable linkers in chemical biology," Bioorganic & Medicinal Chemistry, 2012, 20:571-582.
Li et al.. "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.

Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt el al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
MacBeath et al.. "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Maniatis et al., "Spatiotemporal Dynamics of Molecular Pathology in Amyotrophic Lateral Sclerosis", 54 pages, 2018.
Marx, "Method of the Year: spatially resolved transcriptomics," Nature Methods, 2021, 18(1):9-14.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.

(56) References Cited

OTHER PUBLICATIONS

Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3 A," Gene, 1982, 20(3):317-322.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Nadji et al., "Immunohistochemistiy of tissue prepared by a molecular-friendly fixation and processing system," Appl Immunohistochem Mol Morphol., Sep. 2005, 13(3):277-82.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Navarro et al., "ST viewer: a tool for analysis and visualization of spatial transcriptomics datasets: Supplementary Information," Bioinformatics, Mar. 2019, 1058-1060.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Olivier, "The Invader assay for SNP genotyping," Mutat. Res., Jun. 2005, 573(1-2):103-110.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger micro wells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
PCT International Search Report and Written Opinion in International Appln. No. PCT/US2021/061401, dated Mar. 4, 2022, 16 pages.

Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tc1/mariner transposon family," Curr Top Microbiol Immunol., 1996, 204:125-43.
Plongthongkum et al., "Advances in the profiling of DNA modifications: cvtosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470

(56) References Cited

OTHER PUBLICATIONS

Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, April 2010, 107(16):7407-12.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Sutherland et al., "Utility of formaldehyde cross-linking and mass spectrometry in the study of protein-protein interactions," J. Mass Spectrom., Jun. 2008, 43(6):699-715.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.

Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 2(8): 1071-8.
Trejo et al., "Extraction-free whole transcriptome gene expression analysis of FFPE sections and histology-directed subareas of tissue," Plos One, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalizationbv hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic el al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004. 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang et al., "High-fidelity mRNA amplification for gene profiling," Nature Biotechnology, Apr. 2000, 18(4):457-459.

(56) References Cited

OTHER PUBLICATIONS

Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilbrey-Clark et al., "Cell Atlas technologies and insights into tissue architecture," Biochemical Journal, Apr. 2020, 477(8):1427-1442.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Wong et al., "ST Spot Detector: a web-based application for automatic spot and tissue detection for spatial Transcriptomics image datasets," Bioinformatics, Jan. 2018, 34(11):1966-1968.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al. "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probest," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors", Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Mulder et al., "CapTCR-seq: hybrid capture for T-cell receptor repertoire profiling," Blood Advances, Dec. 2018, 2(23):3506-3514.
U.S. Appl. No. 63/033,348, filed Jun. 2, 2020, Bent.
Baner et al., "Signal amplification of padlock probes by rolling circle replication," Nucleic Acids Res., 1998, 26(22):5073-5078.
Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).
Chen et al., "Efficient in situ barcode sequencing using padlock probe-based BaristaSeq," Nucleic Acids Res., 2018, 46(4): e22, 11 pages.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Codeluppi et al., "Spatial organization of the somatosensory cortex revealed by osmFISH," Nature Methods, Nov. 2018, 15:932-935.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Faruqi et al., "High-throughput genotyping of single nucleotide polymorphisms with rolling circle amplification," BMC Genomics, Aug. 2001, 2:4, 10 pages.
Gamper et al., "Gene expression profile of bladder tissue of patients with ulcerative interstitial cystitis," BMC Genomics, Apr. 28, 2009, 10(199): 1-17.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Goh et al., "Highly Specific Multiplexed RNA Imaging in Tissues With Split-FISH," Nat Methods, Jun. 15, 2020, 17(7):689-693, 21 pages.
Goransson et al., "A single molecule array for digital targeted molecular analyses," Nucleic Acids Res., Nov. 25, 2009, 37(1):e7, 9 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
Mignardi et al., "Oligonucleotide gap-fill ligation for mutation detection and sequencing in situ," Nucleic Acids Research, Aug. 3, 2015, 43(22):e151, 12 pages.
Mohsen et al.. "The Discovery of Rolling Circle Amplification and Rolling Circle Transcription," Acc Chem Res., Nov. 15, 2016, 49(11):2540-2550, 25 pages.
Nallur et al., "Signal amplification by rolling circle amplification on DNA microarrays," Nucleic Acids Res., Dec. 1, 2001, 29(23):e118, 9 pages.
Raj et al., "Imaging individual mRNA molecules using multiple singly labeled probes," Nature Methods, Oct. 2008, 5(10):877-879, 9 pages.

(56) References Cited

OTHER PUBLICATIONS

Schweitzer et al., "Immunoassays with rolling circle DNA amplification: A versatile platform for ultrasensitive antigen detection," Proc. Natl Acad. Sci. USA, May 22, 2000, 97:10113-119.

Takei et al., "Integrated Spatial Genomics Reveals Global Architecture of Single Nuclei," Nature, Jan. 27, 2021, 590(7845):344-350, 53 pages.

Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.

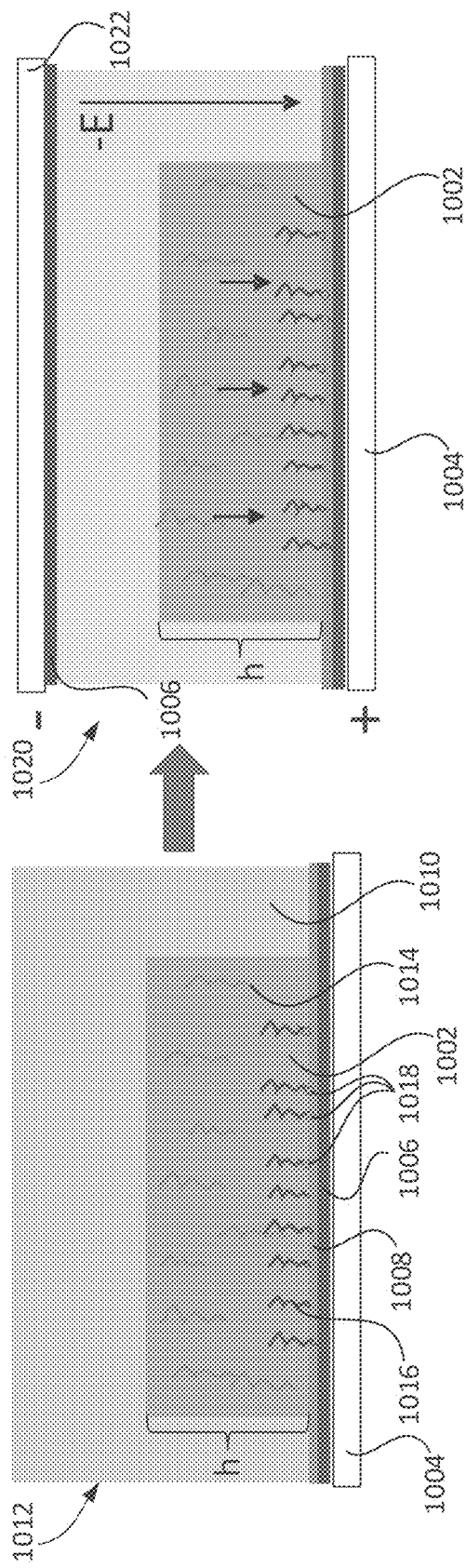
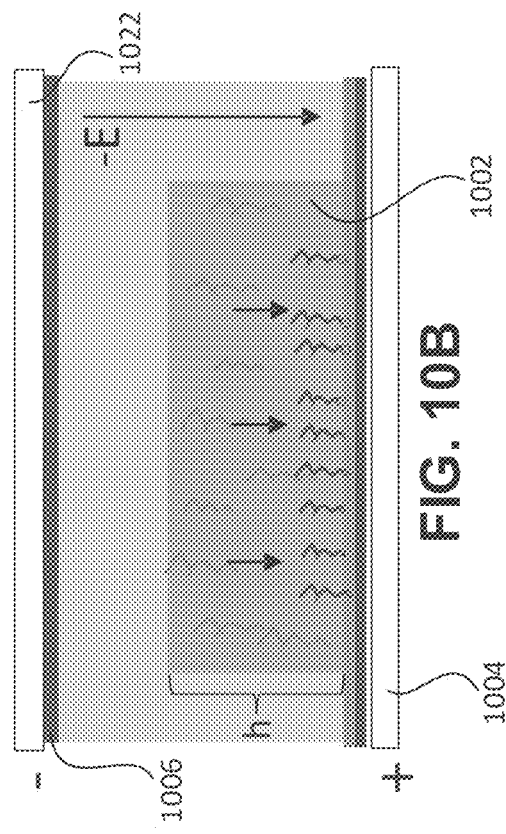
FIG. 10A
FIG. 10B

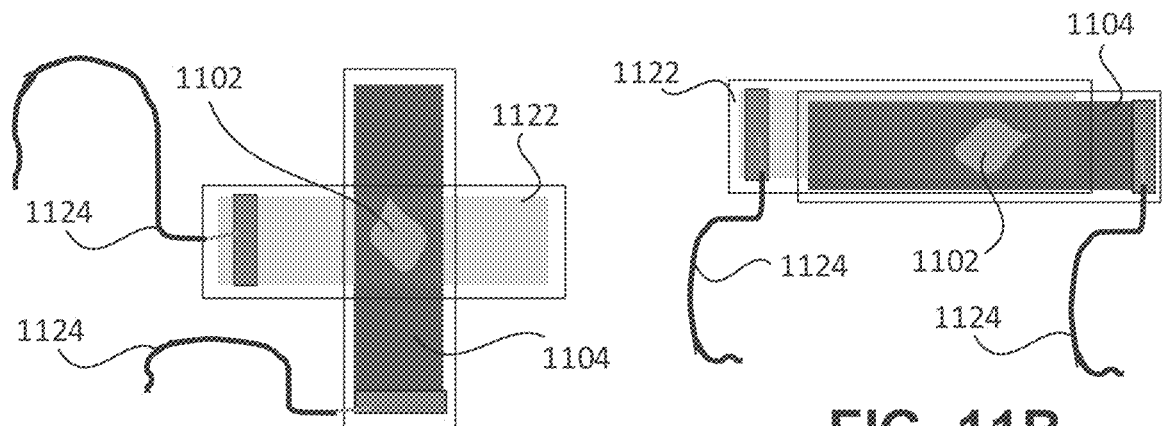
FIG. 11A
FIG. 11B
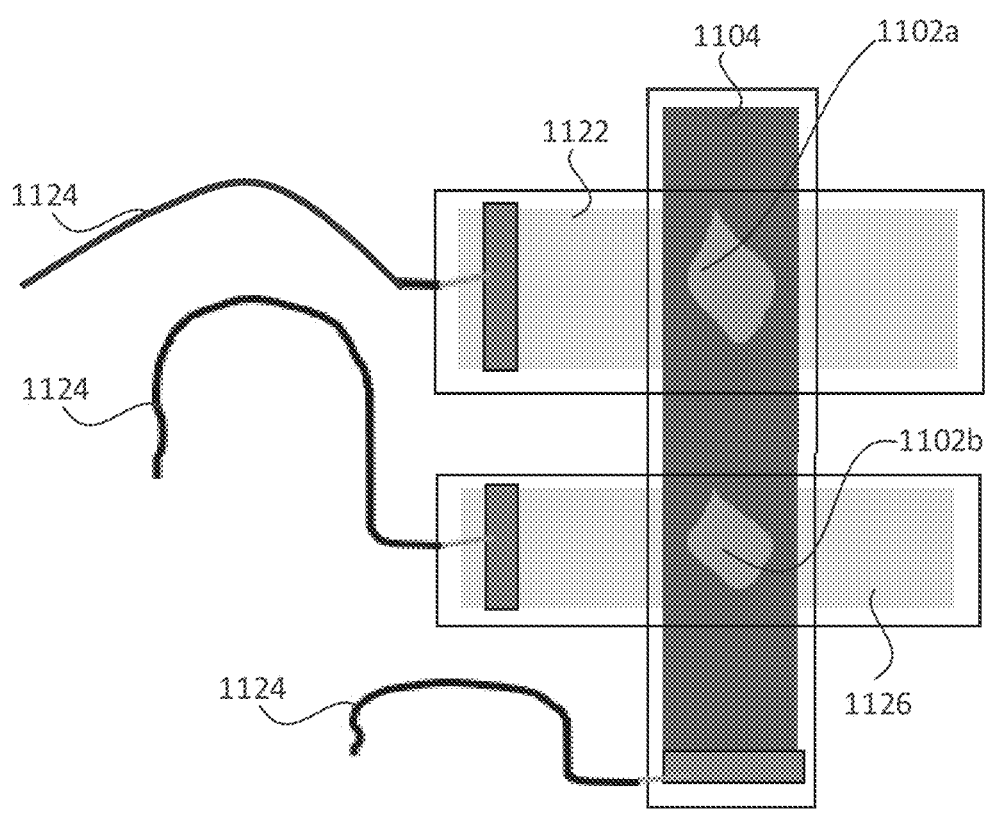
FIG. 11C

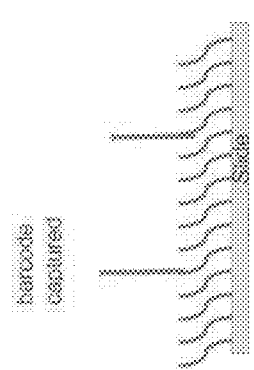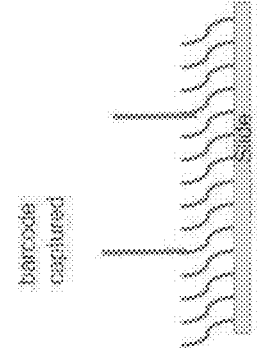
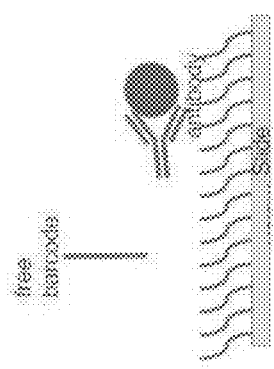
FIG. 17A
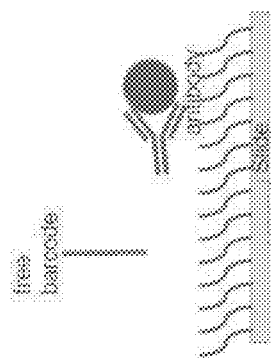
FIG. 17B
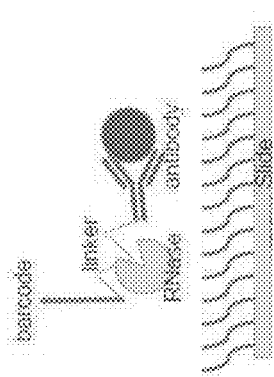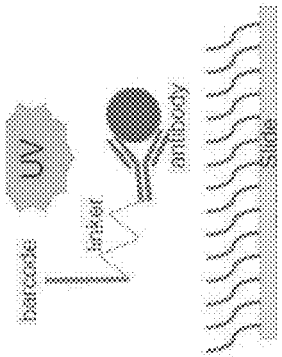

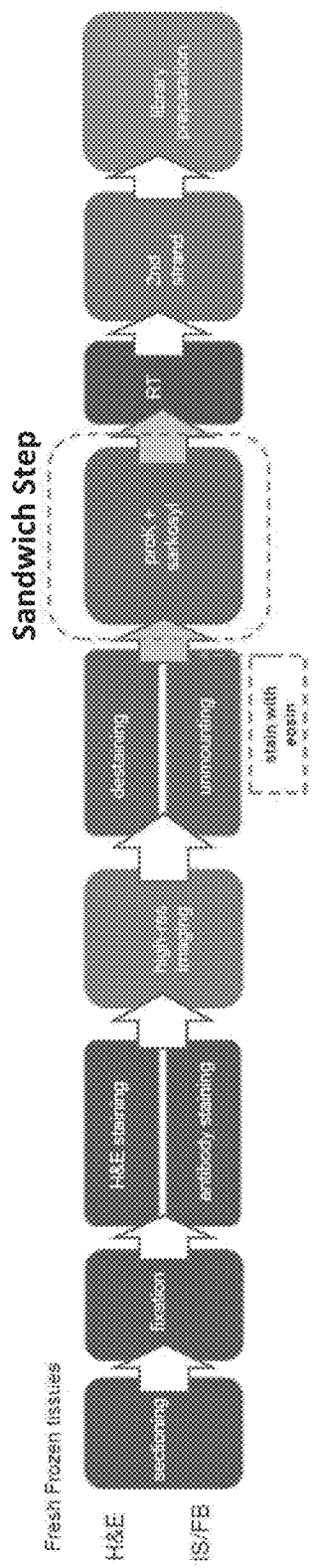
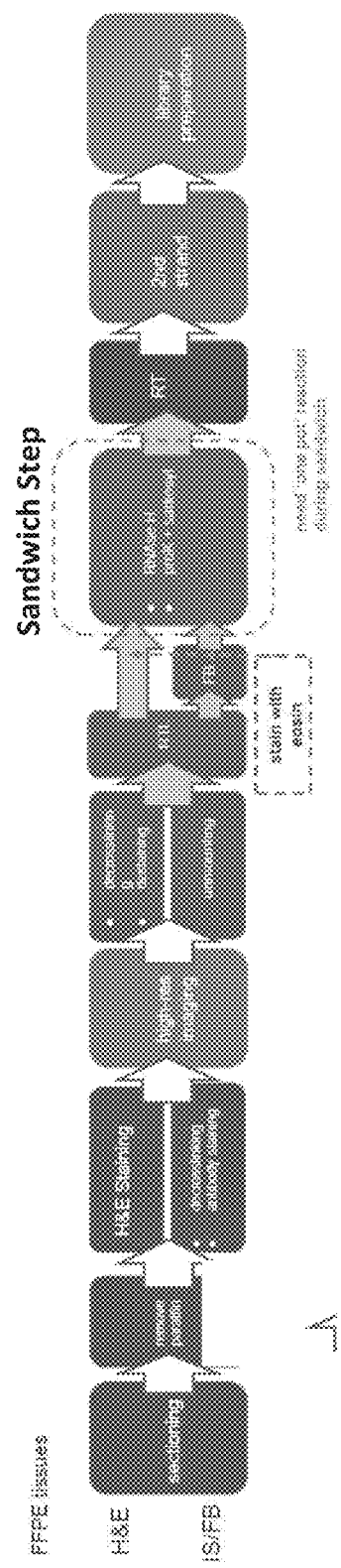
FIG. 19A
FIG. 19B

FIG. 20

| | | Valid barcodes | Valid UMIs | Fraction Reads in Spots Under Tissue | Sequencing saturation | Reads mapped confidently to transcriptome | Fraction reads unmapped | Fraction targeted reads usable | Total Number of Targeted Genes Detected | Median panel genes detected at 1000 panel reads per spot | Median panel UMI counts at 1000 panel reads per spot |
|---|---|---|---|---|---|---|---|---|---|---|---|
| Visium control | Mouse Thymus | 98.0% | 100.0% | 77.7% | 31.9% | 97.3% | 1.2% | 74.1% | 3198 | 213 | 422 |
| | Mouse Testes | 98.0% | 100.0% | 84.8% | 16.1% | 96.3% | 1.1% | 81.7% | 3248 | 385 | 921 |
| | Human B Cancer | - | - | - | - | - | - | - | - | - | - |
| | Human Lung | 97.6% | 100.0% | 87.3% | 78.5% | 95.1% | 2.2% | 81.3% | 2652 | 315 | 164 |
| Sandwich control | Mouse Thymus + Sandwiching | 97.9% | 100.0% | 85.3% | 16.0% | 98.0% | 1.9% | 91.6% | 3257 | 352 | 941 |
| | Mouse Testes + Sandwiching | 97.8% | 100.0% | 78.4% | 19.7% | 96.9% | 2.5% | 73.7% | 3340 | 359 | 918 |
| | Human Lung + Sandwiching | 95.7% | 100.0% | 92.3% | 79.8% | 88.7% | 7.1% | 60.2% | 2888 | 162 | 262 |
| | Human Bcancer + Sandwiching | 83.5% | 100.0% | 80.8% | 91.6% | 29.3% | 50.0% | 26.1% | 2599 | - | - |
| Transfer to same slide | Mouse Thymus/Human Lung | 97.9% | 100.0% | 98.6% | 19.8% | 89.5% | 10.1% | 88.6% | 3225 | 305 | 893 |
| | Mouse Thymus/Human Lung | 97.9% | 100.0% | 96.2% | 19.5% | 8.1% | 91.5% | 7.7% | 2575 | 128 | 174 |
| Transfer to same slide | Mouse Testes/Human Bcancer | 97.9% | 100.0% | 78.1% | 32.7% | 96.0% | 3.4% | 73.6% | 3340 | 266 | 574 |
| | Mouse Testes/Human Bcancer | 97.9% | 100.0% | 98.8% | 32.7% | 2.0% | 97.9% | 2.0% | 2545 | - | - |

| Analysis ID | Sample | Description | Permeabilization time | mm10 Median genes per spot (30k raw reads per spot) | mm10 Median umi counts per spot (30k raw reads per spot) |
|---|---|---|---|---|---|
| 1046321 | Mouse Brains (FF) | Non-sandwich control | 5 minutes | 5194 | 17660 |
| 1046322 | | | | 4592 | 13083 |
| 1046514 | | Permeabilization in sandwich assembly | 1 minute | 4072 | 14017 |
| 1046515 | | | | 3758 | 13731 |

FIG. 24

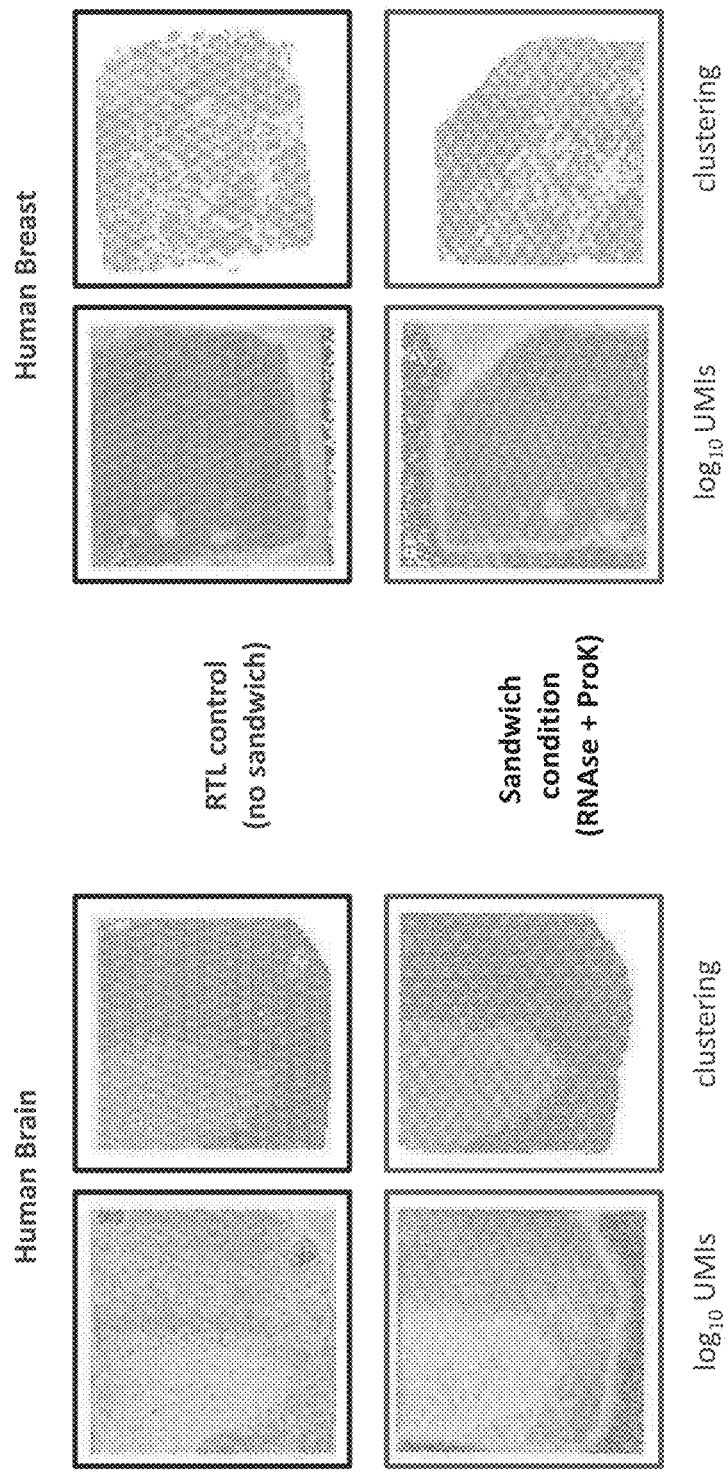

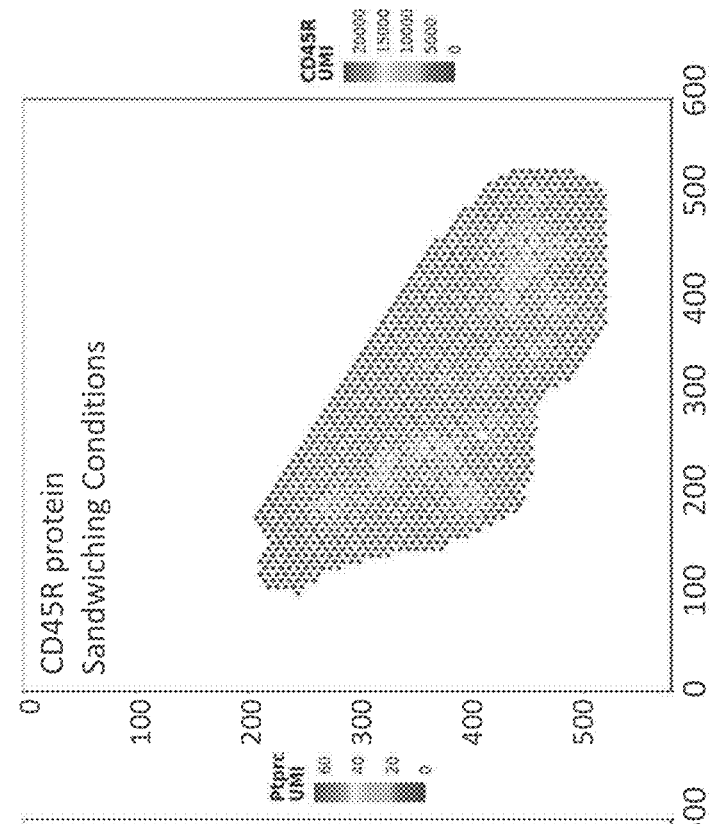
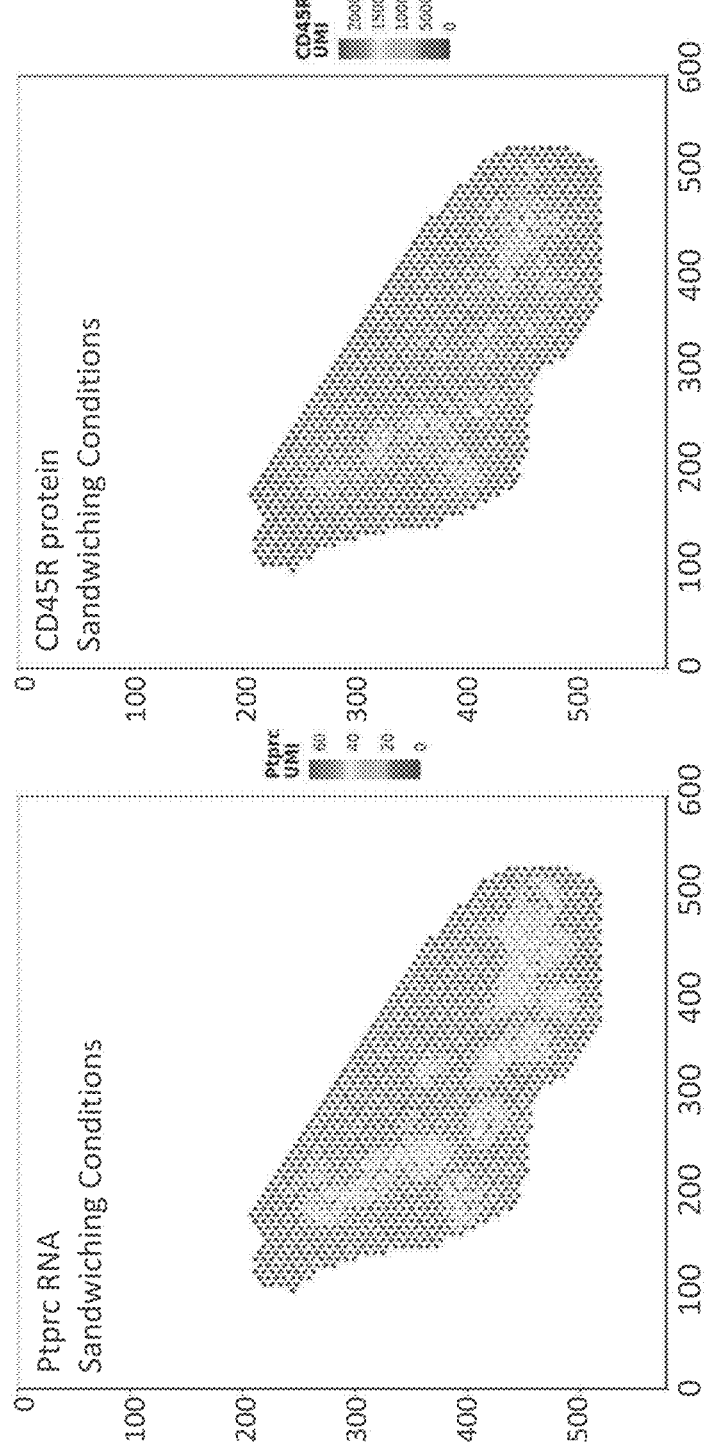
FIG. 28A
FIG. 28B

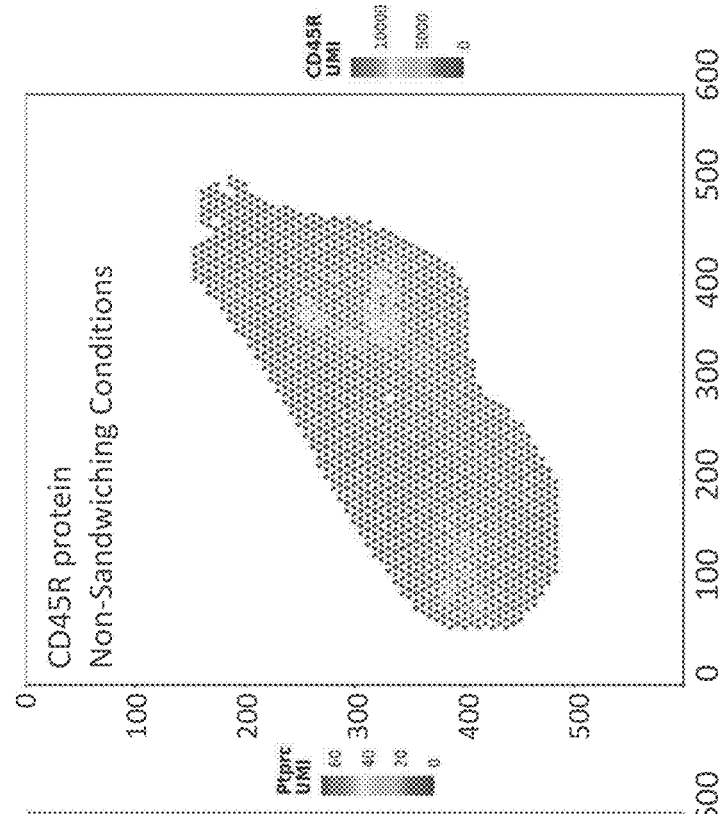
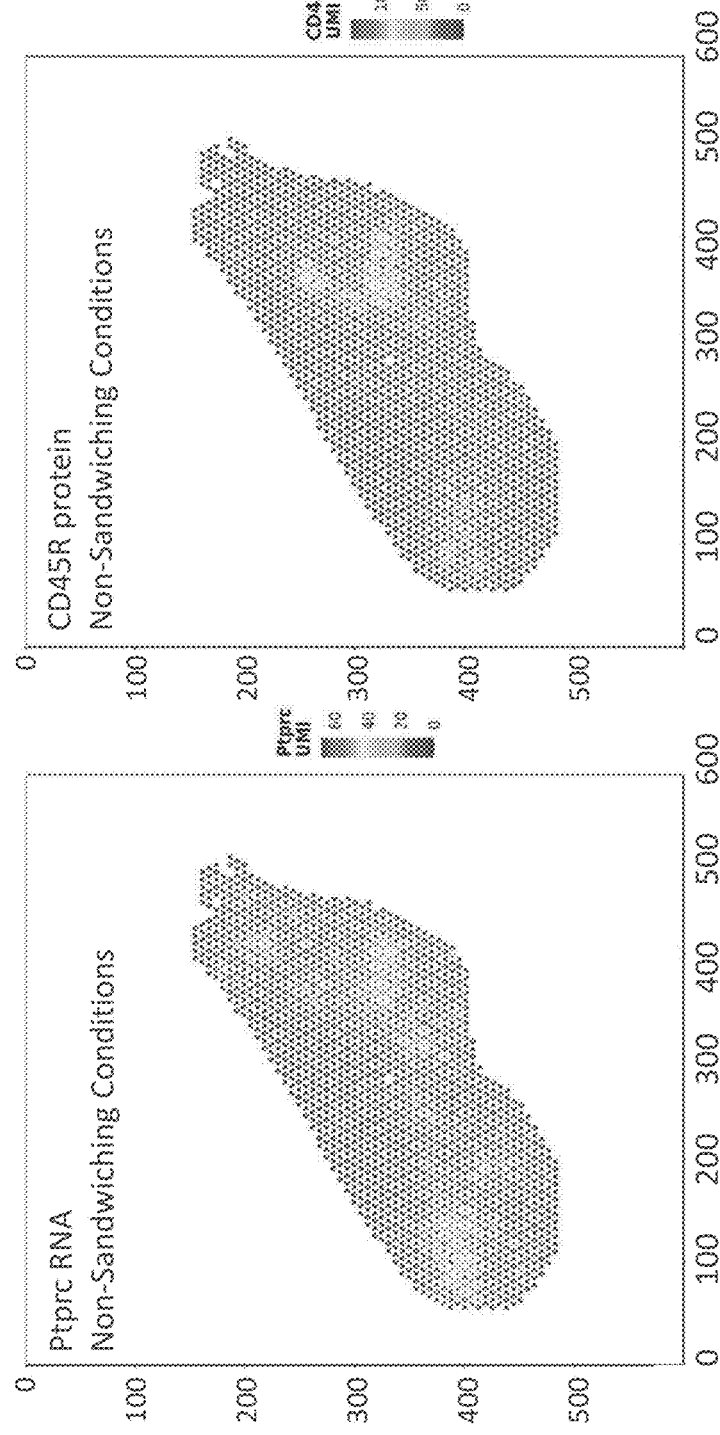
FIG. 28C
FIG. 28D

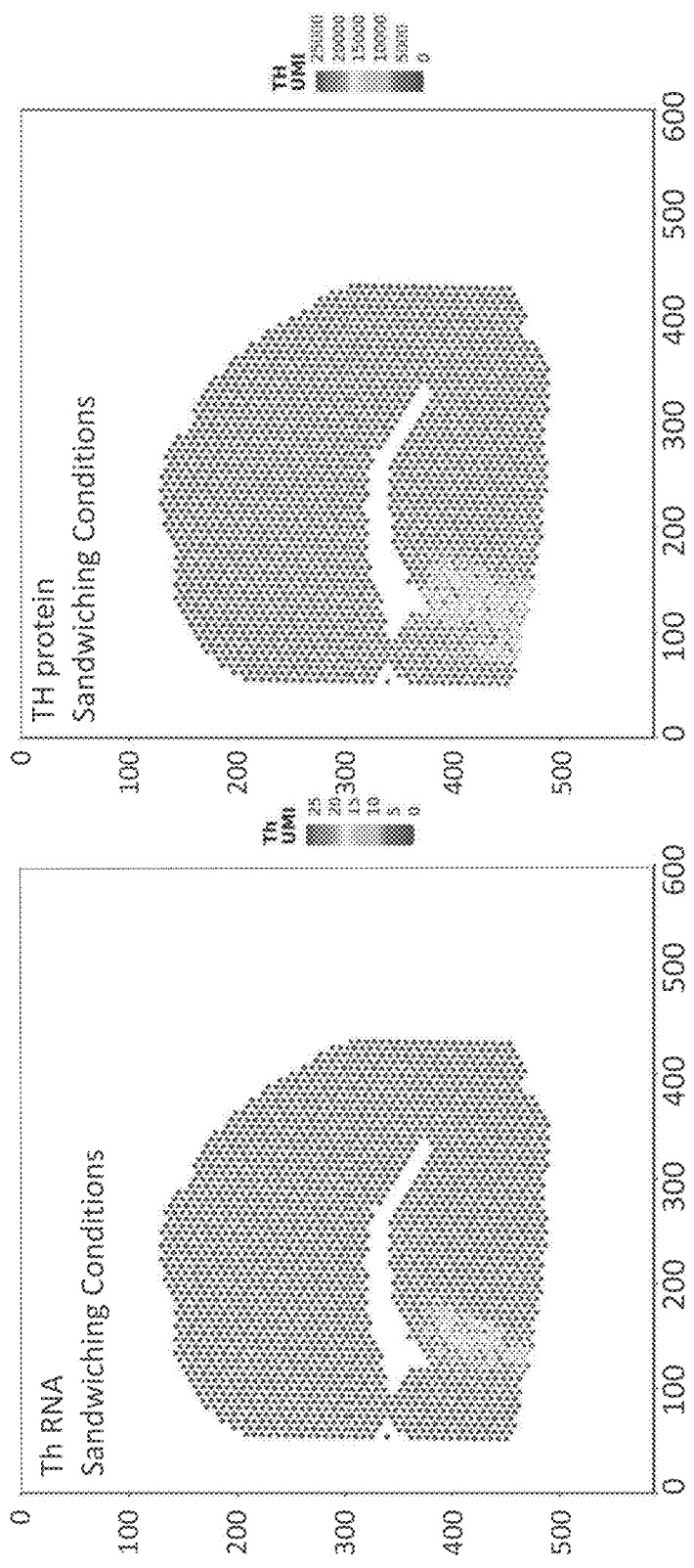

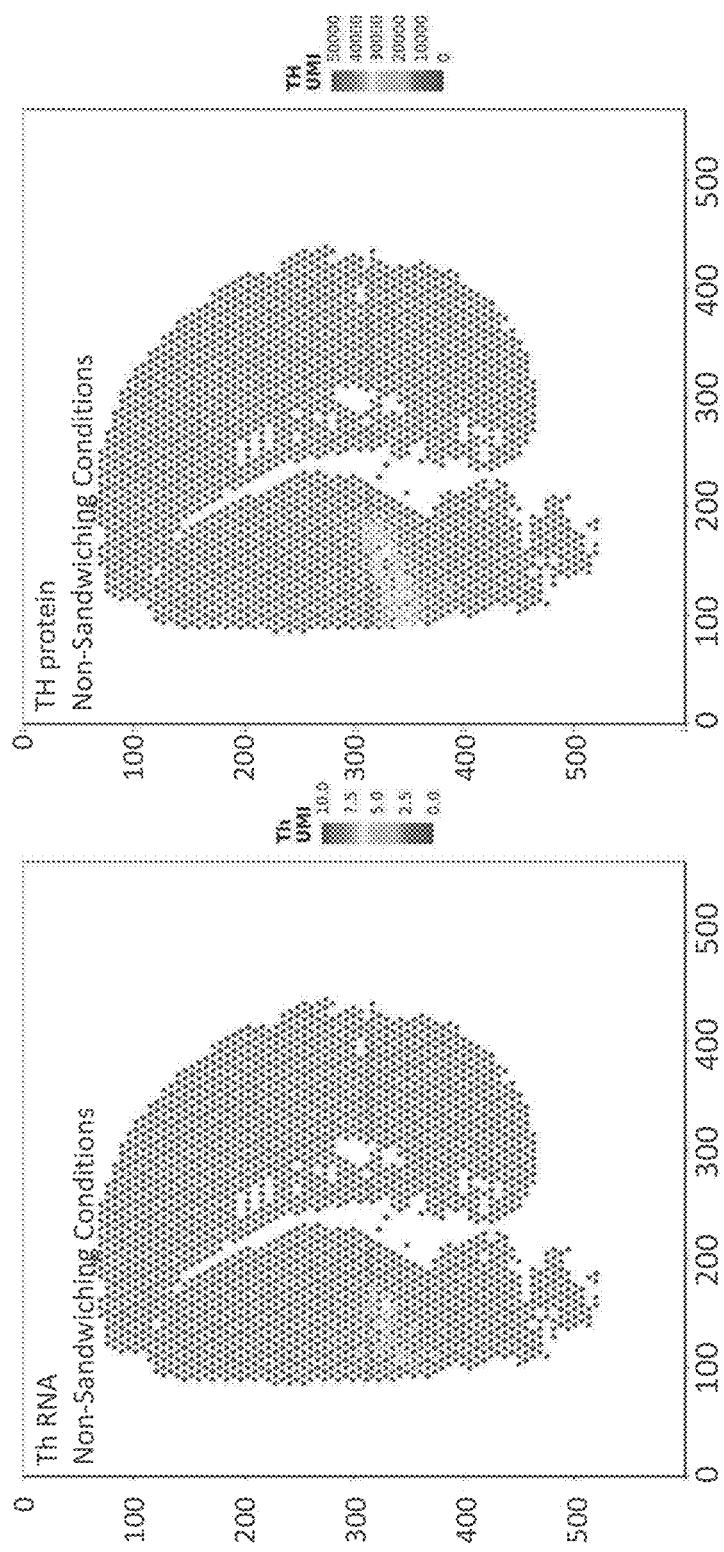

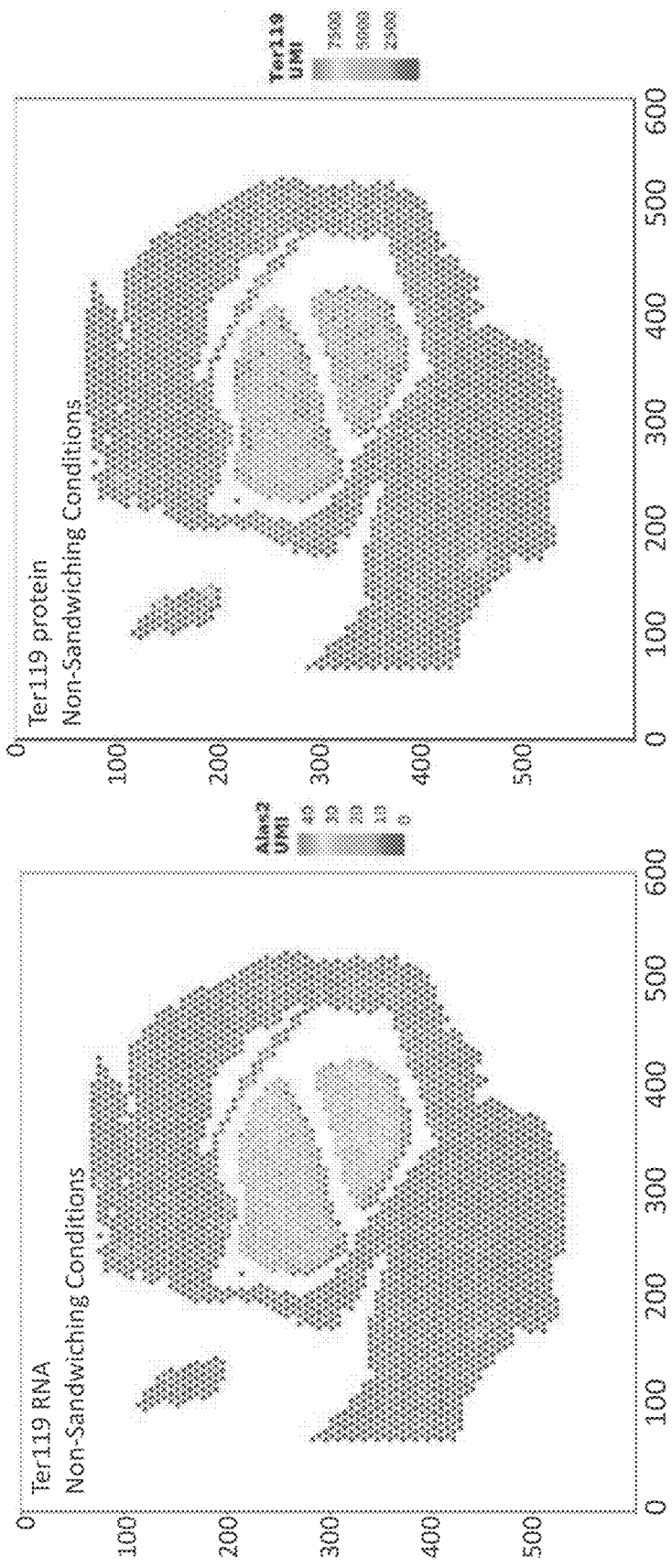

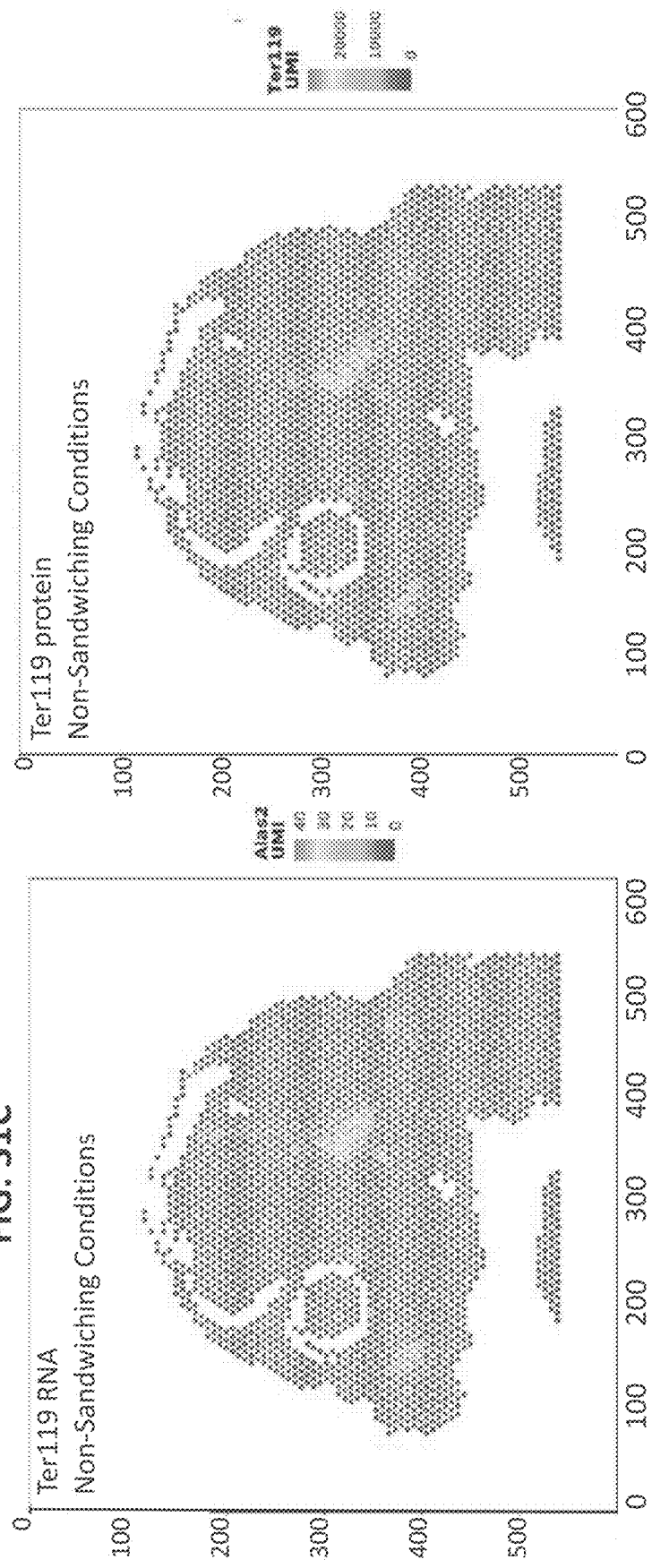

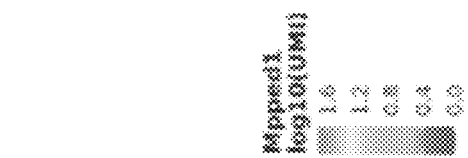
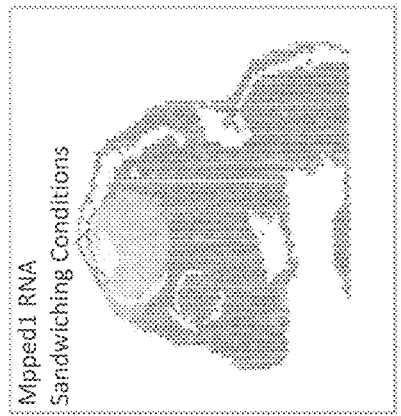
FIG. 32A
FIG. 32C
FIG. 32B

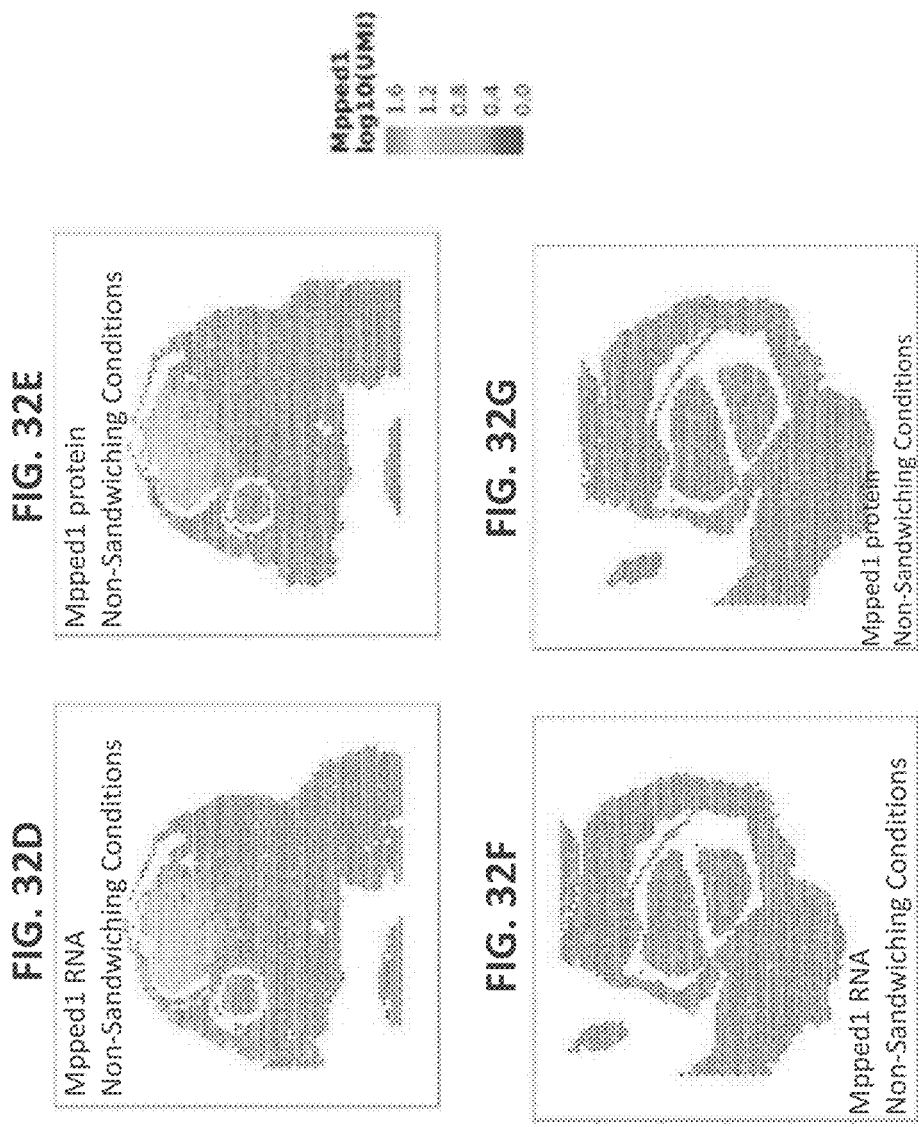

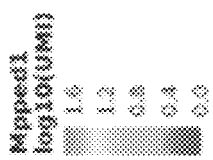
FIG. 32H
Mpped1 RNA
Non-Sandwiching Conditions
(Detection of RNA only)
FIG. 32I
Mpped1 RNA
Non-Sandwiching Conditions
(Detection of RNA only)

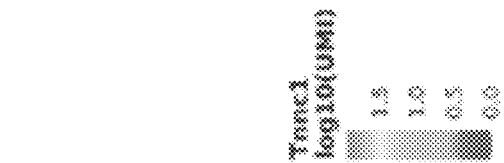
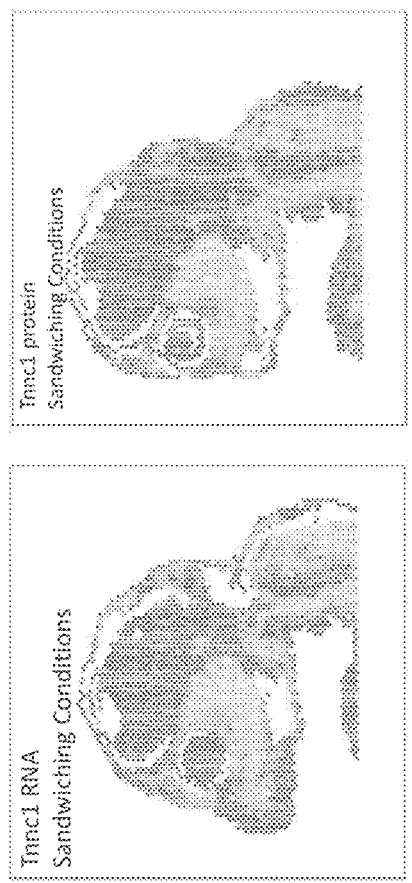
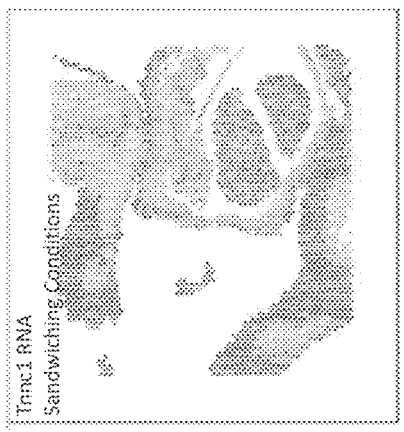

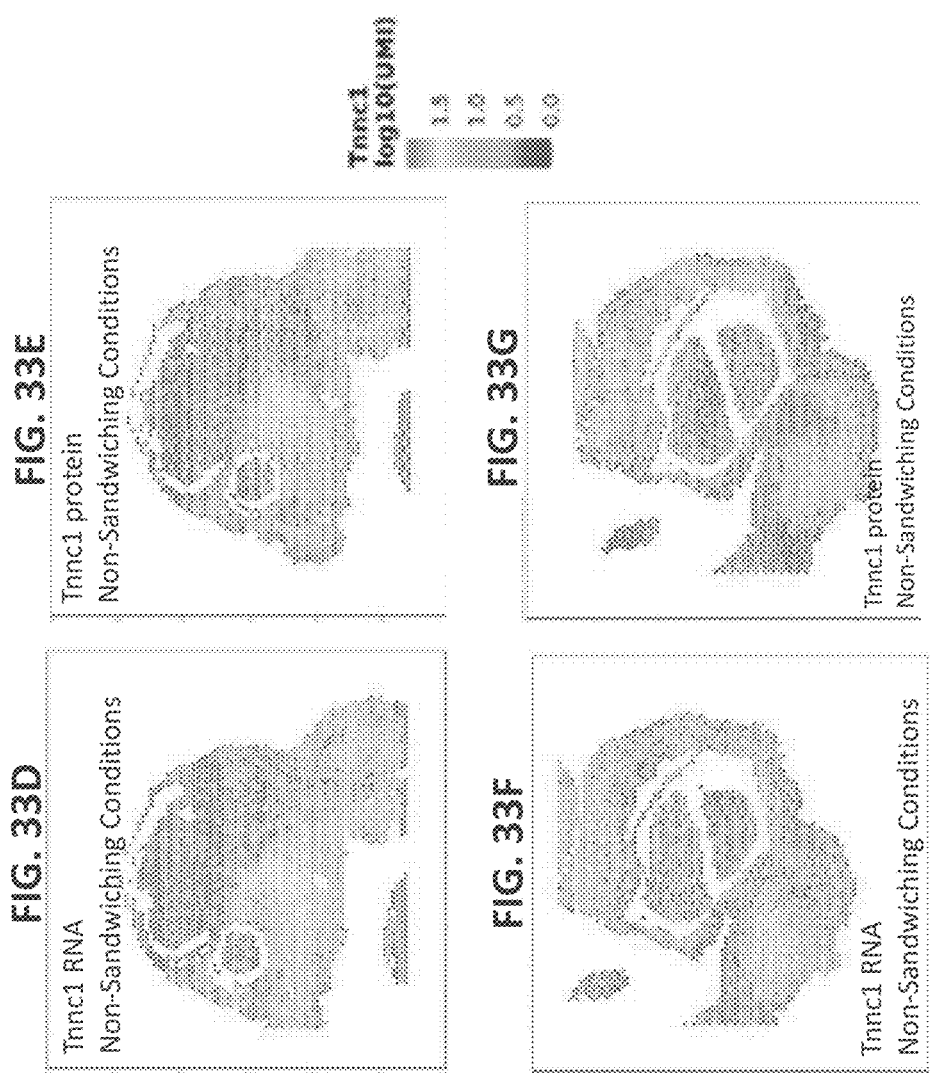

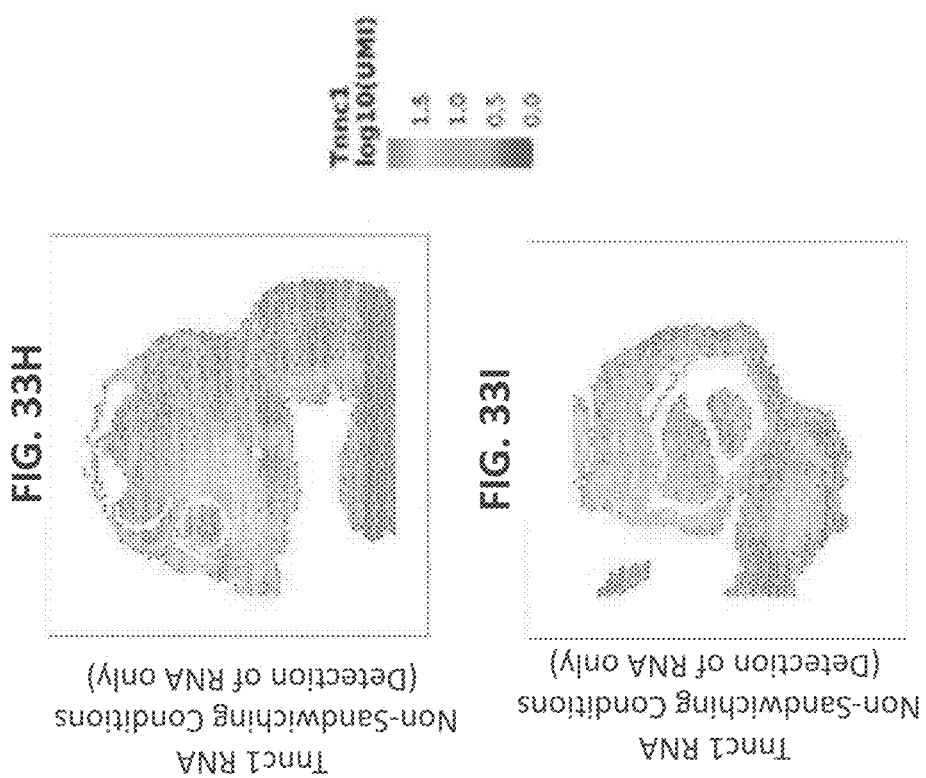

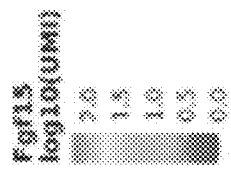
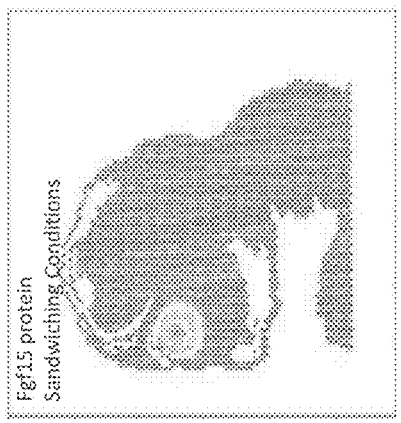
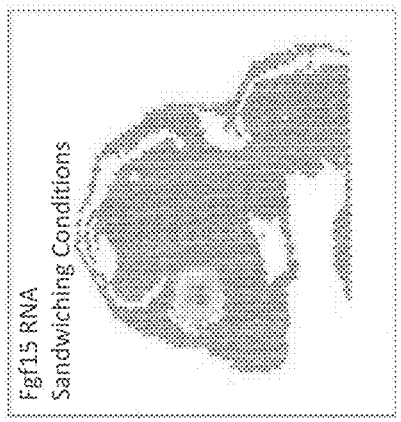
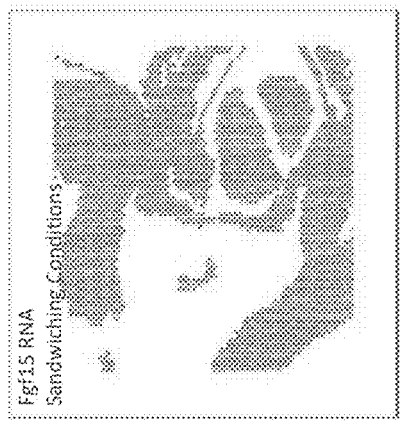
FIG. 34A
FIG. 34B
FIG. 34C

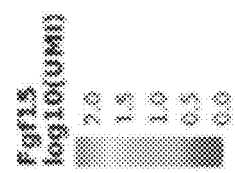
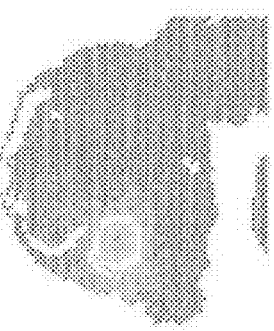
FIG. 34D
Fgf15 RNA
Non-Sandwiching Conditions
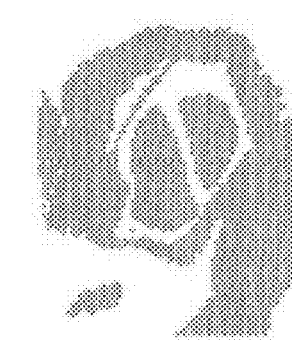
FIG. 34E
Fgf15 protein
Non-Sandwiching Conditions
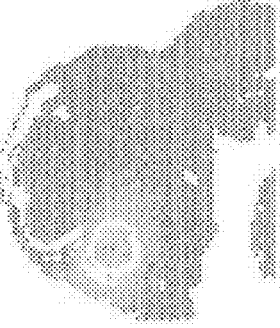
FIG. 34F
Fgf15 RNA
Non-Sandwiching Conditions
FIG. 34G
Fgf15 protein
Non-Sandwiching Conditions

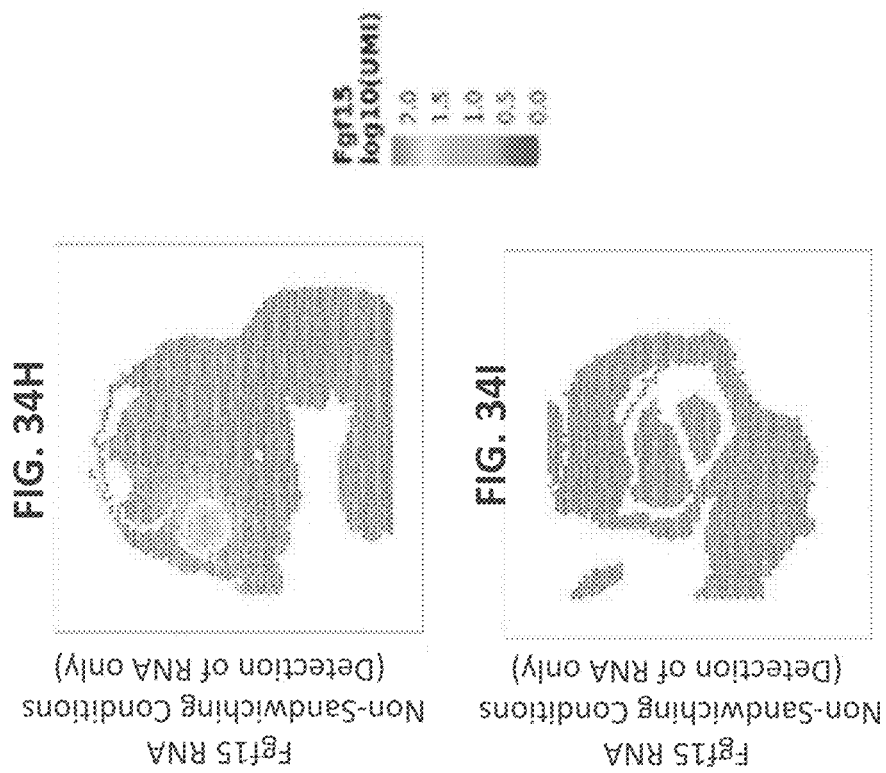

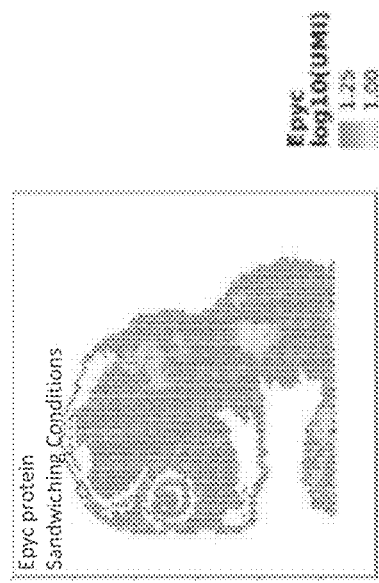
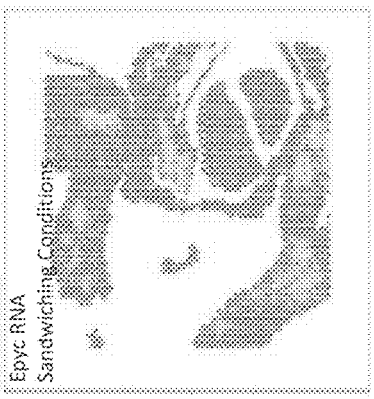
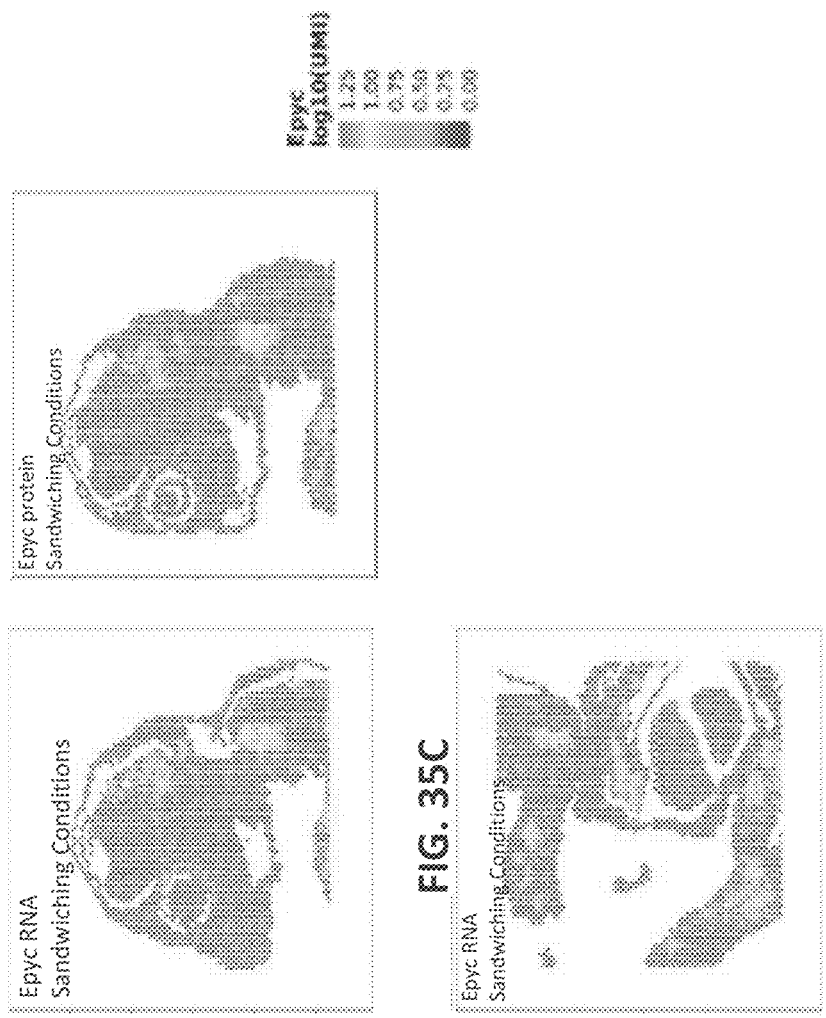
FIG. 35A
FIG. 35B
FIG. 35C

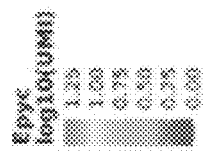
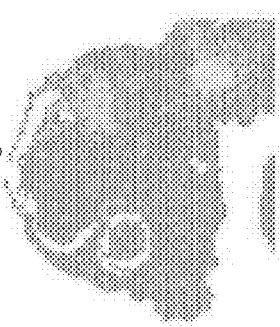
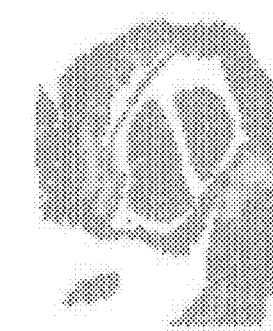
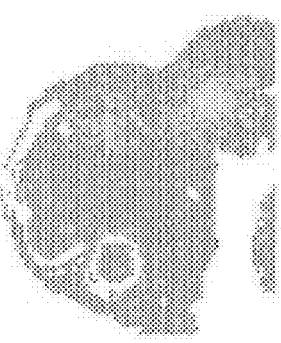
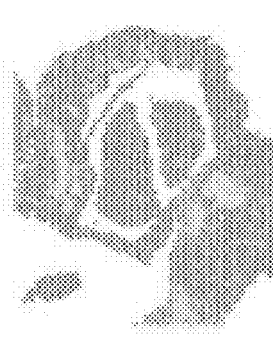
FIG. 35D — Epyc RNA Non-Sandwiching Conditions
FIG. 35E — Epyc protein Non-Sandwiching Conditions
FIG. 35F — Epyc RNA Non-Sandwiching Conditions
FIG. 35G — Epyc protein Non-Sandwiching Conditions

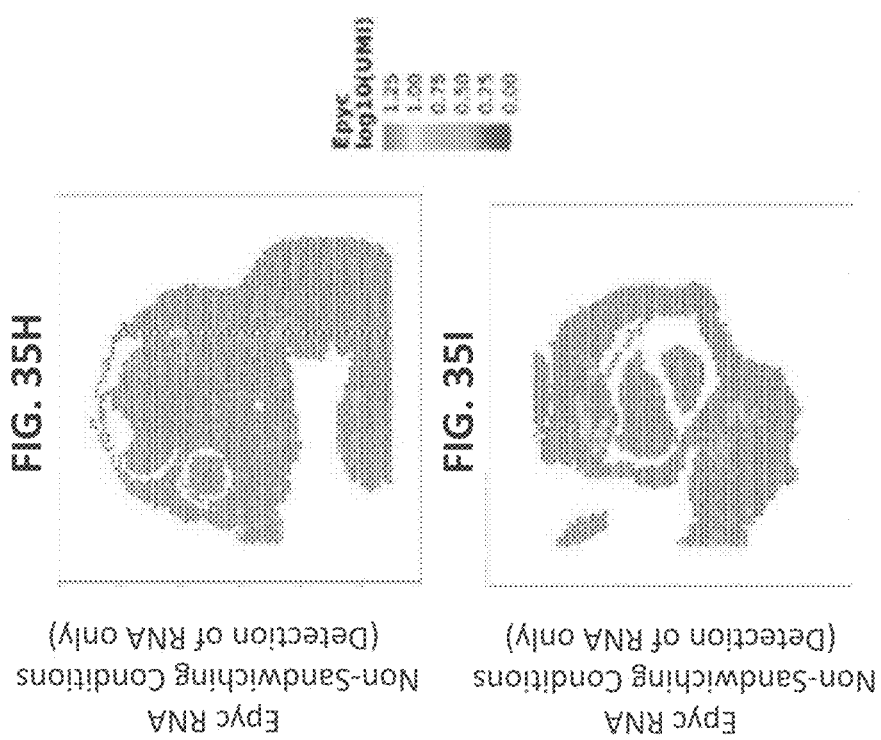
FIG. 35H Epyc RNA Non-Sandwiching Conditions (Detection of RNA only)
FIG. 35I Epyc RNA Non-Sandwiching Conditions (Detection of RNA only)

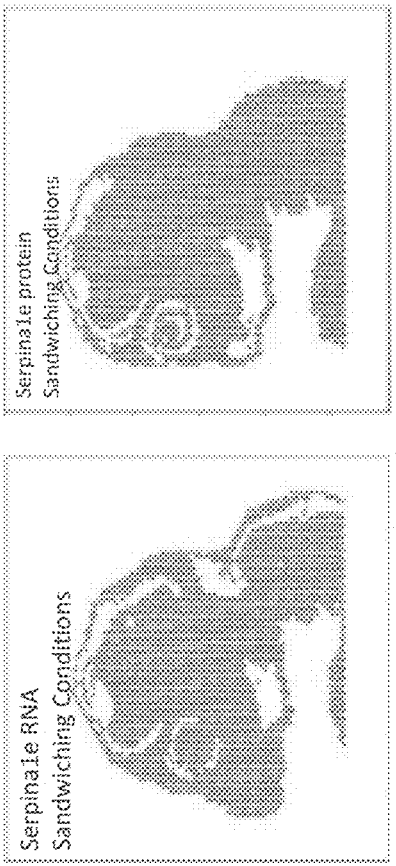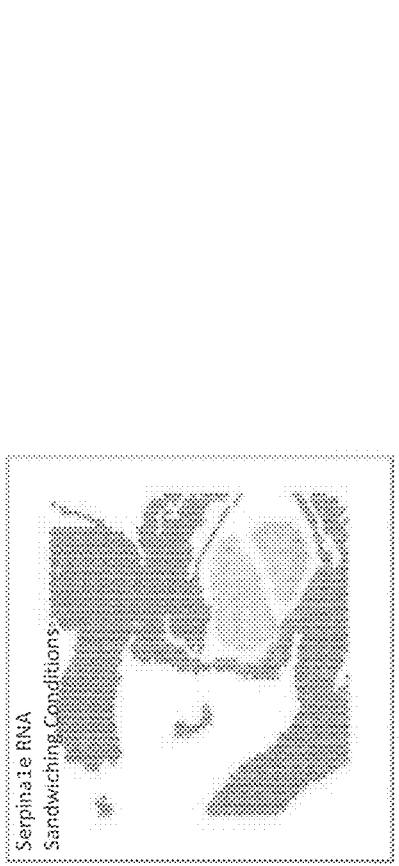

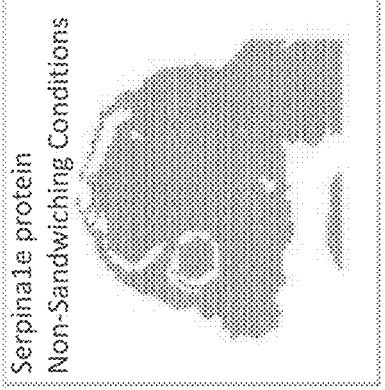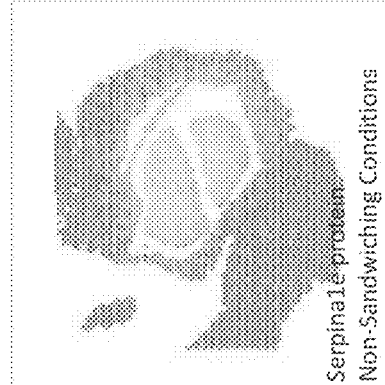
FIG. 36D Serpina1e RNA Non-Sandwiching Conditions
FIG. 36E Serpina1e protein Non-Sandwiching Conditions
FIG. 36F Serpina1e RNA Non-Sandwiching Conditions
FIG. 36G Serpina1e protein Non-Sandwiching Conditions

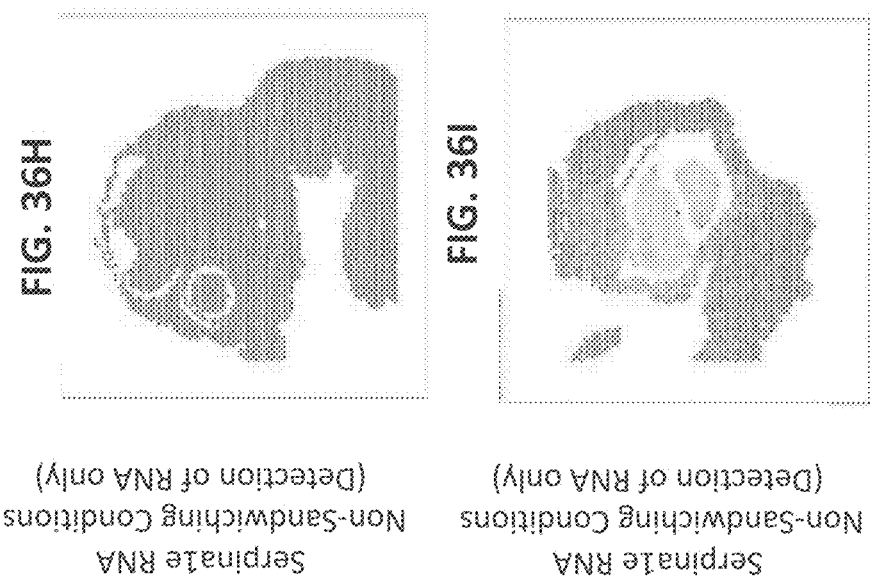

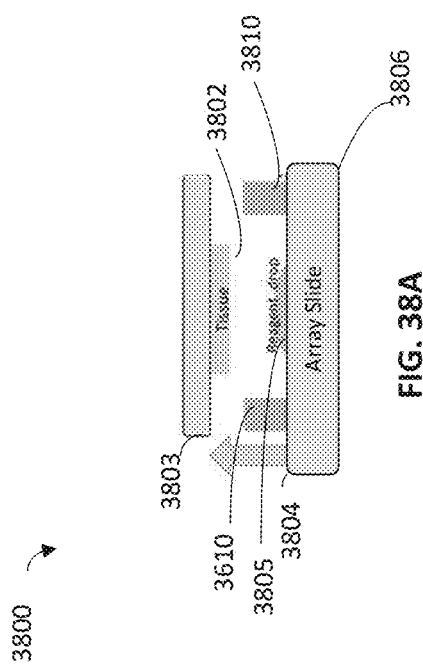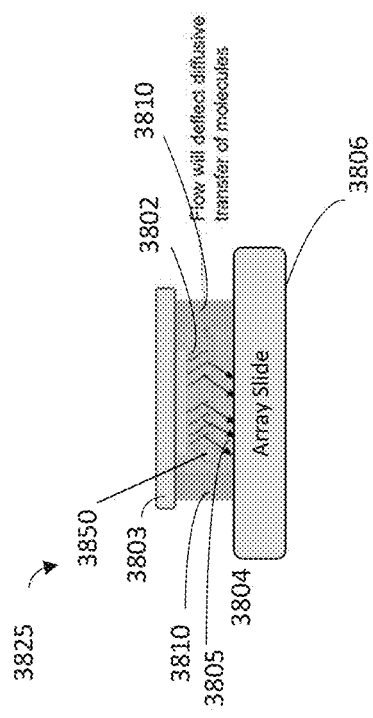

METHODS, COMPOSITIONS, AND SYSTEMS FOR CAPTURING PROBES AND/OR BARCODES

CROSS-REFERENCE TO RELATED APPLICATIONS

Pursuant to 35 U.S.C. § 119(e), this application is a continuation of International Application PCT/US2021/061401, with an international filing date of Dec. 1, 2021, which claims the benefit of U.S. Provisional Application Ser. No. 63/128,796, filed Dec. 21, 2020; 63/148,825, filed Feb. 12, 2021; and 63/252,323, filed Oct. 5, 2021. The entire contents of each application are incorporated by reference herein.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Spatial analysis of an analyte within a biological sample may require determining the sequence of the analyte sequence or a complement thereof and the sequence of the spatial barcode or a complement thereof to identify the location of the analyte. The biological sample may be placed on a solid support to improve specificity and efficiency when being analyzed for identification or characterization of an analyte, such as DNA, RNA or other genetic material, within the sample.

SUMMARY

The present disclosure features methods, compositions, devices, and systems for determining the location and abundance of an analyte in a biological sample. Determining the spatial location and abundance of analytes (e.g., proteins, DNA, or RNA) within a biological sample leads to better understanding of spatial heterogeneity in various contexts, such as disease models. Described herein are methods for capturing probes and/or barcodes to a capture domain. In some instances, the techniques disclosed herein facilitate downstream processing, such as sequencing of the probes and/or barcodes bound to a capture domain.

In some examples, the methods, compositions, devices, and systems disclosed herein utilize RNA-templated ligation (RTL) for analyzing an analyte (e.g., RNA) in a biological sample. In some examples, RTL is used in combination with a "sandwich process," wherein the analyte is transferred from a first substrate to a second substrate for further downstream processing. In some examples, analyte capture agents are used for analyzing an analyte (e.g., protein) in a biological sample. In some examples, the methods disclosed herein allow spatial analysis of two different types of analytes.

In some instances, disclosed herein is a method for analyzing an analyte in a biological sample mounted on a first substrate comprising: hybridizing a first probe oligonucleotide and a second probe oligonucleotide to the analyte, wherein the first probe oligonucleotide and the second probe oligonucleotide each comprise a sequence that is substantially complementary to adjacent sequences of the analyte, and wherein the second probe oligonucleotide comprises a capture probe binding domain; coupling the first probe oligonucleotide and the second probe oligonucleotide, thereby generating a connected probe; aligning the first substrate with a second substrate comprising an array, such that at least a portion of the biological sample is aligned with at least a portion of the array, wherein the array comprises a plurality of capture probes, wherein a capture probe of the plurality of capture probes comprises: (i) a spatial barcode and (ii) a capture domain; when the biological sample is aligned with at least a portion of the array, (i) releasing the connected probe from the analyte and (ii) migrating the connected probe from the biological sample to the array; and hybridizing the connected probe to the capture domain.

In some instances, the first probe oligonucleotide and the second probe oligonucleotide are on a contiguous nucleic acid sequence. In some instances, the first probe oligonucleotide is on the 3' end of the contiguous nucleic acid sequence. In some instances, the second probe oligonucleotide is on the 5' end of the contiguous nucleic acid sequence. In some instances, the adjacent sequences abut one another. In some instances, the adjacent sequences are at least 1, 2, 3, 4, 5, 6, 7, 8, 9, 10, or more nucleotides away from one another.

In some instances, the methods further include generating an extended first probe oligonucleotide, wherein the extended first probe oligonucleotide comprises a sequence complementary to a sequence between the sequence hybridized to the first probe oligonucleotide and the sequence hybridized to the second probe oligonucleotide.

In some instances, the methods further include generating an extended second probe oligonucleotide using a polymerase, wherein the extended second probe oligonucleotide comprises a sequence complementary to a sequence between the sequence hybridized to the first probe oligonucleotide and the sequence hybridized to the second probe oligonucleotide.

In some instances, the methods further include hybridizing a third probe oligonucleotide to the first probe oligonucleotide and the second probe oligonucleotide.

In some instances, the third probe oligonucleotide comprises: a sequence that is at least 80%, at least 85%, at least 90%, at least 95%, at least 96%, at least 97%, at least 98%, or at least 99%, or 100% complementary to a portion of the first probe oligonucleotide that hybridizes to the third probe oligonucleotide; and a sequence that is at least 80%, at least 85%, at least 90%, at least 95%, at least 96%, at least 97%, at least 98%, or at least 99%, or 100% complementary to a portion of the second probe oligonucleotide that hybridizes to the third probe oligonucleotide.

In some instances, the coupling the first probe oligonucleotide and the second probe oligonucleotide comprises ligating via a ligase the first probe oligonucleotide and the second probe oligonucleotide. In some instances, the coupling the first probe oligonucleotide and the second probe oligonucleotide comprises ligating via a ligase: (a) the first probe oligonucleotide and the extended second probe oligonucleotide; or (b) the extended first probe oligonucleotide and the second probe oligonucleotide. In some instances, the ligase is selected from a splintR ligase, a single stranded DNA ligase, or a T4 DNA ligase.

In some instances, the methods further include amplifying the connected probe prior to the releasing step, optionally wherein the amplifying comprises rolling circle amplification.

In some instances, the aligning step comprises: (i) mounting the first substrate on a first member of a support device, the first member configured to retain the first substrate; (ii) mounting the second substrate on a second member of the support device; (iii) applying a reagent medium to the first substrate and/or the second substrate, wherein the reagent medium comprises a permeabilization agent and optionally an agent for releasing the connected probe; and (iv) operating an alignment mechanism of the support device to move the first member and/or the second member such that at least a portion of the biological sample is aligned with at least a portion of the array, and such that the portion of the biological sample and the portion of the array contact the reagent medium.

In some instances, the alignment mechanism is coupled to the first member, the second member, or both the first member and the second member. In some instances, the alignment mechanism comprises a linear actuator, optionally wherein: the linear actuator is configured to move the second member along an axis orthogonal to the plane or the first member and/or the second member, and/or the linear actuator is configured to move the first member along an axis orthogonal to the plane of the first member and/or the second member, and/or the linear actuator is configured to move the first member, the second member, or both the first member and the second member at a velocity of at least 0.1 mm/sec, and/or the linear actuator is configured to move the first member, the second member, or both the first member and the second member with an amount of force of at least 0.1 lbs.

In some instances, during the releasing step (d), a separation distance is maintained between the first substrate and the second substrate, optionally wherein the separation distance is less than 50 microns, optionally wherein the separation distance is between 2-25 microns, optionally wherein the separation distance is measured in a direction orthogonal to the surface of the first substrate that supports the biological sample, and/or at least the portion of the biological sample is vertically aligned with the at least portion of the array.

In some instances, at least one of the first substrate and the second substrate further comprise a spacer, wherein after the first and second substrate being mounted on the support device, the spacer is disposed between the first substrate and second substrate and is configured to maintain the reagent medium within a chamber formed by the first substrate, the second substrate, and the spacer, and maintain a separation distance between the first substrate and the second substrate, the spacer positioned to at least partially surround an area on the first substrate on which the biological sample is disposed and/or the array disposed on the second substrate, wherein the area of the first substrate, the spacer, and the second substrate at least partially encloses a volume comprising the biological sample.

In some instances, the chamber comprises a partially or fully sealed chamber, and/or the second substrate comprises the spacer, and/or the first substrate comprises the spacer, and/or the applying the reagent medium to the first substrate and/or the second substrate comprises applying the reagent medium to a region of the spacer, the region outside an enclosed area of the second substrate, the enclosed area formed by the spacer.

In some instances, as the first substrate and/or the second substrate are moved via the alignment mechanism, the first substrate is at an angle relative to the second substrate such that a dropped slide of the first substrate and a portion of the second substrate contact the reagent medium, optionally wherein: the dropped side of the first substrate urges the reagent medium toward the opposite direction, and/or the alignment mechanism further moves the first substrate and/or the second substrate to maintain an approximately parallel arrangement of the first substrate and the second substrate and a separation distance between the first substrate and the second substrate, optionally when the approximately parallel arrangement and the separation distance are maintained, the spacer fully encloses and surrounds the at least portion of the biological sample and the at least portion of the array, and the spacer forms the sides of the chamber which hold a volume of the reagent medium.

In some instances, the methods further include contacting the biological sample with a reagent medium comprising a permeabilization agent and an agent for releasing the connected probe, thereby permeabilizing the biological sample and releasing the connected probe from the analyte. In some instances, the agent for releasing the connected probe comprises a nuclease. In some instances, the nuclease comprises an RNase, optionally wherein the RNase is selected from RNase A, RNase C, RNase H, or RNase I. In some instances, the permeabilization agent comprises a protease. In some instances, the protease is selected from trypsin, pepsin, elastase, or proteinase K. In some instances, the reagent medium further comprises a detergent. In some instances, the detergent is selected from sodium dodecyl sulfate (SDS), sarkosyl, saponin, Triton X-100™, or Tween-20™. In some instances, the reagent medium comprises less than 5 w/v % of a detergent selected from SDS and sarkosyl. In some instances, the reagent medium comprises at least 5% w/v % of a detergent selected from SDS and sarkosyl. In some instances, the reagent medium does not comprise sodium dodcyl sulfate (SDS) or sarkosyl.

In some instances, the reagent medium further comprises polyethylene glycol (PEG).

In some instances, the biological sample and the array are contacted with the reagent medium for about 1 to about 60 minutes. In some instances, the biological sample and the array are contacted with the reagent medium for about 30 minutes.

In some instances, the methods further include determining (i) all or a part of the sequence of the connected probe, or a complement thereof, and (ii) all or a part of the sequence of the spatial barcode, or a complement thereof, optionally wherein the method further comprises using the determined sequence of (i) and (ii) to determine the location and abundance of the analyte in the biological sample. In some instances, the determining comprises sequencing (i) all or a part of the sequence of the connected probe, or a complement thereof, and (ii) all or a part of the sequence of the spatial barcode, or a complement thereof.

In some instances, the sequence of the connected probe comprises the sequence of the spatial barcode or the reverse complement thereof, and a sequence corresponding to the analyte in the biological sample or reverse complement thereof.

In some instances, at least 50% of the connected probe released from the portion of the biological sample aligned with the portion of the array are captured by capture probes of the portion of the array. In some instances, at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the connected probe are detected in spots directly under the biological sample.

In some instances, the capture probe comprises a poly(T) sequence. In some instances, the capture probe comprises a sequence specific to the analyte. In some instances, the capture probe further comprises one or more functional domains, a unique molecular identifier (UMI), a cleavage domain, and combinations thereof.

In some instances, the analyte is RNA. In some instances, the analyte is mRNA.

In some instances, the methods include analyzing a different analyte in the biological sample. In some instances, the analyzing of the different analyte comprises: contacting the biological sample with a plurality of analyte capture agents, wherein an analyte capture agent of the plurality of analyte capture agents comprises an analyte binding moiety and a capture agent barcode domain, wherein the analyte binding moiety specifically binds to the different analyte, and wherein the capture agent barcode domain comprises an analyte binding moiety barcode and an capture handle sequence; and hybridizing the capture handle sequence to the capture domain. In some instances, the methods further include determining (i) all or part of the sequence of the capture agent barcode domain; and (ii) all or a part of the sequence of the spatial barcode, or a complement thereof. In some instances, the methods further include using the determined sequence of (i), and (ii) to analyze the different analyte in the biological sample.

In some instances, the releasing step further releases the capture agent barcode domain from the different analyte. In some instances, the different analyte is a protein analyte. In some instances, the protein analyte is an extracellular protein. In some instances, the protein analyte is an intracellular protein. In some instances, the analyte binding moiety is an antibody. In some instances, the analyte capture agent comprises a linker. In some instances, the linker is a cleavable linker. In some instances, the cleavable linker is a photo-cleavable linker, a UV-cleavable linker, or an enzyme cleavable linker. In some instances, the cleavable linker is a photo-cleavable linker.

In some instances, also disclosed herein is a method for analyzing an analyte in a biological sample mounted on a first substrate comprising: contacting the biological sample with a plurality of analyte capture agents, wherein an analyte capture agent of the plurality of analyte capture agents comprises an analyte binding moiety and a capture agent barcode domain, wherein the analyte binding moiety specifically binds to the analyte, and wherein the capture agent barcode domain comprises an analyte binding moiety barcode and an capture handle sequence; aligning the first substrate with a second substrate comprising an array, such that at least a portion of the biological sample is aligned with at least a portion of the array, wherein the array comprises a plurality of capture probes, wherein a capture probe of the plurality of capture probes comprises: (i) a spatial barcode and (ii) a capture domain; when the biological sample is aligned with at least a portion of the array, (i) releasing the capture agent barcode domain from the analyte and (ii) passively or actively migrating the capture agent barcode domain from the biological sample to the array; and coupling the capture handle sequence to the capture domain. In some instances, the methods further include determining (i) all or a part of the capture agent barcode domain, or a complement thereof; and (ii) all or a part of the sequence of the spatial barcode, or a complement thereof. In some instances, the methods further include using the determined sequence of (i) and (ii) to determine the location and abundance of the analyte in the biological sample.

In some instances, the aligning step comprises: (i) mounting the first substrate on a first member of a support device, the first member configured to retain the first substrate; (ii) mounting the second substrate on a second member of the support device; (iii) applying a reagent medium to the first substrate and/or the second substrate, wherein the reagent medium comprises a permeabilization agent and optionally an agent for releasing the connected probe; and (iv) operating an alignment mechanism of the support device to move the first member and/or the second member such that at least a portion of the biological sample is aligned with at least a portion of the array, and such that the portion of the biological sample and the portion of the array contact the reagent medium.

In some instances, the alignment mechanism is coupled to the first member, the second member, or both the first member and the second member. In some instances, the alignment mechanism comprises a linear actuator, optionally wherein: the linear actuator is configured to move the second member along an axis orthogonal to the plane or the first member and/or the second member, and/or the linear actuator is configured to move the first member along an axis orthogonal to the plane of the first member and/or the second member, and/or the linear actuator is configured to move the first member, the second member, or both the first member and the second member at a velocity of at least 0.1 mm/sec, and/or the linear actuator is configured to move the first member, the second member, or both the first member and the second member with an amount of force of at least 0.1 lbs.

In some instances, during the releasing step (d), a separation distance is maintained between the first substrate and the second substrate, optionally wherein the separation distance is less than 50 microns, optionally wherein the separation distance is between 2-25 microns, optionally wherein the separation distance is measured in a direction orthogonal to the surface of the first substrate that supports the biological sample, and/or at least the portion of the biological sample is vertically aligned with the at least portion of the array.

In some instances, at least one of the first substrate and the second substrate further comprise a spacer, wherein after the first and second substrate being mounted on the support device, the spacer is disposed between the first substrate and second substrate and is configured to maintain the reagent medium within a chamber formed by the first substrate, the second substrate, and the spacer, and maintain a separation distance between the first substrate and the second substrate, the spacer positioned to at least partially surround an area on the first substrate on which the biological sample is disposed and/or the array disposed on the second substrate, wherein the area of the first substrate, the spacer, and the second substrate at least partially encloses a volume comprising the biological sample.

In some instances, the chamber comprises a partially or fully sealed chamber, and/or the second substrate comprises the spacer, and/or the first substrate comprises the spacer, and/or the applying the reagent medium to the first substrate and/or the second substrate comprises applying the reagent medium to a region of the spacer, the region outside an enclosed area of the second substrate, the enclosed area formed by the spacer.

In some instances, as the first substrate and/or the second substrate are moved via the alignment mechanism, the first substrate is at an angle relative to the second substrate such that a dropped slide of the first substrate and a portion of the second substrate contact the reagent medium, optionally wherein: the dropped side of the first substrate urges the reagent medium toward the opposite direction, and/or the alignment mechanism further moves the first substrate and/or the second substrate to maintain an approximately parallel arrangement of the first substrate and the second substrate and a separation distance between the first substrate and the second substrate, optionally when the approximately parallel arrangement and the separation distance are maintained, the spacer fully encloses and surrounds the at least portion of the biological sample and the at least portion of the array, and the spacer forms the sides of the chamber which hold a volume of the reagent medium.

In some instances, the releasing comprises contacting the biological sample and the array with a reagent medium comprising a nuclease. In some instances, the coupling of the capture handle sequence to the capture domain comprises hybridization. In some instances, the nuclease comprises an RNase. In some instances, the RNase is selected from RNase A, RNase C, RNase H, and RNase I. In some instances, the reagent medium further comprises a permeabilization agent. In some instances, the releasing further comprises simultaneously permeabilizing the biological sample and releasing the capture agent barcode domain from the analyte binding moiety. In some instances, the permeabilization agent comprises a protease. In some instances, the protease is selected from trypsin, pepsin, elastase, or Proteinase K. In some instances, the reagent medium further comprises a detergent. In some instances, the detergent is selected from sodium dodecyl sulfate (SDS), sarkosyl, saponin, Triton X-100™, or Tween-20™. In some instances, the reagent medium comprises less than 5 w/v % of a detergent selected from SDS and sarkosyl. In some instances, the reagent medium comprises as least 5% w/v % of a detergent selected from SDS and sarkosyl. In some instances, the reagent medium does not comprise sodium dodcyl sulfate (SDS) or sarkosyl.

In some instances, the reagent medium further comprises PEG.

In some instances, the biological sample and the array are contacted with the reagent medium for about 1 to about 60 minutes.

In some instances, the biological sample and the array are contacted with the reagent medium for about 30 minutes. In some instances, the methods further include analyzing a different analyte in the biological sample. In some instances, the analyzing of the different analyte comprises: hybridizing a first probe oligonucleotide and a second probe oligonucleotide to the different analyte, wherein the first probe oligonucleotide and the second probe oligonucleotide each comprise a sequence that is substantially complementary to adjacent sequences of the different analyte, and wherein the second probe oligonucleotide comprises a capture probe binding domain; coupling the first probe oligonucleotide and the second probe oligonucleotide, thereby generating a connected probe comprising the capture probe binding domain; and hybridizing the capture probe binding domain of the connected probe to the capture domain. In some instances, the methods further include determining (i) all or part of the sequence of the connected probe, or a complement thereof, and (ii) all or a part of the sequence of the spatial barcode, or a complement thereof. In some instances, the methods further include using the determined sequence of (i), and (ii) to analyze the different analyte in the biological sample. In some instances, the releasing step further releases the connected probe from the different analyte.

In some instances, the different analyte is RNA. In some instances, the different analyte is mRNA.

In some instances, the capture probe comprises a poly(T) sequence. In some instances, the capture probe comprises a sequence specific to the capture handle sequence. In some instances, the capture probe further comprises one or more functional domains, a unique molecular identifier (UMI), a cleavage domain, and combinations thereof.

In some instances, the analyte binding moiety is an antibody. In some instances, the analyte capture agent comprises a linker. In some instances, the linker is a cleavable linker. In some instances, the cleavable linker is a photo-cleavable linker, a UV-cleavable linker, or an enzyme cleavable linker.

In some instances, the biological sample is a tissue sample. In some instances, the tissue sample is a solid tissue sample. In some instances, the solid tissue sample is a tissue section. In some instances, the tissue sample is a fixed tissue sample. In some instances, the fixed tissue sample is a formalin fixed paraffin embedded (FFPE) tissue sample. In some instances, the FFPE tissue is deparaffinized and decrosslinked prior to step (a). In some instances, the fixed tissue sample is a formalin fixed paraffin embedded cell pellet. In some instances, the tissue sample is a fresh frozen tissue sample.

In some instances, the tissue sample is fixed and stained prior to step (a).

In some instances, the methods further include analyzing a second analyte in a second biological sample on a third substrate. In some instances, the analyzing the second analyte comprises: hybridizing a third probe oligonucleotide and a fourth probe oligonucleotide to the second analyte, wherein the third probe oligonucleotide and the fourth probe oligonucleotide each comprise a sequence that is substantially complementary to adjacent sequences of the second analyte, and wherein the fourth probe oligonucleotide comprises a second capture probe binding domain; coupling the third probe oligonucleotide and the fourth probe oligonucleotide, thereby generating a second connected probe; aligning the third substrate with the second substrate comprising the array, such that at least a portion of the second biological sample is aligned with at least a portion of the array; when the second biological sample is aligned with at least a portion of the array, (i) releasing the second connected probe from the second analyte and (ii) migrating the second connected probe from the second biological sample to the array; and hybridizing the second connected probe to the capture domain.

In some instances, the second analyte is RNA. In some instances, the RNA is mRNA.

In some instances, analyzing a second analyte in a second biological sample on a third substrate comprises: contacting the second biological sample with a plurality of second analyte capture agents, wherein a second analyte capture agent of the plurality of second analyte capture agents comprises a second analyte binding moiety and a second capture agent barcode domain, wherein the second analyte binding moiety specifically binds to the second analyte, and wherein the second capture agent barcode domain comprises a second analyte binding moiety barcode and a second capture handle sequence; aligning the third substrate with a second substrate comprising an array, such that at least a portion of the second biological sample is aligned with at least a portion of the array; when the second biological sample is aligned with at least a portion of the array, (i) releasing the second capture agent barcode domain from the second analyte and (ii) migrating the second capture agent barcode domain from the second biological sample to the array; and coupling the second capture handle sequence to the capture domain.

In some instances, the second analyte is a protein analyte. In some instances, the protein analyte is an extracellular protein. In some instances, the protein analyte is an intracellular protein.

In some instances, the methods further include determining (i) all or a part of the sequence of the connected probe, or a complement thereof, and (ii) all or a part of the sequence of the spatial barcode, or a complement thereof, optionally wherein the method further comprises using the determined sequence of (i) and (ii) to determine the location and abundance of the analyte in the biological sample.

In some instances, the second biological sample is a tissue sample, optionally wherein the tissue sample is a solid tissue sample. In some instances, the tissue sample is a tissue section. In some instances, the tissue sample is a fixed tissue sample. In some instances, the fixed tissue sample is a formalin fixed paraffin embedded (FFPE) tissue sample. In some instances, the FFPE tissue is deparaffinized and decrosslinked. In some instances, the fixed tissue sample is a formalin fixed paraffin embedded cell pellet. In some instances, the tissue sample is a fresh tissue sample or a frozen tissue sample. In some instances, the tissue sample is fixed and stained.

In some instances, the methods disclosed herein further include analyzing: a third analyte in a third biological sample on a fourth substrate; a fourth analyte in a fourth biological sample on a fifth substrate; a fifth analyte or more in a fifth biological sample or more on a sixth substrate or more.

Also disclosed herein is a system or a kit for analyzing an analyte in a biological sample. In some instance, the system or the kit includes (a) a support device configured to retain a first substrate and a second substrate, wherein the biological sample is placed on the first substrate, and wherein the second substrate comprises a plurality of capture probes, wherein a capture probe of the plurality of capture probes comprises: (i) a spatial barcode and (ii) a capture domain; (b) (b1) a first probe oligonucleotide and a second probe oligonucleotide, wherein the first probe oligonucleotide and the second probe oligonucleotide each comprise a sequence that is substantially complementary to adjacent sequences of the analyte, wherein the second probe oligonucleotide comprises a capture probe binding domain, and wherein the first probe oligonucleotide and the second probe oligonucleotide are capable of being ligated together to form a connected probe; or (b2) a plurality of analyte capture agents, wherein an analyte capture agent of the plurality of analyte capture agents comprises an analyte binding moiety and a capture agent barcode domain, wherein the analyte binding moiety specifically binds to the analyte, and wherein the capture agent barcode domain comprises an analyte binding moiety barcode and an capture handle sequence; (c) a reagent medium comprising a permeabilization agent and optionally an agent for releasing the connected probe; and (d) instructions for performing any one of the methods disclosed herein. In some instances, the permeabilization agent is pepsin or proteinase K. In some instances, the agent for releasing the connected probe is an RNAse, optionally wherein the RNAse is RNase A, RNase C, RNase H, or RNase I. In some instances, the system or the kit further comprises an alignment mechanism on the support device to align the first substrate and the second substrate. In some instances, the alignment mechanism comprises a linear actuator, wherein the first substrate comprises a first member and the second substrate comprises a second member, and optionally wherein: the linear actuator is configured to move the second member along an axis orthogonal to the plane or the first member and/or the second member, and/or the linear actuator is configured to move the first member along an axis orthogonal to the plane of the first member and/or the second member, and/or the linear actuator is configured to move the first member, the second member, or both the first member and the second member at a velocity of at least 0.1 mm/sec, and/or the linear actuator is configured to move the first member, the second member, or both the first member and the second member with an amount of force of at least 0.1 lbs.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 10A shows a schematic of an example analytical workflow in which electrophoretic migration of analytes is performed after permeabilization.

FIG. 10B shows a schematic of an example analytical workflow in which electrophoretic migration of analytes and permeabilization are performed simultaneously.

FIG. 11A shows an example perpendicular, single slide configuration for use during electrophoresis.

FIG. 11B shows an example parallel, single slide configuration for use during electrophoresis FIG. 11C shows an example multi-slide configuration for use during electrophoresis.

FIG. 17A shows an exemplary schematic illustrating the use of an RNase cleavable linker to release a capture agent barcode domain from an analyte binding moiety of an analyte capture agent.

FIG. 17B shows an exemplary schematic illustrating the use of a UV cleavable linker to release a capture agent barcode domain from an analyte binding moiety of an analyte capture agent.

FIG. 19A shows an exemplary workflow of spatial analysis assays using fresh frozen tissue samples.

FIG. 19B shows an exemplary workflow of spatial analysis assays using formalin-fixation and paraffin-embedded (FFPE) tissue samples.

FIG. 20 shows a table providing data for multiplexed transfer of analytes from multiple biological samples.

FIG. 24 shows a table providing data from an experiment comparing a non-sandwich control and a sandwich configuration permeabilization condition.

FIG. 27A shows heat maps and clustering images of human brain comparing a non-sandwich control and a sandwich configuration condition.

FIG. 27B shows heat maps and clustering images of human breast comparing a non-sandwich control and a sandwich configuration condition.

FIG. 28A shows an exemplary image of spatially-resolved information of gene expression of protein tyrosine phosphatase receptor type C (Ptprc) RNA using ligated probes in FFPE mouse spleen tissue under sandwich configuration conditions.

FIG. 28B shows an exemplary image of spatially-resolved information of protein expression of CD45R using analyte capture agents in FFPE mouse spleen tissue under sandwich configuration conditions.

FIG. 28C shows an exemplary image of spatially-resolved information of gene expression of Ptprc RNA using ligated probes in FFPE spleen tissue under non-sandwich configuration control conditions.

FIG. 28D shows an exemplary image of spatially-resolved information of protein expression of CD45R using analyte capture agents in FFPE mouse spleen tissue under non-sandwich configuration control conditions.

FIG. 29A shows an exemplary image of spatially-resolved information of gene expression of tyrosine hydroxylase (Th) RNA using ligated probes in FFPE mouse brain tissue under sandwich configuration conditions.

FIG. 29B shows an exemplary image of spatially-resolved information of protein expression of tyrosine hydroxylase protein (TH) using analyte capture agents in FFPE mouse brain tissue under sandwich configuration conditions.

FIG. 29C shows an exemplary image of spatially-resolved information of gene expression of Th RNA using ligated probes in FFPE mouse brain tissue under non-sandwich configuration control conditions.

FIG. 29D shows an exemplary image of spatially-resolved information of protein expression of TH using analyte capture agents in FFPE mouse brain tissue under non-sandwich configuration control conditions.

FIG. 30C shows an exemplary image of spatially-resolved information of gene expression of Ter119 RNA using ligated probes in FFPE mouse embryo torso tissue under non-sandwich configuration conditions.

FIG. 30D shows an exemplary image of spatially-resolved information of protein expression of Ter119 using analyte capture agents in FFPE mouse embryo torso tissue under non-sandwich configuration conditions.

FIG. 31C shows an exemplary image of spatially-resolved information of gene expression of Ter119 RNA using ligated probes in FFPE mouse embryo head and upper torso tissue under non-sandwich configuration conditions.

FIG. 31D shows an exemplary image of spatially-resolved information of protein expression of Ter119 using analyte capture agents in FFPE mouse embryo head and upper torso tissue under non-sandwich configuration conditions.

FIGS. 32A, 33A, 34A, 35A, and 36A show exemplary images of spatially-resolved information of gene expression of Mpped1 (FIG. 32A), Tnnc1 (FIG. 33A), Fgf15 (FIG. 34A), Epyc (FIG. 35A), and Serpina1e (FIG. 36A) RNA using ligated probes in FFPE mouse embryo head and upper torso tissue using sandwich configuration conditions.

FIGS. 32B, 33B, 34B, 35B, and 36B show exemplary images of spatially-resolved information of protein expression of Mpped1 (FIG. 32B), Tnnc1 (FIG. 33B), Fgf15 (FIG. 34B), Epyc (FIG. 35B), and Serpina1e (FIG. 36B) using analyte capture agents in FFPE mouse embryo head and upper torso tissue under sandwich configuration conditions.

FIGS. 32C, 33C, 34C, 35C, and 36C show exemplary images of spatially-resolved information of gene expression of Mpped1 (FIG. 32C), Tnnc1 (FIG. 33C), Fgf15 (FIG. 34C), Epyc (FIG. 35C), and Serpina1e (FIG. 36C) RNA using ligated probes in FFPE mouse embryo torso tissue under sandwich configuration conditions.

FIGS. 32D, 33D, 34D, 35D, and 36D show exemplary images of spatially-resolved information of gene expression of Mpped1 (FIG. 32D), Tnnc1 (FIG. 33D), Fgf15 (FIG. 34D), Epyc (FIG. 35D), and Serpina1e (FIG. 36D) RNA using ligated probes in FFPE mouse embryo head and upper torso tissue under non-sandwich configuration conditions.

FIGS. 32E, 33E, 34E, 35E, and 36E show exemplary images of spatially-resolved information of protein expression of Mpped1 (FIG. 32E), Tnnc1 (FIG. 33E), Fgf15 (FIG. 34E), Epyc (FIG. 35E), and Serpina1e (FIG. 36E) using analyte capture agents in FFPE mouse embryo head and upper torso tissue under non-sandwich configuration conditions.

FIGS. 32F, 33F, 34F, 35F, and 36F show exemplary images of spatially-resolved information of gene expression of Mpped1 (FIG. 32F), Tnnc1 (FIG. 33F), Fgf15 (FIG. 34F), Epyc (FIG. 35F), and Serpina1e (FIG. 36F) RNA using ligated probes in FFPE mouse embryo torso tissue under non-sandwich configuration conditions.

FIGS. 32G, 33G, 34G, 35G, and 36G show exemplary images of spatially-resolved information of protein expression of Mpped1 (FIG. 32G), Tnnc1 (FIG. 33G), Fgf15 (FIG. 34G), Epyc (FIG. 35G), and Serpina1e (FIG. 36G) using analyte capture agents in FFPE mouse embryo torso tissue under non-sandwich configuration conditions.

FIGS. 32H, 33H, 34H, 35H, and 36H show exemplary images of spatially-resolved information of gene expression of Mpped1 (FIG. 32H), Tnnc1 (FIG. 33H), Fgf15 (FIG. 34H), Epyc (FIG. 35H), and Serpina1e (FIG. 36H) RNA using ligated probes in FFPE mouse embryo head and upper torso tissue under non-sandwich configuration conditions in which only RNA was detected.

FIGS. 32I, 33I, 34I, 35I, and 36I show exemplary images of spatially-resolved information of gene expression of Mpped1 (FIG. 32I), Tnnc1 (FIG. 33I), Fgf15 (FIG. 34I), Epyc (FIG. 35I), and Serpina1e (FIG. 36I) RNA using ligated probes in FFPE mouse embryo torso tissue under non-sandwich configuration conditions in which only RNA was detected.

FIG. 38A shows an exemplary sandwiching process where a first substrate, including a biological sample, and a second substrate are brought into proximity with one another.

FIG. 38B shows a fully formed sandwich configuration creating a chamber formed from the one or more spacers, the first substrate, and the second substrate.

DETAILED DESCRIPTION

I. Introduction

Figure 1:
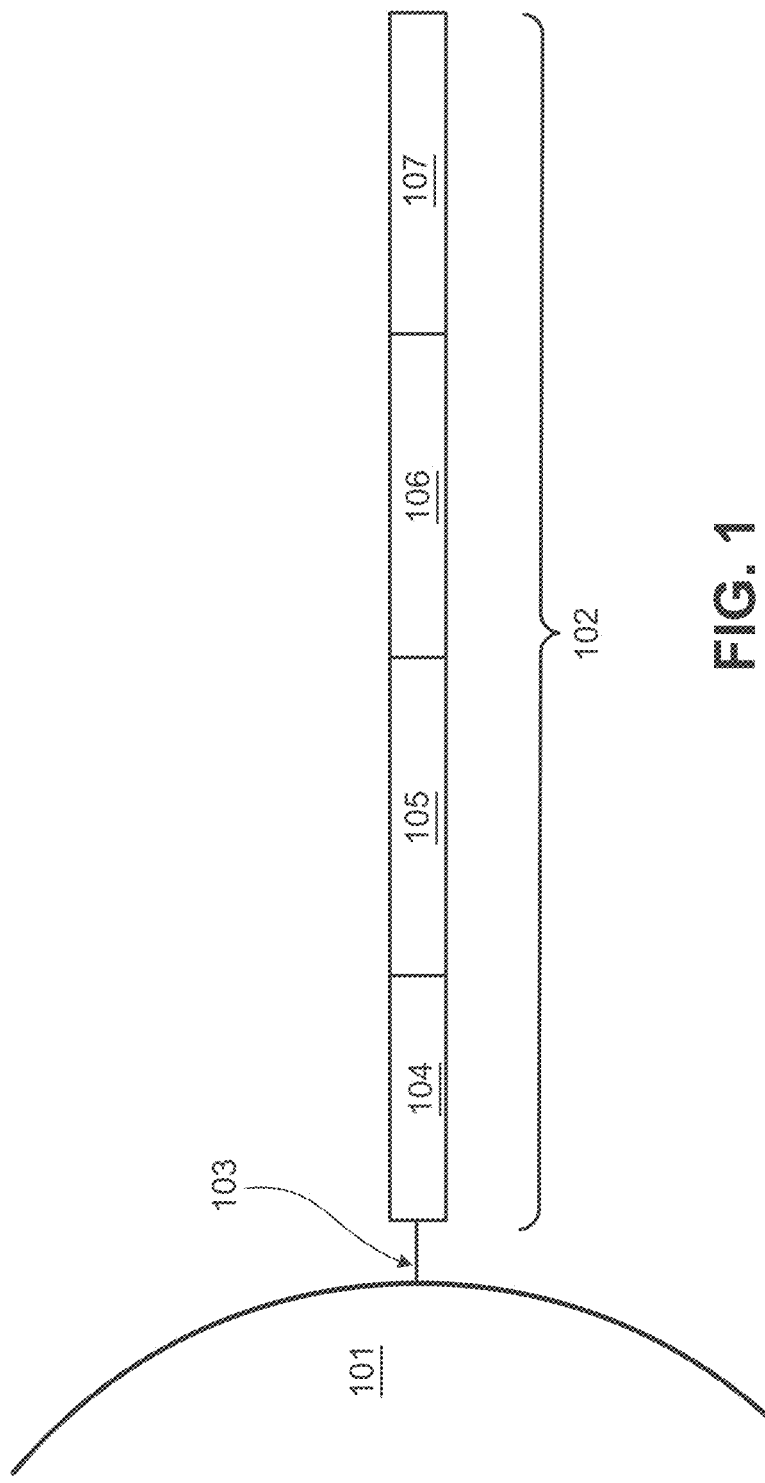
FIG. 1 is a schematic diagram showing an example of a barcoded capture probe, as described herein.

Spatial analysis methodologies, systems, and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodriques et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a connected probe (e.g., a ligation product) or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)).

In some instance, the capture domain is designed to detect one or more specific analytes of interest. For example, a capture domain can be designed so that it comprises a sequence that is complementary or substantially complementary to one analyte of interest. Thus, the presence of a single analyte can be detected. Alternatively, the capture domain can be designed so that it comprises a sequence that is complementary or substantially complementary to a conserved region of multiple related analytes. In some instances, the multiple related analytes are analytes that function in the same or similar cellular pathways or that have conserved homology and/or function. The design of the capture probe can be determined based on the intent of the user and can be any sequence that can be used to detect an analyte of interest. In some embodiments, the capture domain sequence can therefore be random, semi-random, defined or combinations thereof, depending on the target analyte(s) of interest.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

Figure 2:
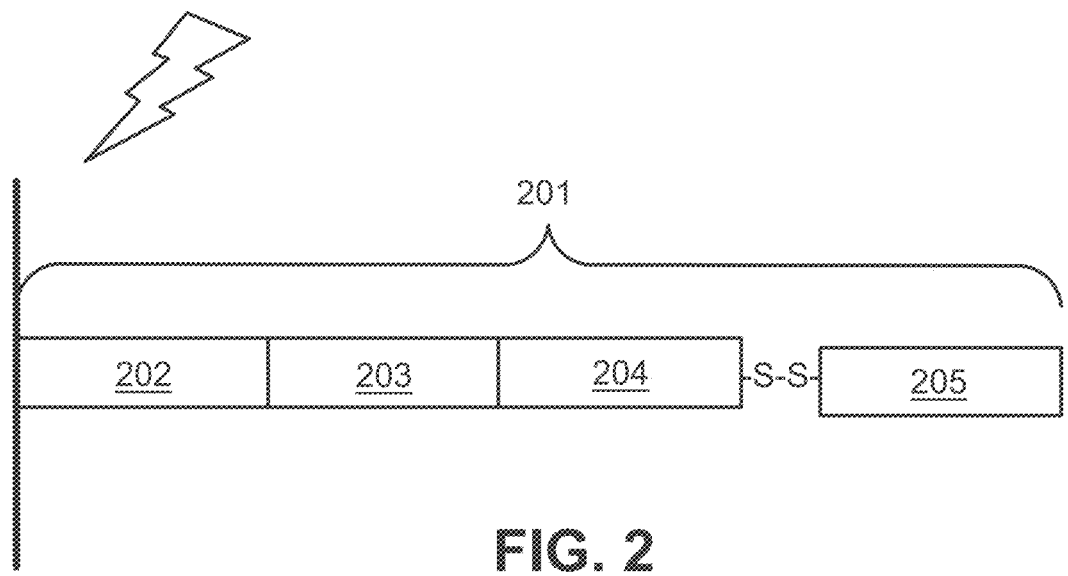
FIG. 2 is a schematic illustrating a cleavable capture probe, wherein the cleaved capture probe can enter into a non-permeabilized cell and bind to target analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain.

Figure 3:
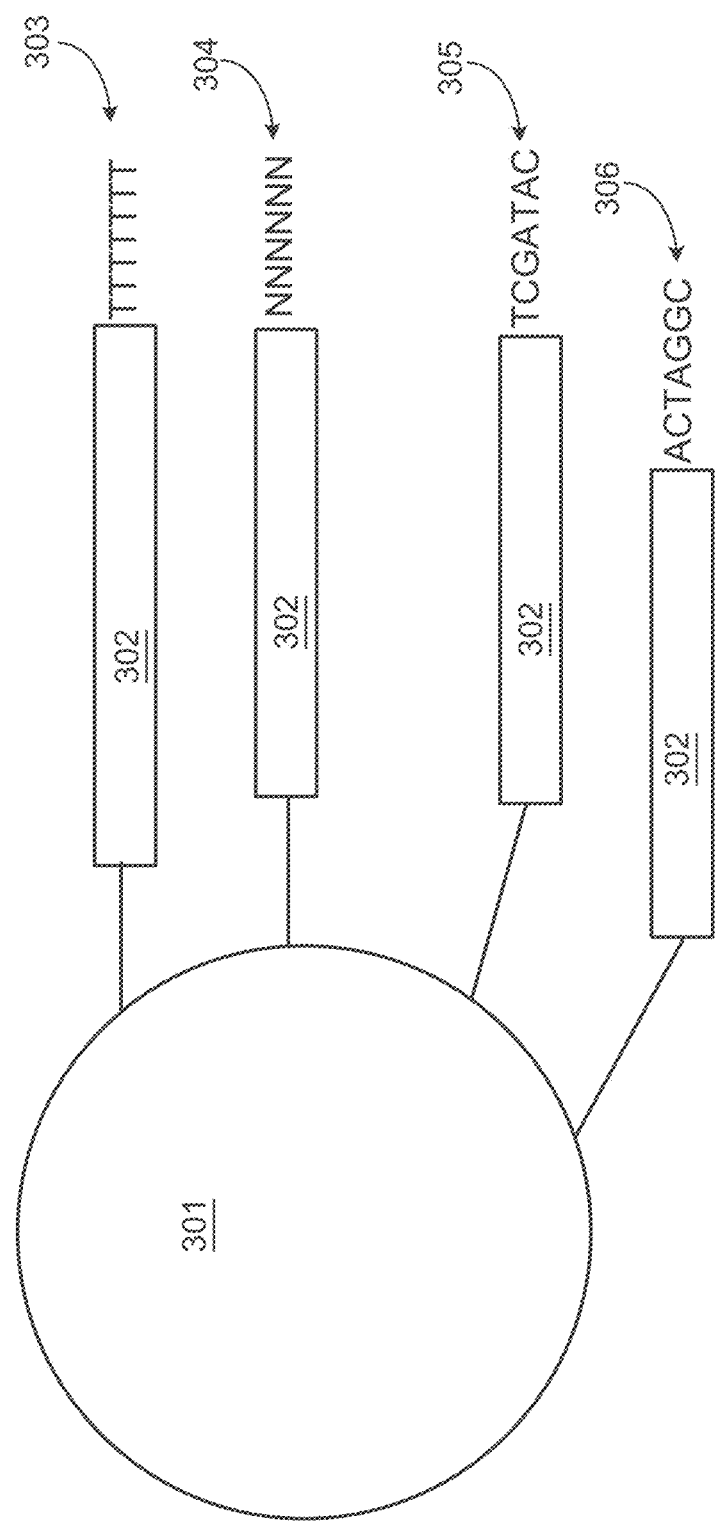
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA target analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) a capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent.

Figure 4:
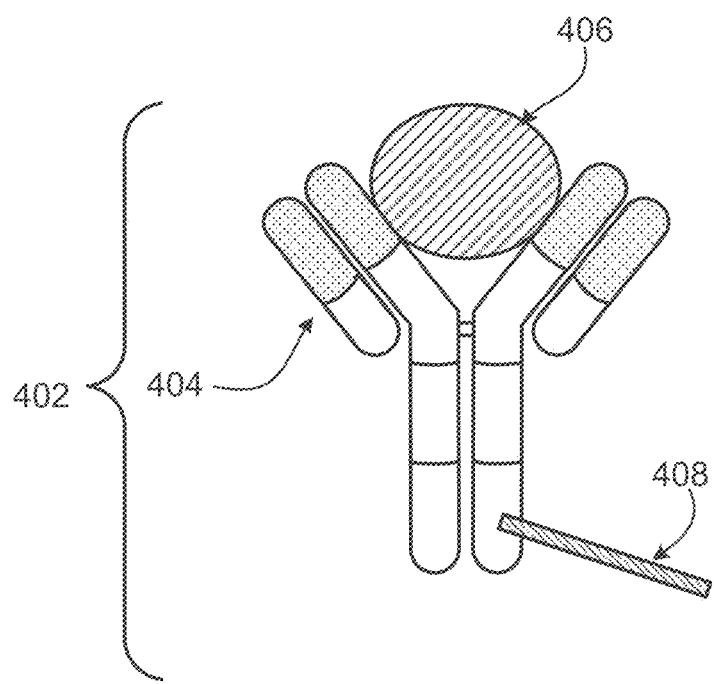
FIG. 4 is a schematic diagram of an exemplary analyte capture agent.

FIG. 4 is a schematic diagram of an exemplary analyte capture agent 402 comprised of an analyte-binding moiety 404 and an analyte-binding moiety barcode domain 408. The exemplary analyte-binding moiety 404 is a molecule capable of binding to an analyte 406 and the analyte capture agent is capable of interacting with a spatially-barcoded capture probe. The analyte-binding moiety can bind to the analyte 406 with high affinity and/or with high specificity. The analyte capture agent can include an analyte-binding moiety barcode domain 408, a nucleotide sequence (e.g., an oligonucleotide), which can hybridize to at least a portion or an entirety of a capture domain of a capture probe. The analyte-binding moiety barcode domain 408 can comprise an analyte binding moiety barcode and a capture handle sequence described herein. The analyte-binding moiety 404 can include a polypeptide and/or an aptamer. The analyte-binding moiety 404 can include an antibody or antibody fragment (e.g., an antigen-binding fragment).

Figure 5:
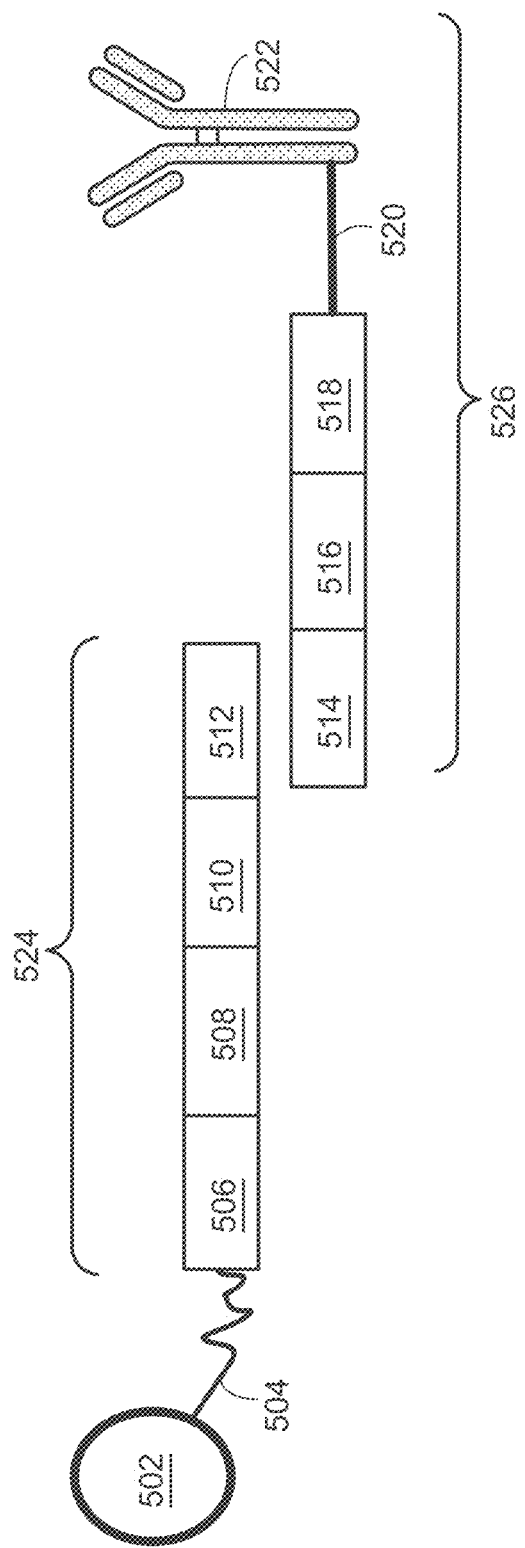
FIG. 5 is a schematic diagram depicting an exemplary interaction between a feature-immobilized capture probe 524 and an analyte capture agent 526.

FIG. 5 is a schematic diagram depicting an exemplary interaction between a feature-immobilized capture probe 524 and an analyte capture agent 526. The feature-immobilized capture probe 524 can include a spatial barcode 508 as well as functional sequences 506 and UMI 510, as described elsewhere herein. The capture probe can also include a capture domain 512 that is capable of binding to an analyte capture agent 526. The analyte capture agent 526 can include a functional sequence 518, analyte binding moiety barcode 516, and a capture handle sequence 514 that is capable of binding to the capture domain 512 of the capture probe 524. The analyte capture agent can also include a linker 520 that allows the capture agent barcode domain 516 to couple to the analyte binding moiety 522.

Figure 6A:
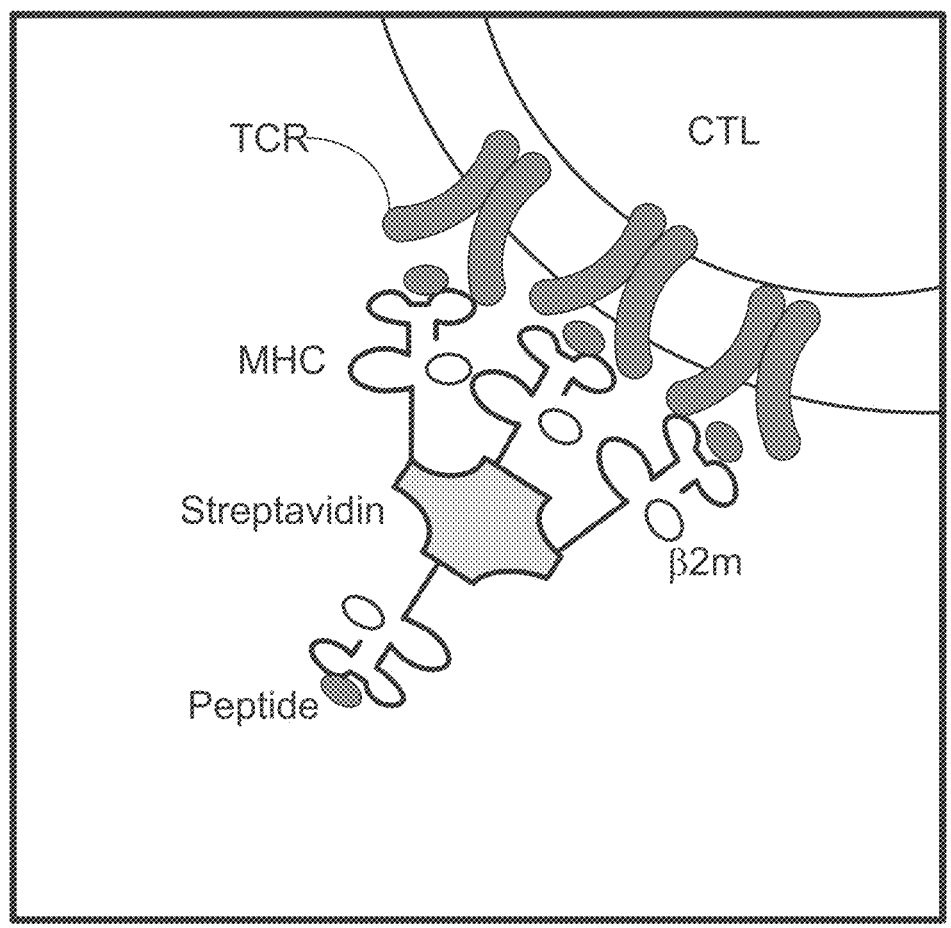
FIGS. 6A, 6B, and 6C are schematics illustrating how streptavidin cell tags can be utilized in an array-based system to produce a spatially-barcoded cells or cellular contents.
Figure 6B:
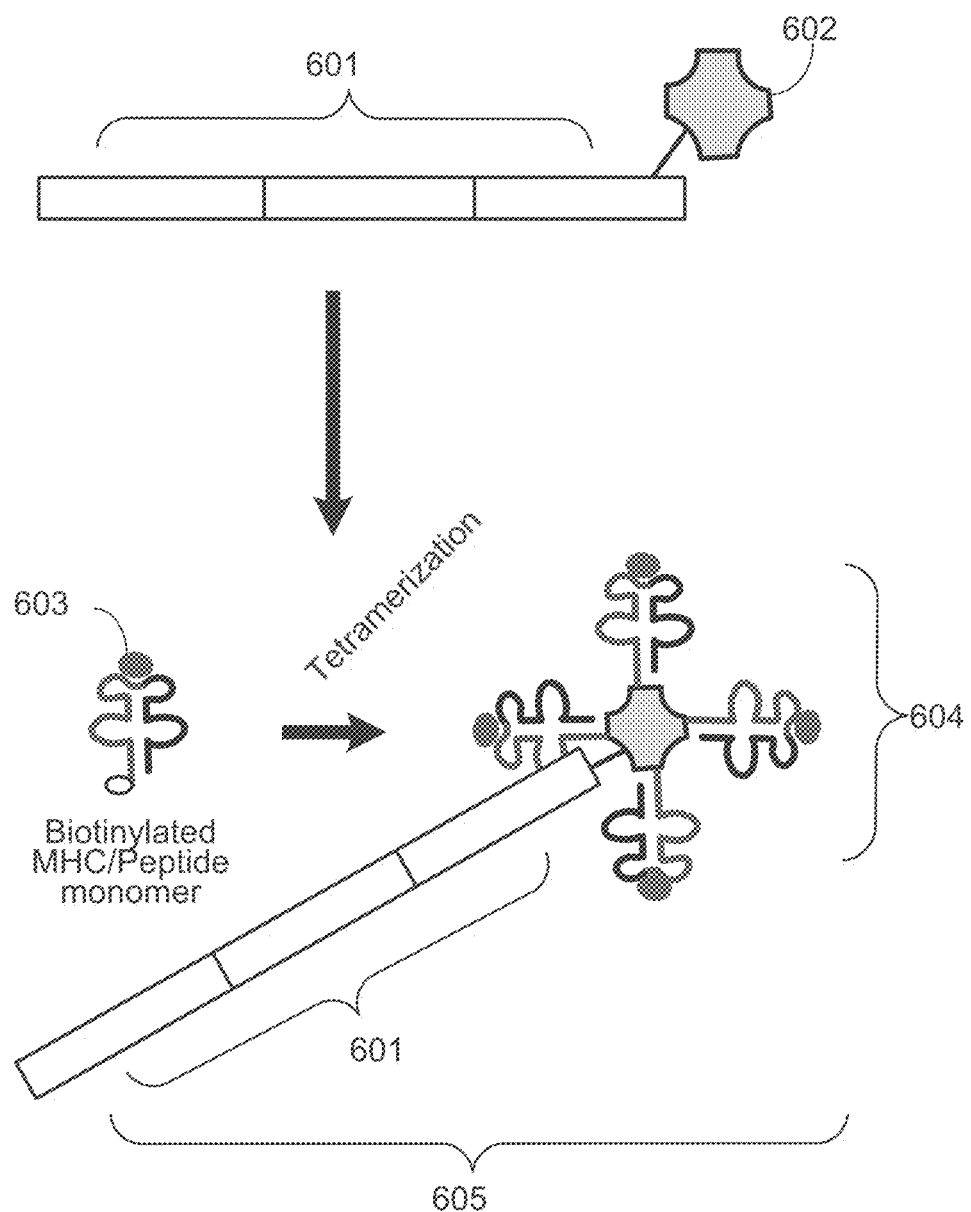
Figure 6C:
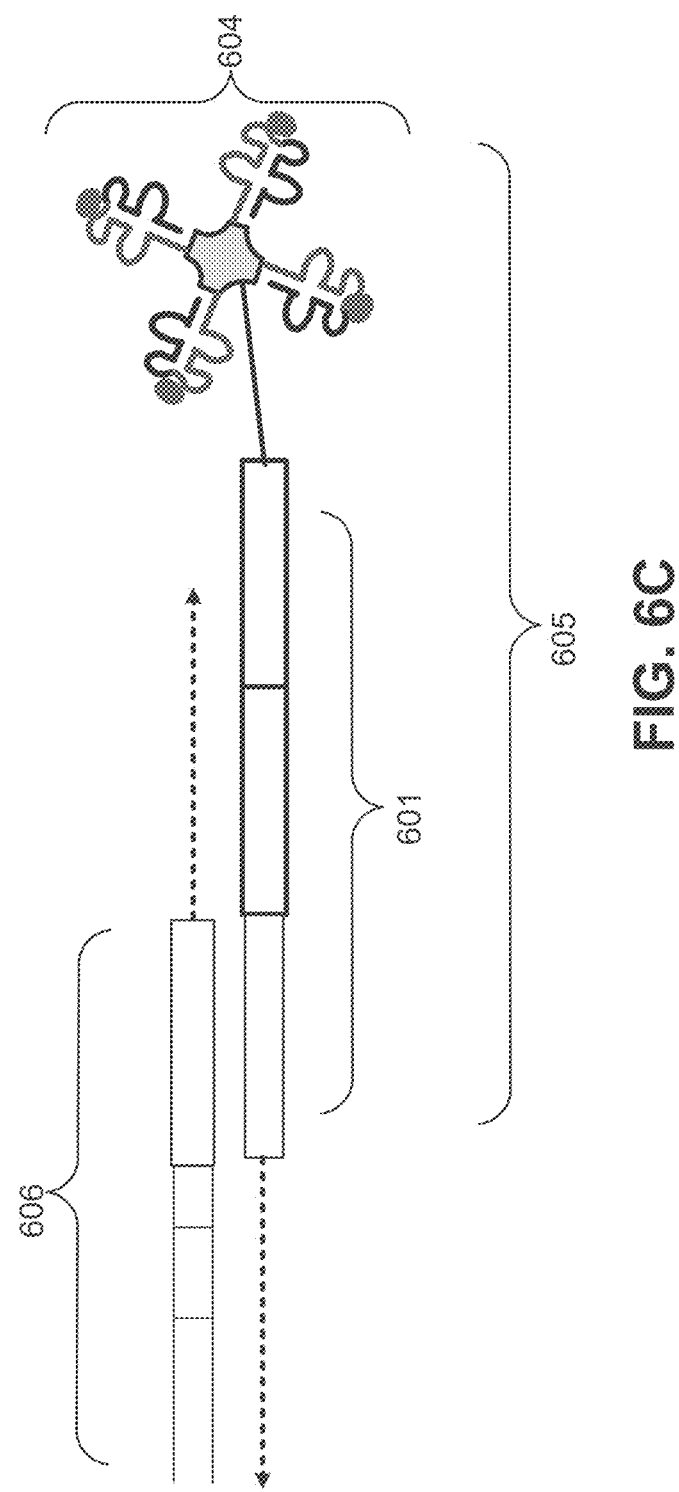
Figure 7:
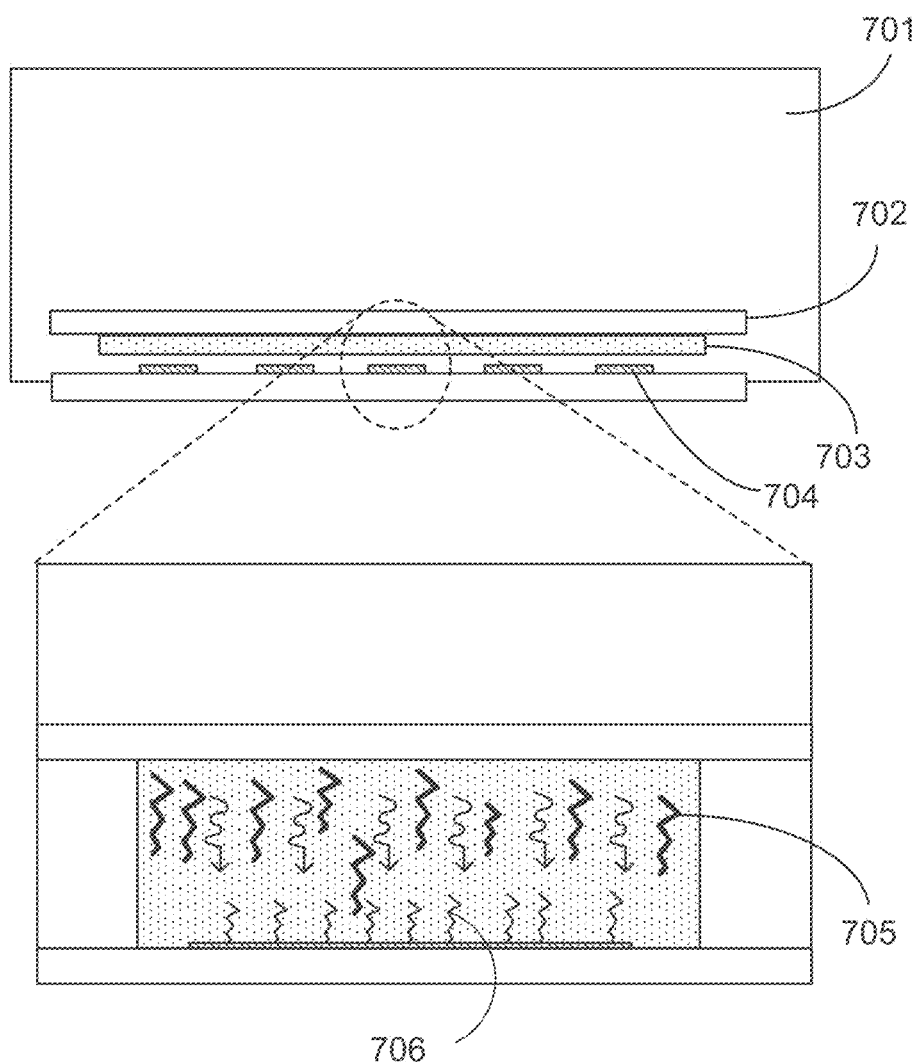
FIG. 7 is a schematic illustrating a side view of a diffusion-resistant medium, e.g., a lid.
Figure 8A:
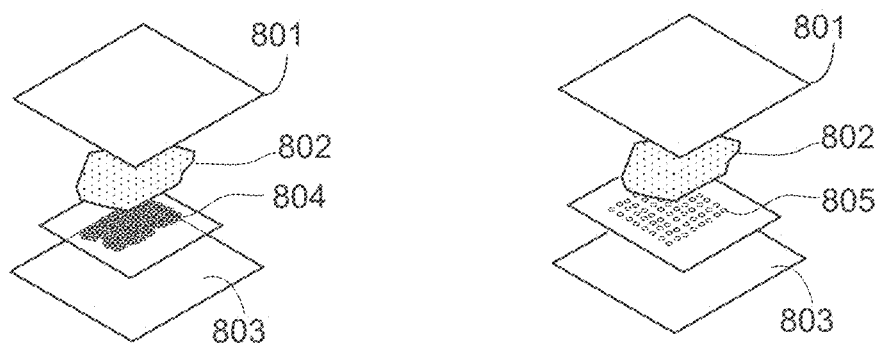
FIGS. 8A and 8B are schematics illustrating expanded FIG. 8A and side views FIG. 8B of an electrophoretic transfer system configured to direct transcript analytes toward a spatially-barcoded capture probe array.
Figure 8B:
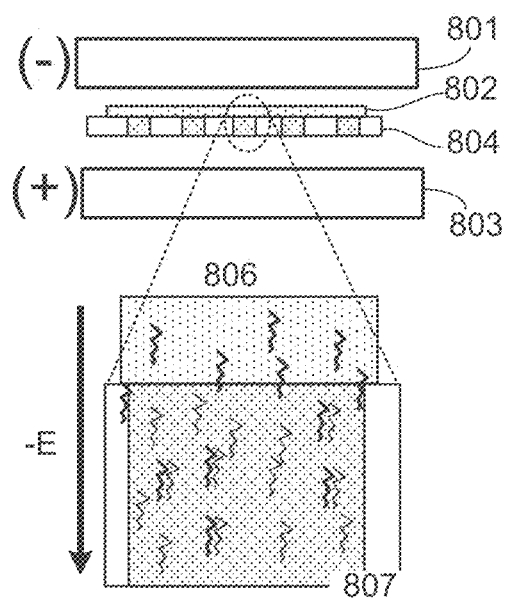
Figure 9:
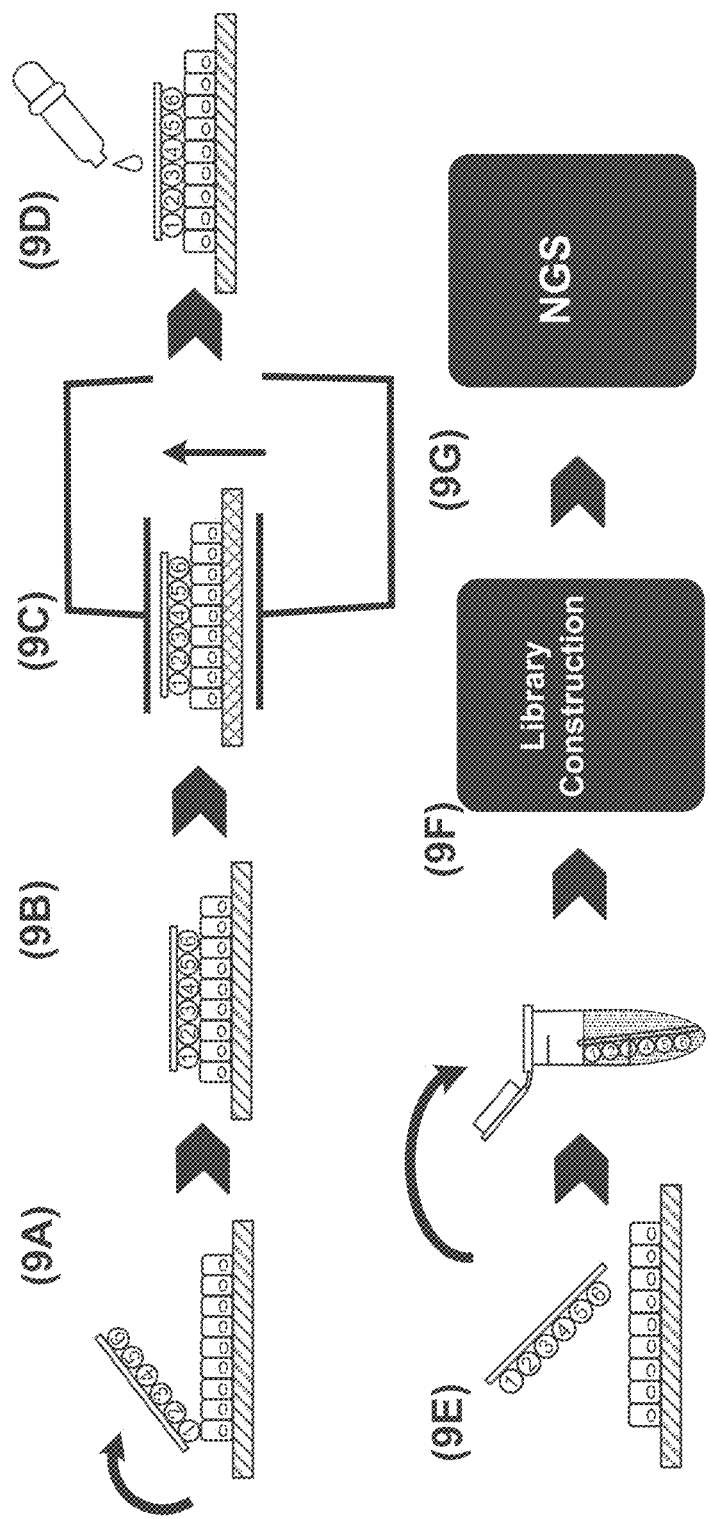
FIG. 9 is a schematic illustrating an exemplary workflow protocol utilizing an electrophoretic transfer system.

FIGS. 6A, 6B, and 6C are schematics illustrating how streptavidin cell tags can be utilized in an array-based system to produce a spatially-barcoded cell or cellular contents. For example, as shown in FIG. 6A, peptide-bound major histocompatibility complex (MHC) can be individually associated with biotin (β2m) and bound to a streptavidin moiety such that the streptavidin moiety comprises multiple pMHC moieties. Each of these moieties can bind to a TCR such that the streptavidin binds to a target T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 6B, a capture agent barcode domain 601 can be modified with streptavidin 602 and contacted with multiple molecules of biotinylated MHC 603 such that the biotinylated MHC 603 molecules are coupled with the streptavidin conjugated capture agent barcode domain 601. The result is a barcoded MHC multimer complex 605. As shown in FIG. 6B, the capture agent barcode domain sequence 601 can identify the MHC as its associated label and also includes optional functional sequences such as sequences for hybridization with other oligonucleotides. As shown in FIG. 6C, one example oligonucleotide is capture probe 606 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 606 may at first be associated with a feature (e.g., a gel bead) and released from the feature. In other embodiments, capture probe 606 can hybridize with a capture agent barcode domain 601 of the MHC-oligonucleotide complex 605. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 606 or capture agent barcode domain 601. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 606 spatial barcode sequence may be used to identify a feature and the sequence derived from spatial barcode sequence on the capture agent barcode domain 601 may be used to identify the particular peptide MHC complex 604 bound on the surface of the cell (e.g., when using MHC-peptide libraries for screening immune cells or immune cell populations).

Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a connected probe (e.g., a ligation product) or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form a connected probe (e.g., a ligation product) with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a connected probe (e.g., a ligation product). In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the connected probe (e.g., a ligation product) is released from the analyte. In some instances, the connected probe (e.g., a ligation product) is released using an endonuclease (e.g., RNase A, RNase C, RNase H, or RNase I). The released connected probe (e.g., a ligation product) can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

The sandwich process is described in PCT Patent Application Publication No. WO 2020/123320, which is incorporated by reference in its entirety.

II. Methods, Compositions, Devices, and Systems for Capturing Analytes and Derivatives Thereof (a) Introduction Provided herein are methods, devices, compositions, and systems for analyzing the location and abundance of a nucleic acid or protein analyte in a biological sample. In some instances, the methods include aligning (i.e., sandwiching) a first substrate having the biological sample with a second substrate that includes a plurality of capture probes, thereby "sandwiching" the biological sample between the two substrates. Upon interaction of the biological sample with the substrate having a plurality of probes (in either instance), the location and abundance of a nucleic acid or protein analyte in a biological sample can be determined, as provided herein. This methods includes an advantage in that steps provided herein prior to analyte or analyte-derived molecule by the capture probe, most-if not all-steps can be performed on a substrate that does not have capture probes, thereby providing a method that is cost effective.

The methods and systems provided herein can be applied to an analyte or an analyte-derived molecule(s). As used herein, an analyte derived molecule includes, without limitation, a connected probe (e.g., a ligation product) from an RNA-templated ligation (RTL) assay, a product of reverse transcription (e.g., an extended capture probe), and an analyte binding moiety barcode (e.g., a binding moiety barcode that identifies that analyte binding moiety (e.g., an antibody)). In some embodiments, the analyte or analyte derived molecules comprise RNA and/or DNA. In some embodiments, the analyte or analyte derived molecules comprise one or more proteins.

In some instances, the methods, devices, compositions, and systems disclosed herein provide efficient release of an analyte or analyte derived molecule from a biological sample so that it can be easily captured or detected using methods disclosed herein.

In some instances, the methods, devices, compositions, and systems disclosed herein allow for detection of analytes or analyte derived molecules from different biological samples using a single array comprising a plurality of capture probes. As such, in some instances, the methods, devices, compositions, and systems allow for serial capture of analytes or analyte derived molecules from multiple samples. The analytes or analyte derived molecules can then be demultiplexed using biological-sample-specific index sequences to identify it biological sample origin.

Embodiments of the methods, devices, compositions, and systems disclosed herein are provided below.

(A) Exemplary Biological Samples

The biological sample as used herein can be any suitable biological sample described herein or known in the art. In some embodiments, the biological sample is a tissue. In some embodiments, the tissue sample is a solid tissue sample. In some embodiments, the biological sample is a tissue section. In some embodiments, the tissue is flash-frozen and sectioned. Any suitable methods described herein or known in the art can be used to flash-freeze and section the tissue sample. In some embodiments, the biological sample, e.g., the tissue, is flash-frozen using liquid nitrogen before sectioning. In some embodiments, the sectioning is performed using cryosectioning. In some embodiments, the methods further comprises a thawing step, after the cryosectioning. In some embodiments, the biological sample, e.g., the tissue sample is fixed, for example in methanol, acetone, PFA or is formalin-fixed and paraffin-embedded (FFPE). In some embodiments, the biological sample comprises intact cells. In some embodiments, the biological sample is a cell pellet, e.g., a fixed cell pellet, e.g., an FFPE cell pellet. FFPE samples are used in some instances in the RTL methods disclosed herein. A limitation of direct RNA capture for fixed samples is that the RNA integrity of fixed (e.g., FFPE) samples can be lower than a fresh sample, thereby making it more difficult to capture RNA directly, e.g., by capture of a common sequence such as a poly(A) tail of an mRNA molecule. However, by utilizing RTL probe oligonucleotides that hybridize to RNA target sequences in the transcriptome, one can avoid a requirement for RNA analytes to have both a poly(A) tail and target sequences intact. Accordingly, RTL probes can be utilized to beneficially improve capture and spatial analysis of fixed samples.

The biological sample, e.g., tissue sample, can be stained, and imaged prior, during, and/or after each step of the methods described herein. Any of the methods described herein or known in the art can be used to stain and/or image the biological sample. In some embodiments, the imaging occurs prior to deaminating the sample. In some embodiments, the biological sample is stained using an H&E staining method. In some embodiments, the tissue sample is stained and imaged for about 10 minutes to about 2 hours (or any of the subranges of this range described herein). Additional time may be needed for staining and imaging of different types of biological samples.

The tissue sample can be obtained from any suitable location in a tissue or organ of a subject, e.g., a human subject. In some instances, the sample is a human sample. In some instances, the sample is a human breast tissue sample. In some instances, the sample is a human brain tissue sample. In some embodiments, the sample is an embryo sample. The embryo sample can be a non-human embryo sample. In some instances, the sample is a mouse embryo sample.

(B) Exemplary First and Second Substrates

In some instances, the biological sample is placed (e.g., mounted or otherwise immobilized) on a first substrate. The first substrate can be any solid or semi-solid support upon which a biological sample can be mounted. In some instances, the first substrate is a slide. In some instances, the slide is a glass slide. In some embodiments, the substrate is made of glass, silicon, paper, hydrogel, polymer monoliths, or other material known in the art. In some embodiments, the first substrate is comprised of an inert material or matrix (e.g., glass slides) that has been functionalized by, for example, treating the substrate with a material comprising reactive groups which facilitate mounting of the biological sample.

In some embodiments, the first substrate does not comprise a plurality (e.g., array) of capture probes, each comprising a spatial barcode.

A substrate, e.g., a first substrate and/or a second substrate, can generally have any suitable form or format. For example, a substrate can be flat, curved, e.g., convexly or concavely curved. For example, a first substrate can be curved towards the area where the interaction between a biological sample, e.g., tissue sample, and a first substrate takes place. In some embodiments, a substrate is flat, e.g., planar, chip, or slide. A substrate can contain one or more patterned surfaces within the first substrate (e.g., channels, wells, projections, ridges, divots, etc.).

A substrate, e.g., a first substrate and/or second substrate, can be of any desired shape. For example, a substrate can be typically a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or cross-table). In some embodiments wherein a substrate structure is flat, the substrate structure can be any appropriate type of support having a flat surface (e.g., a chip or a slide such as a microscope slide).

First and/or second substrates can optionally include various structures such as, but not limited to, projections, ridges, and channels. A substrate can be micropatterned to limit lateral diffusion of analytes (e.g., to improve resolution of the spatial analysis). A substrate modified with such structures can be modified to allow association of analytes, features (e.g., beads), or probes at individual sites. For example, the sites where a substrate is modified with various structures can be contiguous or non-contiguous with other sites.

In some embodiments, the surface of a first and/or second substrate is modified to contain one or more wells, using techniques such as (but not limited to) stamping, microetching, or molding techniques. In some embodiments in which a first and/or second substrate includes one or more wells, the first substrate can be a concavity slide or cavity slide. For example, wells can be formed by one or more shallow depressions on the surface of the first and/or second substrate. In some embodiments, where a first and/or second substrate includes one or more wells, the wells can be formed by attaching a cassette (e.g., a cassette containing one or more chambers) to a surface of the first substrate structure.

In some embodiments where the first and/or second substrate is modified to contain one or more structures, including but not limited to, wells, projections, ridges, features, or markings, the structures can include physically altered sites. For example, a first and/or second substrate modified with various structures can include physical properties, including, but not limited to, physical configurations, magnetic or compressive forces, chemically functionalized sites, chemically altered sites, and/or electrostatically altered sites. In some embodiments where the first substrate is modified to contain various structures, including but not limited to wells, projections, ridges, features, or markings, the structures are applied in a pattern. Alternatively, the structures can be randomly distributed.

In some embodiments, a first substrate includes one or more markings on its surface, e.g., to provide guidance for aligning at least a portion of the biological sample with a plurality of capture probes on the second substrate during a sandwich process disclosed herein. For example, the first substrate can include a sample area indicator identifying the sample area. In some embodiments, during a sandwiching process described herein the sample area indicator on the first substrate is aligned with an area of the second substrate comprising a plurality of capture probes. In some embodiments, the first and/or second substrate can include a fiducial mark. In some embodiments, the first and/or second substrate does not comprise a fiducial mark. In some embodiments, the first substrate does not comprise a fiducial mark and the second substrate comprises a fiducial mark. Such markings can be made using techniques including, but not limited to, printing, sand-blasting, and depositing on the surface.

In some embodiments, imaging can be performed using one or more fiducial markers, i.e., objects placed in the field of view of an imaging system which appear in the image produced. Fiducial markers are typically used as a point of reference or measurement scale. Fiducial markers can include, but are not limited to, detectable labels such as fluorescent, radioactive, chemiluminescent, and colorimetric labels. The use of fiducial markers to stabilize and orient biological samples is described, for example, in Carter et al., Applied Optics 46:421-427, 2007), the entire contents of which are incorporated herein by reference. In some embodiments, a fiducial marker can be a physical particle (e.g., a nanoparticle, a microsphere, a nanosphere, a bead, a post, or any of the other exemplary physical particles described herein or known in the art).

In some embodiments, a fiducial marker can be present on a first substrate to provide orientation of the biological sample. In some embodiments, a microsphere can be coupled to a first substrate to aid in orientation of the biological sample. In some examples, a microsphere coupled to a first substrate can produce an optical signal (e.g., fluorescence). In some embodiments, a quantum dot can be coupled to the first substrate to aid in the orientation of the biological sample. In some examples, a quantum dot coupled to a first substrate can produce an optical signal.

In some embodiments, a fiducial marker can be an immobilized molecule with which a detectable signal molecule can interact to generate a signal. For example, a marker nucleic acid can be linked or coupled to a chemical moiety capable of fluorescing when subjected to light of a specific wavelength (or range of wavelengths). Although not required, it can be advantageous to use a marker that can be detected using the same conditions (e.g., imaging conditions) used to detect a labelled cDNA.

In some embodiments, a fiducial marker can be randomly placed in the field of view. For example, an oligonucleotide containing a fluorophore can be randomly printed, stamped, synthesized, or attached to a first substrate (e.g., a glass slide) at a random position on the first substrate. A tissue section can be contacted with the first substrate such that the oligonucleotide containing the fluorophore contacts, or is in proximity to, a cell from the tissue section or a component of the cell (e.g., an mRNA or DNA molecule). An image of the first substrate and the tissue section can be obtained, and the position of the fluorophore within the tissue section image can be determined (e.g., by reviewing an optical image of the tissue section overlaid with the fluorophore detection). In some embodiments, fiducial markers can be precisely placed in the field of view (e.g., at known locations on a first substrate). In this instance, a fiducial marker can be stamped, attached, or synthesized on the first substrate and contacted with a biological sample. Typically, an image of the sample and the fiducial marker is taken, and the position of the fiducial marker on the first substrate can be confirmed by viewing the image.

In some embodiments, a fiducial marker can be an immobilized molecule (e.g., a physical particle) attached to the first substrate. For example, a fiducial marker can be a nanoparticle, e.g., a nanorod, a nanowire, a nanocube, a nanopyramid, or a spherical nanoparticle. In some examples, the nanoparticle can be made of a heavy metal (e.g., gold). In some embodiments, the nanoparticle can be made from diamond. In some embodiments, the fiducial marker can be visible by eye.

A wide variety of different first substrates can be used for the foregoing purposes. In general, a first substrate can be any suitable support material. Exemplary first substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene polycarbonate, or combinations thereof.

Among the examples of first substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface the nucleic acid immobilization can be increased. Such an enhancement can permit a relatively more densely packed formation (e.g., provide improved specificity and resolution).

In another example, a first substrate can be a flow cell. Flow cells can be formed of any of the foregoing materials, and can include channels that permit reagents, solvents, features, and analytes to pass through the flow cell. In some embodiments, a hydrogel embedded biological sample is assembled in a flow cell (e.g., the flow cell is utilized to introduce the hydrogel to the biological sample). In some embodiments, a hydrogel embedded biological sample is not assembled in a flow cell. In some embodiments, the hydrogel embedded biological sample can then be prepared and/or isometrically expanded as described herein.

Exemplary substrates similar to the first substrate (e.g., a substrate having no capture probes) and/or the second substrate are described in Section (I) above and in WO 2020/123320, which is hereby incorporated by reference in its entirety.

(b) Capturing Nucleic Acid Analytes Using RNA-Templated Ligation

In some embodiments, the methods, devices, compositions, and systems described herein utilize RNA-templated ligation to detect the analyte. As used herein, spatial "RNA-templated ligation," or "RTL" or simply "templated ligation" is a process wherein individual probe oligonucleotides (e.g., a first probe oligonucleotide, a second probe oligonucleotide) in a probe pair hybridize to adjacent sequences of an analyte (e.g., an RNA molecule) in a biological sample (e.g., a tissue sample). The RTL probe oligonucleotides are then coupled (e.g., ligated) together, thereby creating a connected probe (e.g., a ligation product). RNA-templated ligation is disclosed in PCT Publ. No. WO 2021/133849 A1 and US Publ. No. US 2021/0285046 A1, each of which is incorporated by reference in its entirety.

An advantage to using RTL is that it allows for enhanced detection of analytes (e.g., low expressing analytes) because both probe oligonucleotides must hybridize to the analyte in order for the coupling (e.g., ligating) reaction to occur. As used herein, "coupling" refers to an interaction between two probe oligonucleotides that results in a single connected probe that comprises the two probe oligonucleotides. In some instances, coupling is achieved through ligation. In some instances, coupling is achieved through extension of one probe oligonucleotide to the second probe oligonucleotide followed by ligation. In some instances, coupling is achieved through hybridization (e.g., using a third probe oligonucleotide that hybridized to each of the two probe oligonucleotides) followed by extension of one probe oligonucleotide or gap filling of the sequence between the two probe oligonucleotides using the third probe oligonucleotide as a template.

The connected probe (e.g., ligation product) that results from the coupling (e.g., ligation) of the two probe oligonucleotides can serve as a proxy for the target analyte, as such an analyte derived molecule. Further, it is appreciated that probe oligonucleotide pairs can be designed to cover any gene of interest. For example, a pair of probe oligonucleotides can be designed so that each analyte, e.g., a whole exome, a transcriptome, a genome, can conceivably be detected using a probe oligonucleotide pair.

In some instances, disclosed herein are methods for analyzing an analyte in a biological sample comprising (a) hybridizing a first probe oligonucleotide and a second probe oligonucleotide to the analyte, wherein the first probe oligonucleotide and the second probe oligonucleotide each comprise a sequence that is substantially complementary to adjacent sequences of the analyte, and wherein the second probe oligonucleotide comprises a capture probe binding domain; (b) coupling the first probe oligonucleotide and the second probe oligonucleotide, thereby generating a connected probe (e.g., a ligation product) comprising the capture probe binding domain; (c) contacting the biological sample with a reagent medium comprising a permeabilization agent and an agent for releasing the connected probe (e.g., a ligation product), thereby (i) permeabilizing the biological sample and (ii) releasing the connected probe (e.g., a ligation product) from the analyte; and (d) hybridizing the capture probe binding domain of the connected probe (e.g., a ligation product) to a capture domain of a capture probe, wherein the capture probe comprises: (i) a spatial barcode and (ii) a capture domain.

Also provided herein are methods for analyzing an analyte in a biological sample mounted on a first substrate including (a) hybridizing a first probe oligonucleotide and a second probe oligonucleotide to the analyte, wherein the first probe oligonucleotide and the second probe oligonucleotide each include a sequence that is substantially complementary to adjacent sequences of the analyte, and wherein the second probe oligonucleotide includes a capture probe binding domain; (b) coupling (e.g., ligating) the first probe oligonucleotide and the second probe oligonucleotide, thereby generating a connected probe (e.g., a ligation product) including the capture probe binding domain; (c) aligning the first substrate with a second substrate including an array, such that at least a portion of the biological sample is aligned with at least a portion of the array, wherein the array includes a plurality of capture probes, wherein a capture probe of the plurality of capture probes includes: (i) a spatial barcode and (ii) a capture domain; (d) when the biological sample is aligned with at least a portion of the array, (i) releasing the connected probe (e.g., a ligation product) from the analyte and (ii) passively or actively migrating the connected probe (e.g., a ligation product) from the biological sample to the array; and (e) hybridizing the capture probe binding domain of the connected probe (e.g., a ligation product) to the capture domain.

In some embodiments, the process of transferring the connected probe (e.g., a ligation product) from the first substrate to the second substrate is referred to as a "sandwich" process. The sandwich process is described in PCT Patent Application Publication No. WO 2020/123320, which is incorporated by reference in its entirety. Described herein are methods in which an array with capture probes located on a substrate and a biological sample located on a different substrate, are contacted such that the array is in contact with the biological sample (e.g., the substrates are sandwiched together). In some embodiments, the array and the biological sample can be contacted (e.g., sandwiched), without the aid of a substrate holder. In some embodiments, the array and biological sample substrates can be placed in a substrate holder (e.g., an array alignment device) designed to align the biological sample and the array. For example, the substrate holder can have placeholders for two substrates. In some embodiments, an array including capture probes can be positioned on one side of the substrate holder (e.g., in a first substrate placeholder). In some embodiments, a biological sample can be placed on the adjacent side of the substrate holder in a second placeholder. In some embodiments, a hinge can be located between the two substrate placeholders that allows the substrate holder to close, e.g., make a sandwich between the two substrate placeholders. In some embodiments, when the substrate holder is closed the biological sample and the array with capture probes are contacted with one another under conditions sufficient to allow analytes present in the biological sample to interact with the capture probes of the array. For example, dried permeabilization reagents can be placed on the biological sample and rehydrated. A permeabilization solution can be flowed through the substrate holder to permeabilize the biological sample and allow analytes in the biological sample to interact with the capture probes. Additionally, the temperature of the substrates or permeabilization solution can be used to initiate or control the rate of permeabilization. For example, the substrate including the array, the substrate including the biological sample, or both substrates can be held at a low temperature to slow diffusion and permeabilization efficiency. Once sandwiched, in some embodiments, the substrates can be heated to initiate permeabilization and/or increase diffusion efficiency. Transcripts that are released from the permeabilized tissue can diffuse to the array and be captured by the capture probes. The sandwich can be opened, and cDNA synthesis can be performed on the array.

In some embodiments, the methods as disclosed herein include hybridizing of one or more probe oligonucleotide probe pairs (e.g., RTL probes) to adjacent or nearby sequences of a target analyte (e.g., RNA; e.g., mRNA) of interest. In some embodiments, the probe oligonucleotide pairs include sequences that are complementary or substantially complementary to an analyte. For example, in some embodiments, each probe oligonucleotide includes a sequence that is complementary or substantially complementary to an mRNA of interest (e.g., to a portion of the sequence of an mRNA of interest). In some embodiments, each target analyte includes a first target region and a second target region. In some embodiments, the methods include providing a plurality of first probe oligonucleotides and a plurality of second probe oligonucleotides, wherein a pair of probe oligonucleotides for a target analyte comprises both a first and second probe oligonucleotide. In some embodiments, a first probe oligonucleotide hybridizes to a first target region of the analyte, and the second probe oligonucleotide hybridizes to a second, adjacent or nearly adjacent target region of the analyte.

In some instances, the probe oligonucleotides are DNA molecules. In some instances, the first probe oligonucleotide is a DNA molecule. In some instances, the second probe oligonucleotide is a DNA molecule. In some instances, the first probe oligonucleotide comprises at least two ribonucleic acid bases at the 3' end. In some instances, the second probe oligonucleotide comprises a phosphorylated nucleotide at the 5' end.

RTL probes can be designed using methods known in the art. In some instances, probe pairs are designed to cover an entire transcriptome of a species (e.g., a mouse or a human). In some instances, RTL probes are designed to cover a subset of a transcriptome (e.g., a mouse or a human). In some instances, the methods disclosed herein utilize about 500, about 1000, about 2000, about 3000, about 4000, about 5000, about 6000, about 7000, about 8000, about 9000, about 10,000, about 15,000, about 20,000, or more probe pairs.

In some embodiments, one of the probe oligonucleotides of the pair of probe oligonucleotides for RTL includes a poly(A) sequence or a complement thereof. In some instances, the poly(A) sequence or a complement thereof is on the 5' end of one of the probe oligonucleotides. In some instances, the poly(A) sequence or a complement thereof is on the 3' end of one of the probe oligonucleotides. In some embodiments, one probe oligonucleotide of the pair of probe oligonucleotides for RTL includes a degenerate or UMI sequence. In some embodiments, the UMI sequence is specific to a particular target or set of targets. In some instances, the UMI sequence or a complement thereof is on the 5' end of one of the probe oligonucleotides. In some instances, the UMI sequence or a complement thereof is on the 3' end of one of the probe oligonucleotides.

In some instances, the first and second target regions of an analyte are directly adjacent to one another. In some embodiments, the complementary sequences to which the first probe oligonucleotide and the second probe oligonucleotide hybridize are 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, about 125, or about 150 nucleotides away from each other. Gaps between the probe oligonucleotides may first be filled prior to coupling (e.g., ligation), using, for example, dNTPs in combination with a polymerase such as polymerase mu, DNA polymerase, RNA polymerase, reverse transcriptase, VENT polymerase, Taq polymerase, and/or any combinations, derivatives, and variants (e.g., engineered mutants) thereof. In some embodiments, when the first and second probe oligonucleotides are separated from each other by one or more nucleotides, deoxyribonucleotides are used to extend and couple (e.g., ligate) the first and second probe oligonucleotides.

In some instances, the first probe oligonucleotide and the second probe oligonucleotide hybridize to an analyte on the same transcript. In some instances, the first probe oligonucleotide and the second probe oligonucleotide hybridize to an analyte on the same exon. In some instances, the first probe oligonucleotide and the second probe oligonucleotide hybridize to an analyte on different exons. In some instances, the first probe oligonucleotide and the second probe oligonucleotide hybridize to an analyte that is the result of a translocation event (e.g., in the setting of cancer). The methods provided herein make it possible to identify alternative splicing events, translocation events, and mutations that change the hybridization rate of one or both probe oligonucleotides (e.g., single nucleotide polymorphisms, insertions, deletions, point mutations).

In some embodiments, the first and/or second probe as disclosed herein includes at least two ribonucleic acid bases at the 3' end; a functional sequence; a phosphorylated nucleotide at the 5' end; and/or a capture probe binding domain. In some embodiments, the functional sequence is a primer sequence.

The "capture probe binding domain" is a sequence that is complementary to a particular capture domain present in a capture probe. In some embodiments, the capture probe binding domain includes a poly(A) sequence. In some embodiments, the capture probe binding domain includes a poly-uridine sequence, a poly-thymidine sequence, or a combination thereof. In some embodiments, the capture probe binding domain includes a random sequence (e.g., a random hexamer or octamer). In some embodiments, the capture probe binding domain is complementary to a capture domain in a capture probe that detects a particular target(s) of interest. In some embodiments, a capture probe binding domain blocking moiety that interacts with the capture probe binding domain is provided. In some embodiments, a capture probe binding domain blocking moiety includes a sequence that is complementary or substantially complementary to a capture probe binding domain. In some embodiments, a capture probe binding domain blocking moiety prevents the capture probe binding domain from binding the capture probe when present. In some embodiments, a capture probe binding domain blocking moiety is removed prior to binding the capture probe binding domain (e.g., present in a connected probe (e.g., a ligation product)) to a capture probe. In some embodiments, a capture probe binding domain blocking moiety comprises a poly-uridine sequence, a poly-thymidine sequence, or a combination thereof.

Hybridization of the probe oligonucleotides to the target analyte can occur at a target having a sequence that is 100% complementary to the probe oligonucleotide(s). In some embodiments, hybridization can occur at a target having a sequence that is at least (e.g. at least about) 80%, at least (e.g. at least about) 85%, at least (e.g. at least about) 90%, at least (e.g. at least about) 95%, at least (e.g. at least about) 96%, at least (e.g. at least about) 97%, at least (e.g. at least about) 98%, or at least (e.g. at least about) 99% complementary to the probe oligonucleotide(s). After hybridization, in some embodiments, the first probe oligonucleotide is extended. After hybridization, in some embodiments, the second probe oligonucleotide is extended. For example, in some instances a first probe oligonucleotide hybridizes to a target sequence upstream for a second oligonucleotide probe, whereas in other instances a first probe oligonucleotide hybridizes to a target sequence downstream of a second probe oligonucleotide.

In some embodiments, methods disclosed herein include a wash step after hybridizing the first and the second probe oligonucleotides. The wash step removes any unbound oligonucleotides and can be performed using any technique known in the art. In some embodiments, a pre-hybridization buffer is used to wash the sample. In some embodiments, a phosphate buffer is used. In some embodiments, multiple wash steps are performed to remove unbound oligonucleotides. For example, it is advantageous to decrease the amount of unhybridized probes present in a biological sample as they may interfere with downstream applications and methods.

In some embodiments, after hybridization of probe oligonucleotides (e.g., first and the second probe oligonucleotides) to the target analyte, the probe oligonucleotides (e.g., the first probe oligonucleotide and the second probe oligonucleotide) are coupled (e.g., ligated) together, creating a single connected probe (e.g., a ligation product) that is complementary to the target analyte. Ligation can be performed enzymatically or chemically, as described herein. For example, the first and second probe oligonucleotides are hybridized to the first and second target regions of the analyte, and the probe oligonucleotides are subjected to a nucleic acid reaction to ligate them together. For example, the probes may be subjected to an enzymatic ligation reaction using a ligase (e.g., T4 RNA ligase (Rnl2), a SplintR ligase, or a T4 DNA ligase). See, e.g., Zhang L., et al.; Archaeal RNA ligase from thermoccocus kodakarensis for template dependent ligation RNA Biol. 2017; 14(1): 36-44 for a description of KOD ligase. A skilled artisan will understand that various reagents, buffers, cofactors, etc. may be included in a ligation reaction depending on the ligase being used.

In some embodiments, the first probe oligonucleotide and the second probe oligonucleotides are on a contiguous nucleic acid sequence. In some embodiments, the first probe oligonucleotide is on the 3' end of the contiguous nucleic acid sequence. In some embodiments, the first probe oligonucleotide is on the 5' end of the contiguous nucleic acid sequence. In some embodiments, the second probe oligonucleotide is on the 3' end of the contiguous nucleic acid sequence. In some embodiments, the second probe oligonucleotide is on the 5' end of the contiguous nucleic acid sequence.

In some embodiments, the method further includes hybridizing a third probe oligonucleotide to the first probe oligonucleotide and the second probe oligonucleotide such that the first probe oligonucleotide and the second probe oligonucleotide abut each other. In some embodiments, the third probe oligonucleotide comprises a sequence that is at least 80%, at least 85%, at least 90%, at least 95%, at least 96%, at least 97%, at least 98%, or at least 99% complementary to a portion of the first probe oligonucleotide that hybridizes to the third probe oligonucleotide. In some embodiments, the third probe oligonucleotide comprises a sequence that is 100% complementary to a portion of the first probe oligonucleotide that hybridizes to the third probe oligonucleotide. In some embodiments, the third probe oligonucleotide comprises a sequence that is at least 80%, at least 85%, at least 90%, at least 95%, at least 96%, at least 97%, at least 98%, or at least 99% complementary to a portion of the second probe oligonucleotide that hybridizes to the third probe oligonucleotide. In some embodiments, the third probe oligonucleotide comprises a sequence that is 100% complementary to a portion of the second probe oligonucleotide that hybridizes to the third probe oligonucleotide.

In some embodiments, a method for identifying a location of an analyte in a biological sample exposed to different permeabilization conditions includes (a) contacting the biological sample with a substrate, wherein the substrate comprises a plurality of capture probes, wherein a capture probe of the plurality of capture probes comprises a capture domain; (b) contacting the biological sample with a first probe oligonucleotide and a second probe oligonucleotide, wherein the first probe oligonucleotide and the second probe oligonucleotide are substantially complementary to adjacent sequences of the analyte, and wherein the second probe oligonucleotide comprises a capture probe-binding domain that is capable of binding to a capture domain of the capture probe; (c) hybridizing the first probe oligonucleotide and the second probe oligonucleotide to adjacent sequences of the analyte; (d) coupling (e.g., ligating) the first probe oligonucleotide and the second probe oligonucleotide, thereby creating a connected probe (e.g., a connected probe (e.g., a ligation product)) that is substantially complementary to the analyte; (e) releasing the connected probe (e.g., a ligation product) from the analyte; (f) hybridizing the capture probe-binding domain of the connected probe (e.g., a ligation product) to the hybridization domain of the capture probe; (g) hybridizing a padlock oligonucleotide to the connected probe (e.g., a ligation product) bound to the capture domain (e.g., such that the padlock oligonucleotide is circularized), wherein the padlock oligonucleotide comprises: (i) a first sequence that is substantially complementary to a first portion of the connected probe (e.g., a ligation product), (ii) a backbone sequence, and (iii) a second sequence that is substantially complementary to a second portion of the connected probe (e.g., a ligation product); and (i) ligating and amplifying the circularized padlock oligonucleotide (e.g., using rolling circle amplification using the circularized padlock oligonucleotide as a template), thereby creating an amplified circularized padlock oligonucleotide, and using the amplified circularized padlock oligonucleotide to identify the location of the analyte in the biological sample.

In some embodiments, the method further includes amplifying the connected probe (e.g., a ligation product) prior to the releasing step. In some embodiments, the entire connected probe (e.g., a ligation product) is amplified. In some embodiments, only part of the connected probe (e.g., a ligation product) is amplified. In some embodiments, amplification is isothermal. In some embodiments, amplification is not isothermal. Amplification can be performed using any of the methods described herein such as, but not limited to, a strand-displacement amplification reaction, a rolling circle amplification reaction, a ligase chain reaction, a transcription-mediated amplification reaction, an isothermal amplification reaction, and/or a 10 loop-mediated amplification reaction. In some embodiments, amplifying the connected probe (e.g., a ligation product) creates an amplified connected probe (e.g., a ligation product) that includes (i) all or part of sequence of the connected probe (e.g., a ligation product) specifically bound to the capture domain, or a complement thereof, and (ii) all or a part of the sequence of the spatial barcode, or a complement thereof.

In some embodiments, the method further includes determining (i) all or a part of the sequence of the connected probe (e.g., a ligation product), or a complement thereof, and (ii) all or a part of the sequence of the spatial barcode, or a complement thereof. In some embodiments, the method further includes using the determined sequence of (i) and (ii) to determine the location and abundance of the analyte in the biological sample.

In some embodiments, after coupling (e.g., ligation) of the first and second probe oligonucleotides to create a ligation product, the connected probe (e.g., a ligation product) is released from the analyte. To release the connected probe (e.g., a ligation product), an endoribonuclease (e.g., RNase A, RNase C, RNase H, or RNase I) is used. An endoribonuclease such as RNase H specifically cleaves RNA in RNA:DNA hybrids. In some embodiments, the connected probe (e.g., a ligation product) is released enzymatically. In some embodiments, an endoribonuclease is used to release the probe from the analyte. In some embodiments, the endoribonuclease is one or more of RNase H. In some embodiments, the RNase H is RNase H1 or RNase H2.

In some embodiments, the releasing of the connected probe (e.g., a ligation product) includes contacting the biological sample with a reagent medium comprising a permeabilization agent and an agent for releasing the connected probe (e.g., a ligation product), thereby permeabilizing the biological sample and releasing the connected probe (e.g., a ligation product) from the analyte. In some embodiments, the agent for releasing the connected probe (e.g., a ligation product) comprises a nuclease. In some embodiments, the nuclease is an endonuclease. In some embodiments, the nuclease is an exonuclease. In some embodiments, the nuclease includes an RNase. In some embodiments, the RNase is selected from RNase A, RNase C, RNase H, or RNase I.

In some embodiments, the reagent medium comprises polyethylene glycol (PEG). In some embodiments, the PEG is from about PEG 2K to about PEG 16K. In some embodiments, the PEG is PEG 2K, 3K, 4K, 5K, 6K, 7K, 8K, 9K, 10K, 11K, 12K, 13K, 14K, 15K, or 16K. In some embodiments, the PEG is present at a concentration from about 2% to 25%, from about 4% to about 23%, from about 6% to about 21%, or from about 8% to about 20% (v/v).

In some embodiments, the reagent medium includes a wetting agent.

In some instances, after creation of the connected probe (e.g., a ligation product), the methods disclosed herein include simultaneous treatment of the biological sample with a permeabilization agent such as proteinase K (to permeabilize the biological sample) and a releasing agent such as an endonuclease such as RNase H (to release the connected probe (e.g., a ligation product) from the analyte). In some instances, the permeabilization step and releasing step occur at the same time. In some instances, the permeabilization step occurs before the releasing step. In some embodiments, the permeabilization agent comprises a protease. In some embodiments, the protease is selected from trypsin, pepsin, elastase, or Proteinase K. In some embodiments, the protease is an endopeptidase. Endopeptidases that can be used include but are not limited to trypsin, chymotrypsin, elastase, thermolysin, pepsin, clostripan, glutamyl endopeptidase (GluC), ArgC, peptidyl-asp endopeptidase (ApsN), endopeptidase LysC and endopeptidase LysN. In some embodiments, the endopeptidase is pepsin.

In some embodiments, the reagent medium further includes a detergent. In some embodiments, the detergent is selected from sodium dodecyl sulfate (SDS), sarkosyl, saponin, Triton X-100™, or Tween-20™. In some embodiments, the reagent medium includes less than 5 w/v % of a detergent selected from sodium dodecyl sulfate (SDS) and sarkosyl. In some embodiments, the reagent medium includes at least 5% w/v % of a detergent selected from SDS and sarkosyl. In some embodiments, the reagent medium does not include SDS or sarkosyl.

In some embodiments, the biological sample and the array are contacted with the reagent medium for about 1 to about 60 minutes (e.g., about 1 to about 55 minutes, about 1 to about 50 minutes, about 1 to about 45 minutes, about 1 to about 40 minutes, about 1 to about 35 minutes, about 1 to about 30 minutes, about 1 to about 25 minutes, about 1 to about 20 minutes, about 1 to about 15 minutes, about 1 to about 10 minutes, about 1 to about 5 minutes, about 5 to about 60 minutes, about 5 to about 55 minutes, about 5 to about 50 minutes, about 5 to about 45 minutes, about 5 to about 40 minutes, about 5 to about 35 minutes, about 5 to about 30 minutes, about 5 to about 25 minutes, about 5 to about 20 minutes, about 5 to about 15 minutes, about 5 to about 10 minutes, about 10 to about 60 minutes, about 10 to about 55 minutes, about 10 to about 50 minutes, about 10 to about 45 minutes, about 10 to about 40 minutes, about 10 to about 35 minutes, about 10 to about 30 minutes, about 10 to about 25 minutes, about 10 to about 20 minutes, about 10 to about 15 minutes, about 15 to about 60 minutes, about 15 to about 55 minutes, about 15 to about 50 minutes, about 15 to about 45 minutes, about 15 to about 40 minutes, about 15 to about 35 minutes, about 15 to about 30 minutes, about 15 to about 25 minutes, about 15 to about 20 minutes, about 20 to about 60 minutes, about 20 to about 55 minutes, about 20 to about 50 minutes, about 20 to about 45 minutes, about 20 to about 40 minutes, about 20 to about 35 minutes, about 20 to about 30 minutes, about 20 to about 25 minutes, about 25 to about 60 minutes, about 25 to about 55 minutes, about 25 to about 50 minutes, about 25 to about 45 minutes, about 25 to about 40 minutes, about 25 to about 35 minutes, about 25 to about 30 minutes, about 30 to about 60 minutes, about 30 to about 55 minutes, about 30 to about 50 minutes, about 30 to about 45 minutes, about 30 to about 40 minutes, about 30 to about 35 minutes, about 35 to about 60 minutes, about 35 to about 55 minutes, about 35 to about 50 minutes, about 35 to about 45 minutes, about 35 to about 40 minutes, about 40 to about 60 minutes, about 40 to about 55 minutes, about 40 to about 50 minutes, about 40 to about 45 minutes, about 45 to about 60 minutes, about 45 to about 55 minutes, about 45 to about 50 minutes, about 50 to about 60 minutes, about 50 to about 55 minutes, or about 55 to about 60 minutes). In some embodiments, the biological sample and the array are contacted with the reagent medium for about 30 minutes.

In some embodiments, the connected probe (e.g., a ligation product) includes a capture probe binding domain, which can hybridize to a capture probe (e.g., a capture probe immobilized, directly or indirectly, on a substrate). In some embodiments, the capture probe includes a spatial barcode and the capture domain. In some embodiments, the capture probe binding domain of the connected probe (e.g., a ligation product) specifically binds to the capture domain of the capture probe.

In some embodiments, methods provided herein include mounting a biological sample on a first substrate, then aligning the first substrate with a second substrate including an array, such that at least a portion of the biological sample is aligned with at least a portion of the array, wherein the array includes a plurality of capture probes. After hybridization of the connected probe (e.g., a ligation product) to the capture probe, downstream methods as disclosed herein can be performed.

In some embodiments, at least 50% of connected probes (e.g., a ligation products) released from the portion of the biological sample aligned with the portion of the array are captured by capture probes of the portion of the array. In some embodiments, at least 50%, at least 55%, at least 60%, at least 65%, at least 70%, at least 75%, at least 85%, at least 90%, at least 95%, at least 96%, at least 97%, at least 98%, at least 99%, or 100% of connected probe (e.g., a ligation products) are detected in spots directly under the biological sample.

In some embodiments, the capture probe includes a poly (T) sequence. In some embodiments, capture probe includes a sequence specific to the analyte. In some embodiments, the capture probe includes a functional domain. In some embodiments, the capture probe further includes one or more functional domains, a unique molecular identifier (UMI), a cleavage domain, and combinations thereof. In some embodiments, the capture probe binding domain includes a poly(A) sequence. In some embodiments, the capture probe binding domain includes a sequence complementary to a capture domain of a capture probe that detects a target analyte of interest. In some embodiments, the analyte is RNA. In some embodiments, the analyte is mRNA.

In some embodiments, the connected probe (e.g., a ligation product) (e.g., the analyte derived molecule) includes a capture probe binding domain, which can hybridize to a capture probe (e.g., a capture probe immobilized, directly or indirectly, on a substrate). Methods provided herein include contacting a biological sample with a substrate, wherein the capture probe is affixed to the substrate (e.g., immobilized to the substrate, directly or indirectly). After hybridization of the connected probe (e.g., a ligation product) to the capture probe, downstream methods as disclosed herein (e.g., sequencing, in situ analysis such as RCA) can be performed.

In some embodiments, the method further includes analyzing a different analyte in the biological sample. In some embodiments, the analysis of the different analyte includes (a) further contacting the biological sample with a plurality of analyte capture agents, wherein an analyte capture agent of the plurality of analyte capture agents includes an analyte binding moiety and a capture agent barcode domain, wherein the analyte binding moiety specifically binds to the different analyte, and wherein the capture agent barcode domain includes an analyte binding moiety barcode and an capture handle sequence that is complementary to a capture domain of a capture probe; and (b) hybridizing the analyte capture sequence to the capture domain.

Figure 16A:
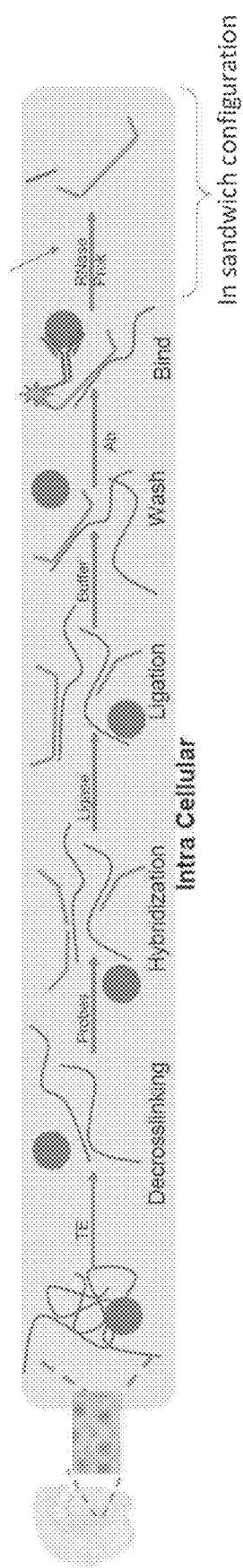
FIG. 16A shows an exemplary workflow for using ligated probes and analyte capture agents to capture intracellular analytes.

An exemplary embodiment of a workflow for analysis of protein and RNA analytes is shown in FIG. 16A. As shown in FIG. 16A, a fixed tissue sample mounted on a first substrate (e.g., a slide-mounted tissue sample) is decrosslinked, followed by hybridization of probe pairs to nucleic acid analyte analytes. Also as shown in FIG. 16A, a first and second probe of a probe pair is connected, e.g., ligated. The sample is optionally washed (e.g., with a buffer), prior to incubation with an analyte capture agent (e.g., an antibody) that specifically binds a different analyte, e.g., a protein analyte. The analyte capture agent comprises a capture agent barcode domain. In some embodiments, the analyte capture agent is an antibody with an oligonucleotide tag, the oligonucleotide tag comprising a capture agent barcode domain. In some embodiments, the connected probes (e.g., the ligation products) and antibody oligonucleotide tags are released from the tissue under sandwich conditions as described herein. For the sandwich conditions, the tissue-mounted slide can be aligned with an array and permeabilized with a reagent medium in the sandwich configuration as described herein (see, e.g., FIG. 16B). In some embodiments, the reagent medium comprises RNase and a permeabilization agent (e.g., Proteinase K). Permeabilization releases the connected probe (e.g., a ligation product) and capture agent barcode domain, for capture onto a second substrate comprising an array with a plurality of capture probes (see, e.g., FIG. 16B). After capture of the connected probe and capture agent barcode domain, the tissue slide can be removed (e.g., the sandwich can be "opened" or "broken").

In some embodiments, following opening of the sandwich, the capture probes can be extended, sequencing libraries can be prepared and sequenced, and the results can be analyzed computationally.

In some embodiments, the method further includes determining (i) all or part of the sequence of the capture agent barcode domain; and (ii) all or a part of the sequence of the spatial barcode, or a complement thereof. In some embodiments, the method further includes using the determined sequence of (i), and (ii) to analyze the different analyte in the biological sample. In some embodiments, the releasing step further releases the capture agent barcode domain from the different analyte. In some embodiments, the different analyte is a protein analyte. In some embodiments, the protein analyte is an extracellular protein. In some embodiments, the protein analyte is an intracellular protein.

(c) Capturing Analytes for Spatial Detection Using Analyte Capture Agents

In some embodiments, the methods, compositions, devices, and systems provided herein utilize analyte capture agents for spatial detection. An "analyte capture agent" refers to a molecule that interacts with a target analyte (e.g., a protein) and with a capture probe. Such analyte capture agents can be used to identify the analyte. In some embodiments, the analyte capture agent can include an analyte binding moiety and a capture agent barcode domain. In some embodiments, the analyte capture agent includes a linker. In some embodiments, the linker is a cleavable linker. In some embodiments, the cleavable linker is a photo-cleavable linker, a UV-cleavable linker, or an enzyme cleavable linker.

An analyte binding moiety is a molecule capable of binding to a specific analyte. In some embodiments, the analyte binding moiety comprises an antibody or antibody fragment. In some embodiments, the analyte binding moiety comprises a polypeptide and/or an aptamer. In some embodiments, the analyte is a protein (e.g., a protein on a surface of a cell or an intracellular protein).

A capture agent barcode domain can include a capture handle sequence which can hybridize to at least a portion or an entirety of a capture domain of a capture probe. In some embodiments, the capture handle sequence is complementary to a portion or entirety of a capture domain of a capture probe. In some embodiments, the capture handle sequence includes a poly (A) tail. In some embodiments, the capture handle sequence includes a sequence capable of binding a poly (T) domain. In some embodiments, the capture agent barcode domain comprises an analyte binding moiety barcode and a capture handle sequence. The analyte binding moiety barcode refers to a barcode that is associated with or otherwise identifies the analyte binding moiety, and the capture handle sequence can hybridize to a capture probe. In some embodiments, the capture handle sequence specifically binds to the capture domain of the capture probe. Other embodiments of an analyte capture agent useful in spatial analyte detection are described herein.

Provided herein are methods for analyzing an analyte in a biological sample including (a) contacting the biological sample with a plurality of analyte capture agents, wherein an analyte capture agent of the plurality of analyte capture agents includes an analyte binding moiety and a capture agent barcode domain, wherein the analyte binding moiety specifically binds to the analyte, and wherein the capture agent barcode domain includes an analyte binding moiety barcode and an capture handle sequence; (b) contacting the biological sample with a reagent medium including an agent for releasing the capture agent barcode domain from the analyte binding moiety, thereby releasing the capture agent barcode domain from the analyte binding moiety; and (c) hybridizing the capture handle sequence to a capture domain of a capture probe, wherein the capture probe includes (i) a spatial barcode and (ii) a capture domain.

Also provided herein are methods for analyzing an analyte in a biological sample mounted on a first substrate including (a) contacting the biological sample with a plurality of analyte capture agents, wherein an analyte capture agent of the plurality of analyte capture agents includes an analyte binding moiety and a capture agent barcode domain, wherein the analyte binding moiety specifically binds to the analyte, and wherein the capture agent barcode domain includes an analyte binding moiety barcode and an capture handle sequence; (b) aligning the first substrate with a second substrate comprising an array, such that at least a portion of the biological sample is aligned with at least a portion of the array, wherein the array includes a plurality of capture probes, wherein a capture probe of the plurality of capture probes includes (i) a spatial barcode and (ii) a capture domain; (c) when the biological sample is aligned with at least a portion of the array, (i) releasing the capture agent barcode domain from the analyte and (ii) passively or actively migrating the capture agent barcode domain from the biological sample to the array; and (d) coupling the capture handle sequence to the capture domain.

Also provided herein are methods for analyzing an analyte in a biological sample mounted on a first substrate including (a) contacting the biological sample with a plurality of analyte capture agents, wherein an analyte capture agent of the plurality of analyte capture agents includes an analyte binding moiety and a capture agent barcode domain, wherein the analyte binding moiety specifically binds to the analyte, and wherein the capture agent barcode domain includes an analyte binding moiety barcode and an capture handle sequence; (b) aligning the first substrate with a second substrate comprising an array, such that at least a portion of the biological sample is aligned with at least a portion of the array, wherein the array includes a plurality of capture probes, wherein a capture probe of the plurality of capture probes includes (i) a spatial barcode and (ii) a capture domain; (c) when the biological sample is aligned with at least a portion of the array, (i) releasing the capture agent barcode domain from the analyte and (ii) passively or actively migrating the capture agent barcode domain from the biological sample to the array; and (d) hybridizing the capture handle sequence to the capture domain.

In some embodiments, the process of transferring the connected probe (e.g., a ligation product) from the first substrate to the second substrate is referred to as a "sandwich process". The sandwich process is described above and in PCT Patent Application Publication No. WO 2020/123320, which is incorporated by reference in its entirety.

In some embodiments, the method further includes determining (i) all or a part of the capture agent barcode domain, or a complement thereof; and (ii) all or a part of the sequence of the spatial barcode, or a complement thereof. In some embodiments, the method further includes using the determined sequence of (i) and (ii) to determine the location and abundance of the analyte in the biological sample.

In some embodiments, an analyte capture agent is introduced to a biological sample, wherein the analyte binding moiety specifically binds to a target analyte, and then the biological sample can be treated to release the capture agent barcode domain from the biological sample. In some embodiments, the capture agent barcode domain can then migrate and bind to a capture domain of a capture probe, and the capture agent barcode domain can be extended to generate a spatial barcode complement at the end of the capture agent barcode domain. In some embodiments, the spatially-tagged capture agent barcode domain can be denatured from the capture probe, and analyzed using methods described herein.

In some embodiments, the releasing includes contacting the biological sample and the array with a reagent medium including a nuclease. In some embodiments, the nuclease includes an RNase. In some embodiments, the RNase is selected from RNase A, RNase C, RNase H, and RNase I. In some embodiments, the reagent medium further includes a permeabilization agent. In some embodiments, the releasing further includes simultaneously permeabilizing the biological sample and releasing the capture agent barcode domain from the analyte. In some embodiments, the permeabilization agent further includes a protease. In some embodiments, the protease is selected from trypsin, pepsin, elastase, or Proteinase K.

In some embodiments, the capture agent barcode domain is released from the analyte binding moiety by using a different stimulus that can include, but is not limited to, a proteinase (e.g., Proteinase K), an RNase, and UV light.

In some embodiments, the reagent medium further includes a detergent. In some embodiments, the detergent is selected from sodium dodecyl sulfate (SDS), sarkosyl, saponin, Triton X-100™, or Tween-20™. In some embodiments, the reagent medium includes less than 5 w/v % of a detergent selected from sodium dodecyl sulfate (SDS) and sarkosyl. In some embodiments, the reagent medium includes as least 5% w/v % of a detergent selected from SDS and sarkosyl. In some embodiments, the reagent medium does not include SDS or sarkosyl.

In some embodiments, the biological sample and the array are contacted with the reagent medium for about 1 to about 60 minutes (e.g., about 1 to about 55 minutes, about 1 to about 50 minutes, about 1 to about 45 minutes, about 1 to about 40 minutes, about 1 to about 35 minutes, about 1 to about 30 minutes, about 1 to about 25 minutes, about 1 to about 20 minutes, about 1 to about 15 minutes, about 1 to about 10 minutes, about 1 to about 5 minutes, about 5 to about 60 minutes, about 5 to about 55 minutes, about 5 to about 50 minutes, about 5 to about 45 minutes, about 5 to about 40 minutes, about 5 to about 35 minutes, about 5 to about 30 minutes, about 5 to about 25 minutes, about 5 to about 20 minutes, about 5 to about 15 minutes, about 5 to about 10 minutes, about 10 to about 60 minutes, about 10 to about 55 minutes, about 10 to about 50 minutes, about 10 to about 45 minutes, about 10 to about 40 minutes, about 10 to about 35 minutes, about 10 to about 30 minutes, about 10 to about 25 minutes, about 10 to about 20 minutes, about 10 to about 15 minutes, about 15 to about 60 minutes, about 15 to about 55 minutes, about 15 to about 50 minutes, about 15 to about 45 minutes, about 15 to about 40 minutes, about 15 to about 35 minutes, about 15 to about 30 minutes, about 15 to about 25 minutes, about 15 to about 20 minutes, about 20 to about 60 minutes, about 20 to about 55 minutes, about 20 to about 50 minutes, about 20 to about 45 minutes, about 20 to about 40 minutes, about 20 to about 35 minutes, about 20 to about 30 minutes, about 20 to about 25 minutes, about 25 to about 60 minutes, about 25 to about 55 minutes, about 25 to about 50 minutes, about 25 to about 45 minutes, about 25 to about 40 minutes, about 25 to about 35 minutes, about 30 to about 60 minutes, about 30 to about 55 minutes, about 30 to about 50 minutes, about 30 to about 45 minutes, about 30 to about 40 minutes, about 35 to about 60 minutes, about 35 to about 55 minutes, about 35 to about 50 minutes, about 35 to about 45 minutes, about 35 to about 40 minutes, about 40 to about 60 minutes, about 40 to about 55 minutes, about 40 to about 50 minutes, about 40 to about 45 minutes, about 45 to about 60 minutes, about 45 to about 55 minutes, about 45 to about 50 minutes, about 50 to about 60 minutes, about 50 to about 55 minutes, or about 55 to about 60 minutes). In some embodiments, the biological sample and the array are contacted with the reagent medium for about 30 minutes.

Also provided herein are methods further including analyzing a different analyte in the biological sample. In some embodiments, the analysis of the different analyte includes (a) hybridizing a first probe oligonucleotide and a second probe oligonucleotide to the different analyte, wherein the first probe oligonucleotide and the second probe oligonucleotide each comprise a sequence that is substantially complementary to adjacent sequences of the different analyte, and wherein the second probe oligonucleotide comprises a capture probe binding domain; (b) ligating the first probe oligonucleotide and the second probe oligonucleotide, thereby generating a connected probe (e.g., a ligation product) comprising the capture probe binding domain; and (c) hybridizing the capture probe binding domain of the connected probe (e.g., a ligation product) to the capture domain.

In some embodiments, the method further includes determining (i) all or part of the sequence of the connected probe (e.g., a ligation product), or a complement thereof, and (ii) all or a part of the sequence of the spatial barcode, or a complement thereof. In some embodiments, the method further includes using the determined sequence of (i), and (ii) to analyze the different analyte in the biological sample. In some embodiments, the releasing step further releases the connected probe (e.g., a ligation product) from the different analyte. In some embodiments, the different analyte is RNA. In some embodiments, the different analyte is mRNA.

In some embodiments, the capture probe comprises a poly(T) sequence. In some embodiments, the capture probe comprises a sequence complementary to the capture handle sequence. In some embodiments, the capture probe comprises a functional domain. In some embodiments, the capture probe further comprises one or more functional domains, a unique molecular identifier (UMI), a cleavage domain, and combinations thereof.

In some embodiments, the biological sample is a tissue sample. In some embodiments, the tissue sample is a tissue section. In some embodiments, the tissue sample is a fixed tissue sample. In some embodiments, the fixed tissue sample is a formalin fixed paraffin embedded (FFPE) tissue sample. In some embodiments, the FFPE tissue is deparaffinized and decrosslinked prior to step (a) of any one of the methods provided herein. In some embodiments, the fixed tissue sample is a formalin fixed paraffin embedded cell pellet. In some embodiments, the tissue sample is a fresh tissue sample or a frozen tissue sample. In some embodiments, the tissue sample is fixed and stained prior to step (a) of any one of the methods provided herein.

In some instances, RTL is performed between two oligonucleotides that each are affixed to an analyte binding moiety (i.e., a protein-binding moiety). Generally, the methods of RTL in this setting is as follows. In some embodiments, provided herein is a method of determining a location of at least one analyte in a biological sample including: (a) hybridizing a first analyte-binding moiety to a first analyte in the biological sample, wherein the first analyte-binding moiety is bound to a first oligonucleotide, wherein the first oligonucleotide comprises: (i) a functional sequence; (ii) a first barcode; and (iii) a first bridge sequence; (b) hybridizing a second analyte-binding moiety to a second analyte in the biological sample, wherein the second analyte-binding moiety is bound to a second oligonucleotide; wherein the second oligonucleotide comprises: (i) capture probe binding domain sequence, (ii) a second barcode; and (ii) a second bridge sequence; (c) contacting the biological sample with a third oligonucleotide; (d) hybridizing the third oligonucleotide to the first bridge sequence of the first oligonucleotide and second bridge sequence of the second oligonucleotide; (e) ligating the first oligonucleotide and the second oligonucleotide, creating a connected probe (e.g., a ligation product); (f) contacting the biological sample with a substrate, wherein a capture probe is affixed to the substrate, wherein the capture probe comprises a spatial barcode and the capture domain; and (g) allowing the capture probe binding domain sequence of the second oligonucleotide to specifically bind to the capture domain. In some instances, the connected probe (e.g., a ligation product) is cleaved from the analyte biding moieties.

In some instances, two analytes (e.g., two different proteins) in close proximity in a biological sample are detected by a first analyte-binding moiety and a second analyte-binding moiety, respectively. In some embodiments, a first analyte-binding moiety and/or the second analyte-binding moiety is an analyte capture agent (e.g., any of the exemplary analyte capture agents described herein). In some embodiments, the first analyte-binding moiety and/or the second analyte-binding moiety is a first protein. In some embodiments, the first analyte-binding moiety and/or the second analyte-binding moiety is an antibody. For example, the antibody can include, without limitation, a monoclonal antibody, recombinant antibody, synthetic antibody, a single domain antibody, a single-chain variable fragment (scFv), and or an antigen-binding fragment (Fab). In some embodiments, the first analyte-binding moiety binds to a cell surface analyte (e.g., any of the exemplary cell surface analytes described herein). In some embodiments, binding of the analyte is performed metabolically. In some embodiments, binding of the analyte is performed enzymatically. In some embodiments, the methods include a secondary antibody that binds to a primary antibody, enhancing its detection.

In some embodiments, the first analyte-binding moiety and the second analyte-binding moiety each bind to the same analyte. In some embodiments, the first analyte-binding moiety and/or second analyte-binding moiety each bind to a different analyte. For example, in some embodiments, the first analyte-binding moiety binds to a first polypeptide and the second analyte-binding moiety binds to a second polypeptide.

In some embodiments of any of the methods of determining a location of at least one analyte in a biological sample, a first and/or a second oligonucleotide are bound (e.g., conjugated or otherwise attached using any of the methods described herein) to a first analyte-binding moiety and/or a second analyte-binding moiety, respectively.

In some embodiments of any of the methods of determining a location of at least one analyte in a biological sample as described herein, a second oligonucleotide is bound (e.g., conjugated or otherwise attached using any of the methods described herein) to a second analyte-binding moiety. For example, the second oligonucleotide can be covalently linked to the second analyte-binding moiety. In some embodiments, the second oligonucleotide is bound to the second analyte-binding moiety via its 5' end. In some embodiments, the second oligonucleotide includes a free 3' end. In some embodiments the second oligonucleotide is bound to the second analyte-binding moiety via its 3' end. In some embodiments, the second oligonucleotide includes a free 5' end.

In some embodiments, the oligonucleotides are bound to the first and/or second analyte-binding moieties via a linker (e.g., any of the exemplary linkers described herein). In some embodiments, the linker is a cleavable linker. In some embodiment, the linker is a linker with photo-sensitive chemical bonds (e.g., photo-cleavable linkers). In some embodiments, the linker is a cleavable linker that can undergo induced dissociation.

FIGS. 17A-17B show exemplary schematics illustrating methods to release the capture agent barcode domain from the analyte binding moiety. FIG. 17A shows the use of an RNase cleavable linker to release a capture agent barcode domain from an analyte binding moiety of an analyte capture agent. In particular, a target (indicated by the circle in FIG. 17A interacts with an antibody. After an interaction is established, an enzyme (e.g., an RNAse) cleaves a linker, freeing a barcode from the antibody. The barcode, which is specific to the antibody, is captured on a slide comprising a plurality of probes. Similarly, FIG. 17B shows the use of a UV cleavable linker to release a capture agent barcode domain from an analyte binding moiety of an analyte capture agent.

In some embodiments, the oligonucleotides are bound (e.g., attached via any of the methods described herein) to an analyte-binding domain via a 5' end.

In some embodiments, a barcode is used to identify the analyte-binding moiety to which it is bound. The barcode can be any of the exemplary barcodes described herein. In some embodiments, the first and/or second oligonucleotide include a capture probe binding domain sequence. For example, a capture probe binding domain sequence can be a poly(A) sequence when the capture domain sequence is a poly(T) sequence.

In some embodiments, a third oligonucleotide (e.g., a splint oligonucleotide) hybridizes to both the first and second oligonucleotides and enables ligation of the first oligonucleotide and the second oligonucleotide. In some embodiments, a ligase is used. In some aspects, the ligase includes a DNA ligase. In some aspects, the ligase includes a RNA ligase. In some aspects, the ligase includes T4 DNA ligase. In some embodiments, the ligase is a SplintR ligase.

(d) Sandwich Processes

In some embodiments, one or more analytes from the biological sample are released from the biological sample and migrate to a substrate comprising an array of capture probes for attachment to the capture probes of the array. In some embodiments, the release and migration of the analytes to the substrate comprising the array of capture probes occurs in a manner that preserves the original spatial context of the analytes in the biological sample. In some embodiments, the biological sample is mounted on a first substrate and the substrate comprising the array of capture probes is a second substrate. In some embodiments, the alignment of the first substrate and the second substrate is facilitated by a sandwiching process. Accordingly, described herein are methods, compositions, devices, and systems for sandwiching together the first substrate as described herein with a second substrate having an array with capture probes.

Figure 23:
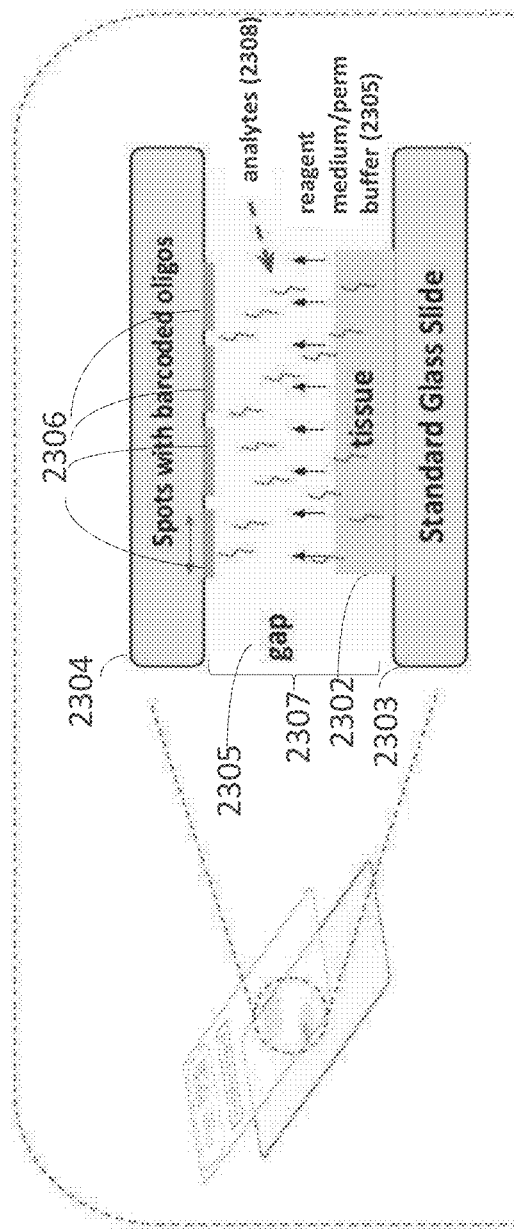
FIG. 23 shows an exemplary schematic diagram depicting a sandwiching process.

FIG. 23 is a schematic diagram depicting an exemplary sandwiching process between a first substrate comprising a biological sample (e.g., a tissue section 2302 on a slide 2303) and a second substrate comprising a spatially barcoded array, e.g., a slide 2304 that is populated with spatially-barcoded capture probes 2306. During the exemplary sandwiching process, the first substrate is aligned with the second substrate, such that at least a portion of the biological sample is aligned with at least a portion of the array (e.g., aligned in a sandwich configuration). As shown, the second substrate (e.g., slide 2304) is in a superior position to the first substrate (e.g., slide 2303). In some embodiments, the first substrate (e.g., slide 2303) may be positioned superior to the second substrate (e.g., slide 2304). In some embodiments, the first and second substrates are aligned to maintain a gap or separation distance 2307 between the two substrates. When the first and second substrates are aligned, one or more analytes are released from the biological sample and actively or passively migrate to the array for capture. In some embodiments, the migration occurs while the aligned portions of the biological sample and the array are contacted with a reagent medium 2305. The released one or more analytes may actively or passively migrate across the gap 2307 via the reagent medium 2305 toward the capture probes 2306, and be captured by the capture probes 2306.

In some embodiments, the separation distance 2307 between first and second substrates is maintained between 2 microns and 1 mm (e.g., between 2 microns and 800 microns, between 2 microns and 700 microns, between 2 microns and 600 microns, between 2 microns and 500 microns, between 2 microns and 400 microns, between 2 microns and 300 microns, between 2 microns and 200 microns, between 2 microns and 100 microns, between 2 microns and 25 microns, between 2 microns and 10 microns), measured in a direction orthogonal to the surface of first substrate that supports sample. In some embodiments, the separation distance 2307 between first and second substrates is less than 50 microns. In some instances, the distance is 2 microns. In some instances, the distance is 2.5 microns. In some instances, the distance is about 2, 3, 4, 5, 6, 7, 8, 9, 10, 11, 12, 13, 14, 15, 16, 17, 18, 19, 20, 21, 22, 23, 24, or 25 microns. In some embodiments, second substrate is placed in direct contact with the sample on the first substrate ensuring no diffusive spatial resolution losses. In some embodiments, the separation distance is measured in a direction orthogonal to a surface of the first substrate that supports the biological sample.

In some embodiments, the sandwiching process may be facilitated by a device, sample holder, sample handling apparatus, or system described in, e.g., US. Patent Application Pub. No. 20210189475, PCT/US2021/036788, or PCT/US2021/050931.

In some embodiments, the first and second substrates are placed in a substrate holder (e.g., an array alignment device) configured to align the biological sample and the array. In some embodiments, the device comprises a sample holder. In some embodiments, the sample holder includes a first member and a second member that receive a first substrate and a second substrate, respectively. The device can include an alignment mechanism that is connected to at least one of the members and aligns the first and second members. Thus, the devices of the disclosure can advantageously align the first substrate and the second substrate and any samples, barcoded probes, or permeabilization reagents that may be on the surface of the first and second substrates.

In some embodiments, the sandwiching process comprises: mounting the first substrate on a first member of a support device, the first member configured to retain the first substrate; mounting the second substrate on a second member of the support device, the second member configured to retain the second substrate, applying a reagent medium to the first substrate and/or the second substrate, the reagent medium comprising a permeabilization agent, operating an alignment mechanism of the support device to move the first member and/or the second member such that a portion of the biological sample is aligned (e.g., vertically aligned) with a portion of the array of capture probes and within a threshold distance of the array of capture probes, and such that the portion of the biological sample and the capture probe contact the reagent medium, wherein the permeabilization agent releases the analyte from the biological sample.

In some embodiments of a sample holder, the sample holder can include a first member including a first retaining mechanism configured to retain a first substrate comprising a sample. The first retaining mechanism can be configured to retain the first substrate disposed in a first plane. The sample holder can further include a second member including a second retaining mechanism configured to retain a second substrate disposed in a second plane. The sample holder can further includes an alignment mechanism connected to one or both of the first member and the second member. The alignment mechanism can be configured to align the first and second members along the first plane and/or the second plane such that the sample contacts at least a portion of the reagent medium when the first and second members are aligned and within a threshold distance along an axis orthogonal to the second plane. The alignment mechanism may be configured to move the second member along the axis orthogonal to the second plane and/or move the first member along an axis orthogonal to the first plane.

In some embodiments, the alignment mechanism includes a linear actuator. In some embodiments, the alignment mechanism includes one or more of a moving plate, a bushing, a shoulder screw, a motor bracket, and a linear actuator. The moving plate may be coupled to the first member or the second member. The alignment mechanism may, in some cases, include a first moving plate coupled to the first member and a second moving plate coupled to the second member. In some embodiments, the linear actuator is configured to move the second member along an axis orthogonal to the plane of the first member and/or the second member. For example, the moving plate may be coupled to the second member and adjust the separation distance along a z axis (e.g., orthogonal to the second substrate) by moving the moving plate up in a superior direction toward the first substrate. In some embodiments, the linear actuator is configured to move the first member along an axis orthogonal to the plane of the first member and/or the second member. The movement of the moving plate may be accomplished by the linear actuator configured to move the first member and/or the second member at a velocity. The velocity may be controlled by a controller communicatively coupled to the linear actuator. In some embodiments, the linear actuator is configured to move the first member, the second member, or both the first member and the second member at a velocity of at least 0.1 mm/sec (e.g., at least 0.1 mm/sec to 2 mm/sec). In some aspects, the velocity may be selected to reduce or minimize bubble generation or trapping within the reagent medium. In some embodiments, the linear actuator is configured to move the first member, the second member, or both the first member and the second member with an amount of force of at least 0.1 lbs (e.g., between 0.1-4.0 pounds of force).

In some aspects, the velocity of the moving plate (e.g., closing the sandwich) may affect bubble generation or trapping within the reagent medium. It may be advantageous to minimize bubble generation or trapping within the reagent medium during the "sandwiching" process, as bubbles can interfere with the migration of analytes through the reagent medium to the array. In some embodiments, the closing speed is selected to minimize bubble generation or trapping within the reagent medium. In some embodiments, the closing speed is selected to reduce the time it takes the flow front of the reagent medium from an initial point of contact with the first and second substrate to sweep across the sandwich area (also referred to herein as "closing time"). In some embodiments, the closing speed is selected to reduce the closing time to less than about 1100 milliseconds (ms). In some embodiments, the closing speed is selected to reduce the closing time to less than about 1000 ms. In some embodiments, the closing speed is selected to reduce the closing time to less than about 900 ms. In some embodiments, the closing speed is selected to reduce the closing time to less than about 750 ms. In some embodiments, the closing speed is selected to reduce the closing time to less than about 600 ms. In some embodiments, the closing speed is selected to reduce the closing time to about 550 ms or less.

In some embodiments, the closing speed is selected to reduce the closing time to about 370 ms or less. In some embodiments, the closing speed is selected to reduce the closing time to about 200 ms or less. In some embodiments, the closing speed is selected to reduce the closing time to about 150 ms or less.

Figure 37A:
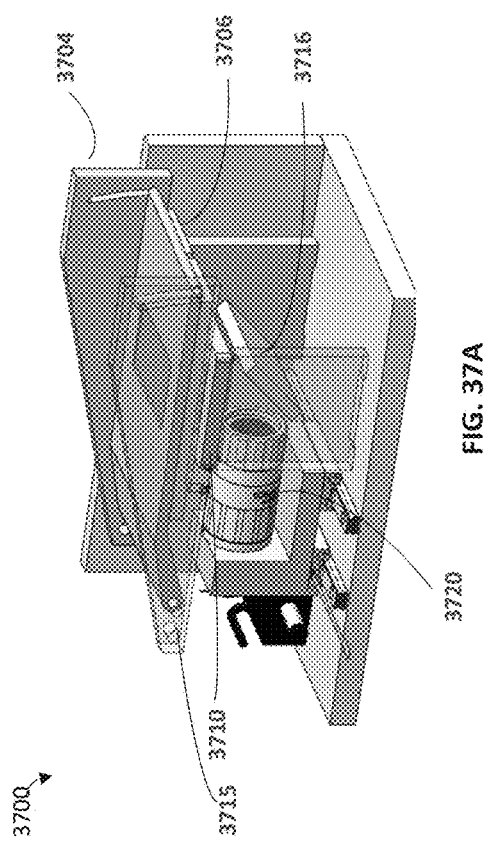
FIG. 37A shows a perspective view of an example sample handling apparatus in a closed position.

FIG. 37A is a perspective view of an example sample handling apparatus 3700 (also referred to herein as a support device, a sample holder, and an array alignment device) in a closed position in accordance with some example implementations. As shown, the sample handling apparatus 3700 includes a first member 3704, a second member 3710, optionally an image capture device 3720, a first substrate 3706, optionally a hinge 3715, and optionally a mirror 3716. The hinge 3715 may be configured to allow the first member 3704 to be positioned in an open or closed configuration by opening and/or closing the first member 3704 in a clamshell manner along the hinge 3715.

Figure 37B:
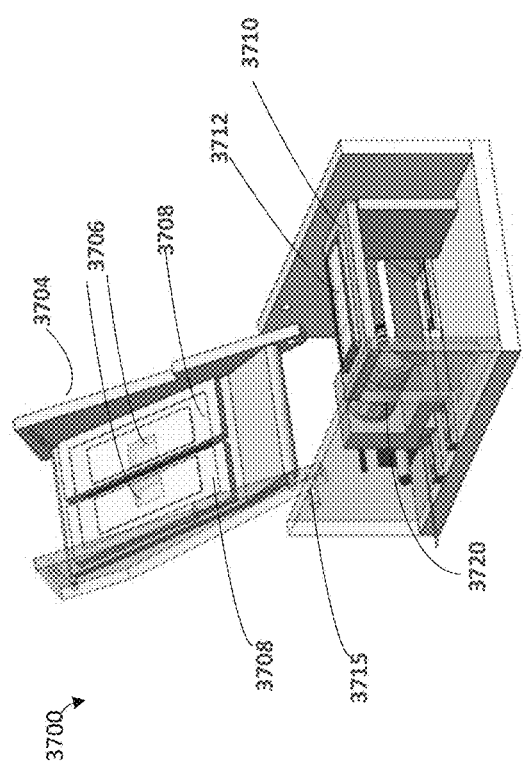
FIG. 37B shows a perspective view of the example sample handling apparatus in an open position.

FIG. 37B is a perspective view of the example sample handling apparatus 3700 in an open position in accordance with some example implementations. As shown, the sample handling apparatus 3700 includes one or more first retaining mechanisms 3708 configured to retain one or more first substrates 3706. In the example of FIG. 37B, the first member 3704 is configured to retain two first substrates 3706, however the first member 3704 may be configured to retain more or fewer first substrates 3706.

In some aspects, when the sample handling apparatus 3700 is in an open position (as in FIG. 37B), the first substrate 3706 and/or the second substrate 3712 may be loaded and positioned within the sample handling apparatus 3700 such as within the first member 3704 and the second member 3710, respectively. As noted, the hinge 3715 may allow the first member 3704 to close over the second member 3710 and form a sandwich configuration (e.g., the sandwich configuration shown in FIG. 23).

In some aspects, after the first member 3704 closes over the second member 3710, an alignment mechanism (not shown) of the sample handling apparatus 3700 may actuate the first member 3704 and/or the second member 3710 to form the sandwich configuration for the permeabilization step (e.g., bringing the first substrate 3706 and the second substrate 3712 closer to each other and within a threshold distance for the sandwich configuration). The alignment mechanism may be configured to control a speed, an angle, or the like of the sandwich configuration.

In some embodiments, the biological sample (e.g., tissue sample 2302 of FIG. 23) may be aligned within the first member 3704 (e.g., via the first retaining mechanism 3708) prior to closing the first member 3704 such that a desired region of interest of the sample 2302 is aligned with the barcoded array of the second substrate (e.g., the slide 2304), e.g., when the first and second substrates are aligned in the sandwich configuration. Note that element numbers "37XX" refer to elements from FIGS. 37A and 37B and element numbers "23XX" refer to elements in FIG. 23, wherein "XX" is any two digits. Such alignment may be accomplished manually (e.g., by a user) or automatically (e.g., via an automated alignment mechanism). After or before alignment, spacers may be applied to the first substrate 3706 and/or the second substrate 3712 to maintain a minimum spacing between the first substrate 3706 and the second substrate 3712 during sandwiching. In some aspects, the reagent medium (e.g., reagent medium 2305) may be applied to the first substrate 3706 and/or the second substrate 3712. The first member 3704 may then close over the second member 3710 and form the sandwich configuration. Analytes (including derivatives such as RTL ligation products and/or analyte capture agents) 2308 may be captured by the capture probes 2306 and may be processed for spatial analysis.

In some embodiments, during the permeabilization step, the image capture device 3720 may capture images of the overlap area between the tissue 2302 and the capture probes 2306. If more than one first substrates 3706 and/or second substrates 3712 are present within the sample handling apparatus 3700, the image capture device 3720 may be configured to capture one or more images of one or more overlap areas. Further details on support devices, sample holders, sample handling apparatuses, or systems for implementing a sandwiching process are described in, e.g., PCT Publ. No. WO 2021/0189475 and PCT/US2021/050931, each of which are incorporated by reference in their entirety.

Analytes within a biological sample may be released through disruption (e.g., permeabilization, digestion, etc.) of the biological sample or may be released without disruption. Various methods of permeabilizing (e.g., any of the permeabilization reagents and/or conditions described herein) a biological sample are described herein, including for example including the use of various detergents, buffers, proteases, and/or nucleases for different periods of time and at various temperatures. Additionally, various methods of delivering fluids (e.g., a buffer, a permeabilization solution) to a biological sample are described herein including the use of a substrate holder (e.g., for sandwich assembly, sandwich configuration, as described herein)

Provided herein are methods for delivering a fluid to a biological sample disposed on an area of a first substrate and an array disposed on a second substrate.

In some embodiments and with reference to FIG. 23, the sandwich configuration described herein between a first substrate comprising a biological sample (e.g., slide 2303) and a second substrate comprising a spatially barcoded array (e.g., slide 2304 with barcoded capture probes 2306) may include a reagent medium (e.g., a liquid reagent medium, e.g., a permeabilization solution 2305 or other target molecule release and capture solution) to fill a gap (e.g., gap 2307). It may be desirable that the reagent medium be free from air bubbles between the slides to facilitate transfer of target molecules with spatial information. Additionally, air bubbles present between the slides may obscure at least a portion of an image capture of a desired region of interest. Accordingly, it may be desirable to ensure or encourage suppression and/or elimination of air bubbles between the two substrates (e.g., slide 2303 and slide 2304) during a permeabilization step.

In some aspects, it may be possible to reduce or eliminate bubble formation between the slides using a variety of filling methods and/or closing methods.

Workflows described herein may include contacting a drop of the reagent medium (e.g., liquid reagent medium, e.g., a permeabilization solution 2305) disposed on a first substrate or a second substrate with at least a portion of the second substrate or first substrate, respectively. In some embodiments, the contacting comprises bringing the two substrates into proximity such that the sample on the first substrate is aligned with the barcode array of capture probes on the second substrate.

In some embodiments, the drop includes permeabilization reagents (e.g., any of the permeabilization reagents described herein). In some embodiments, the rate of permeabilization of the biological sample is modulated by delivering the permeabilization reagents (e.g., a fluid containing permeabilization reagents) at various temperatures.

In the example sandwich maker workflows described herein, the reagent medium (e.g., liquid reagent medium, permeabilization solution 2305) may fill a gap (e.g., the gap 2307) between a first substrate (e.g., slide 2303) and a second substrate (e.g., slide 2304 with barcoded capture probes 2306) to warrant or enable transfer of target molecules with spatial information. Described herein are examples of filling methods that may suppress bubble formation and suppress undesirable flow of transcripts and/or target molecules or analytes. Robust fluidics in the sandwich making described herein may preserve spatial information by reducing or preventing deflection of molecules as they move from the tissue slide to the capture slide.

FIG. 38A shows an exemplary sandwiching process 3800 where a first substrate (e.g., slide 3803), including a biological sample 3802 (e.g., a tissue section), and a second substrate (e.g., slide 3804 including spatially barcoded capture probes 3806) are brought into proximity with one another. As shown in FIG. 38A a liquid reagent drop (e.g., permeabilization solution 3805) is introduced on the second substrate in proximity to the capture probes 3806 and in between the biological sample 3802 and the second substrate (e.g., slide 3804 including spatially barcoded capture probes 3806). The permeabilization solution 3805 may release analytes that can be captured by the capture probes 3806 of the array. As further shown, one or more spacers 3810 may be positioned between the first substrate (e.g., slide 3803) and the second substrate (e.g., slide 3804 including spatially barcoded capture probes 3806). The one or more spacers 3810 may be configured to maintain a separation distance between the first substrate and the second substrate. While the one or more spacers 3810 is shown as disposed on the second substrate, the spacer may additionally or alternatively be disposed on the first substrate.

In some embodiments, the one or more spacers 3810 is configured to maintain a separation distance between first and second substrates that is between about 2 microns and 1 mm (e.g., between about 2 microns and 800 microns, between about 2 microns and 700 microns, between about 2 microns and 600 microns, between about 2 microns and 500 microns, between about 2 microns and 400 microns, between about 2 microns and 300 microns, between about 2 microns and 200 microns, between about 2 microns and 100 microns, between about 2 microns and 25 microns, or between about 2 microns and 10 microns), measured in a direction orthogonal to the surface of first substrate that supports the sample. In some instances, the separation distance is about 2, 3, 4, 5, 6, 7, 8, 9, 10, 11, 12, 13, 14, 15, 16, 17, 18, 19, 20, 21, 22, 23, 24, or 25 microns. In some embodiments, the separation distance is less than 50 microns. In some embodiments, the separation distance is less than 25 microns. In some embodiments, the separation distance is less than 20 microns. The separation distance may include a distance of at least 2 μm.

FIG. 38B shows a fully formed sandwich configuration creating a chamber 3650 formed from the one or more spacers 3610, the first substrate (e.g., the slide 303), and the second substrate (e.g., the slide 304 including spatially barcoded capture probes 306) in accordance with some example implementations. In the example of FIG. 38B, the liquid reagent (e.g., the permeabilization solution 305) fills the volume of the chamber 3650 and may create a permeabilization buffer that allows analytes, RTL ligation products, and analyte capture agents to diffuse from the biological sample 302 toward the capture probes 306 of the second substrate (e.g., slide 3804). In some aspects, flow of the permeabilization buffer may deflect transcripts and/or molecules from the biological sample 3802 and may affect diffusive transfer of analytes for spatial analysis. A partially or fully sealed chamber 3850 resulting from the one or more spacers 3810, the first substrate, and the second substrate may reduce or prevent flow from undesirable convective movement of transcripts and/or molecules over the diffusive transfer from the biological sample 3802 to the capture probes 3806.

In some instances, the first substrate and the second substrate are arranged in an angled sandwich assembly as described herein. For example, during the sandwiching of the two substrates (e.g., the slide 3803 and the slide 3804), an angled closure workflow may be used to suppress or eliminate bubble formation.

Figures 39A, 39B, 39C:
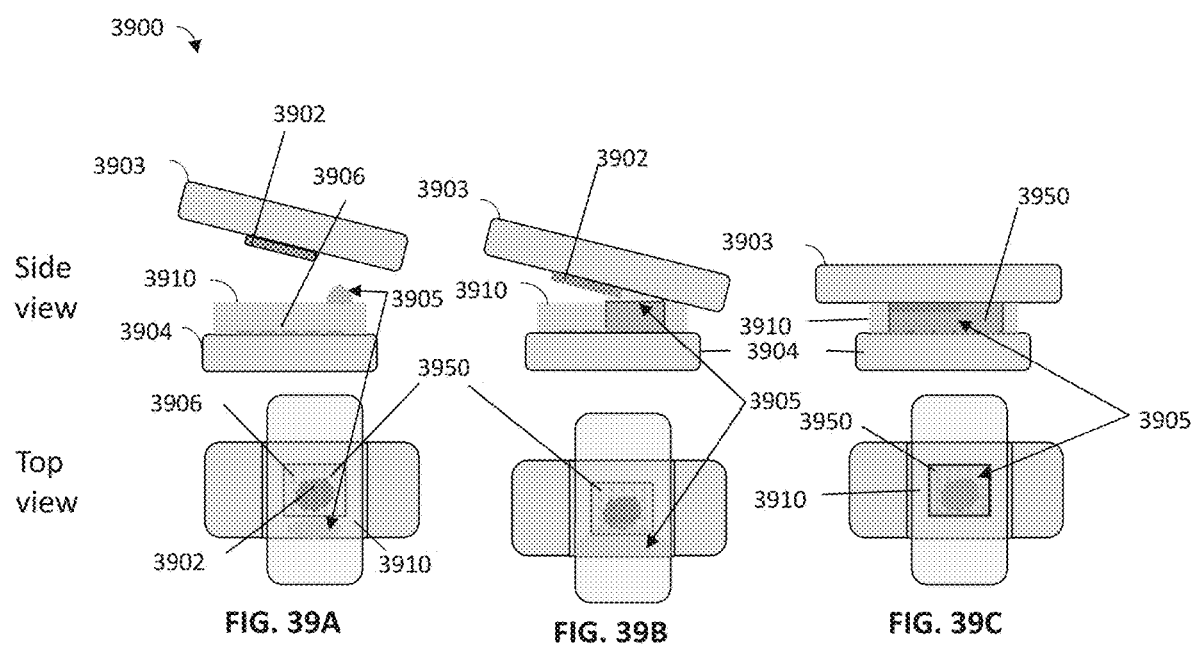
FIG. 39A shows the first substrate angled over (superior to) the second substrate.
FIG. 39B shows that as the first substrate lowers, and/or as the second substrate rises, the dropped side of the first substrate may contact the drop of the reagent medium.
FIG. 39C shows a full closure of the sandwich between the first substrate and the second substrate with the spacer contacting both the first substrate and the second substrate.

FIGS. 39A-39C depict a side view and a top view of an exemplary angled closure workflow 3900 for sandwiching a first substrate (e.g., slide 3903) having a biological sample 3902 and a second substrate (e.g., slide 3904 having capture probes 3906) in accordance with some example implementations.

FIG. 39A depicts the first substrate (e.g., the slide 3903 including biological sample 3902) angled over (superior to) the second substrate (e.g., slide 3904). As shown, a drop of the reagent medium (e.g., permeabilization solution) 3905 is located on the spacer 3910 toward the right-hand side of the side view in FIG. 39A. While FIG. 39A depicts the reagent medium on the right hand side of side view, it should be understood that such depiction is not meant to be limiting as to the location of the reagent medium on the spacer.

FIG. 39B shows that as the first substrate lowers, and/or as the second substrate rises, the dropped side of the first substrate (e.g., a side of the slide 3903 angled toward the second substrate) may contact the drop of the reagent medium 3905. The dropped side of the first substrate may urge the reagent medium 3905 toward the opposite direction (e.g., towards an opposite side of the spacer 3910, towards an opposite side of the first substrate relative to the dropped side). For example, in the side view of FIG. 39B the reagent medium 3905 may be urged from right to left as the sandwich is formed.

In some embodiments, the first substrate and/or the second substrate are further moved to achieve an approximately parallel arrangement of the first substrate and the second substrate.

FIG. 39C depicts a full closure of the sandwich between the first substrate and the second substrate with the spacer 3910 contacting both the first substrate and the second substrate and maintaining a separation distance and optionally the approximately parallel arrangement between the two substrates. As shown in the top view of FIG. 39C, the spacer 3910 fully encloses and surrounds the biological sample 3902 and the capture probes 3906, and the spacer 3910 forms the sides of chamber 3950 which holds a volume of the reagent medium 3905.

It should be understood that while FIGS. 39A-39C depict the first substrate (e.g., the slide 3903 including biological sample 3902) angled over (superior to) the second substrate (e.g., slide 3904) and the second substrate comprising the spacer 3910, it should be understood that an exemplary angled closure workflow can include the second substrate angled over (superior to) the first substrate and the first substrate comprising the spacer 3910.

Figures 40A, 40B, 40C, 40D, 40E:
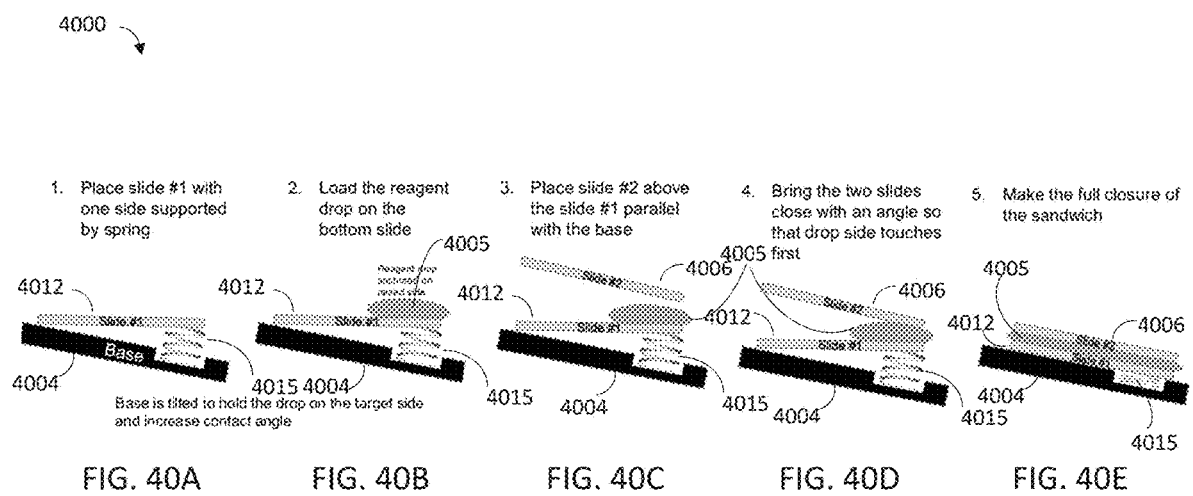
FIGS. 40A-40E show an example workflow for an angled sandwich assembly.

FIGS. 40A-40E depict an example workflow 4000 for an angled sandwich assembly in accordance with some example implementations. As shown in FIG. 40A, a substrate 4012 (e.g., comprising a first substrate such as slide 2303 or a second substrate such as slide 2304 comprising spatially barcoded capture probes 2306, as shown in FIG. 23) may be positioned and placed on a base 4004 (e.g., a first member or a second member of a sample holder disclosed herein) with a side of the substrate 4012 supported by a spring 4015. The spring 4015 may extend from the base 4004 in a superior direction and may be configured to dispose the substrate 4012 along a plane angled differently than the base 4004. The angle of the substrate 4012 may be such that a drop of reagent medium 4005 (e.g., drop of liquid reagent medium) placed on the surface of the substrate 4012 (e.g., a surface of a spacer attached to the substrate) will not fall off the surface (e.g., due to gravity). The angle may be determined based on a gravitational force versus any surface force to move the drop away from and off the substrate 4012.

FIG. 40B depicts a drop 4005 of reagent medium placed on the substrate 4012. As shown, the drop 4005 is located on the side of the substrate 4012 contacting the spring 4015 and is located in proximity and above (superior to) the spring 4015.

As shown in FIG. 40C, another substrate 4006 may be positioned above (superior to) the substrate 4012 and at an angle substantially parallel with the base 4004. For example, in cases wherein substrate 4012 is a second substrate disclosed herein (e.g., slide 2304 from FIG. 23 comprising spatially barcoded capture probes), substrate 4006 may be a first substrate disclosed herein (e.g., slide 2303). In cases wherein substrate 4012 is a first substrate disclosed herein (e.g., slide 2303), substrate 4006 may be a second substrate (e.g., slide 2304 comprising spatially barcoded capture probes).

In some cases, another base (not shown) supporting substrate 4006 (e.g., a first member or a second member of a sample holder disclosed herein) may be configured to retain substrate 1706 at the angle substantially parallel to the base 4004.

As shown in FIG. 40D, substrate 4006 may be lowered toward the substrate 4012 such that a dropped side of the substrate 4006 contacts the drop 4005 first. In some aspects, the dropped side of the substrate 4006 may urge the drop 4005 toward the opposite side of the substrate 4006. In some embodiments, the substrate 4012 may be moved upward toward the substrate 4006 to accomplish the contacting of the dropped side of the substrate 4006 with the drop 4005.

FIG. 40E depicts a full sandwich closure of the substrate 4006 and the substrate 4012 with the drop of reagent medium 4005 positioned between the two sides. In some aspects and as shown, as the substrate 4006 is lowered onto the drop 4005 and toward the substrate 4012 (and/or as the substrate 4012 is raised up toward the substrate 4006), the spring 4015 may compress and the substrate 4012 may lower to the base 4004 and become substantially parallel with the substrate 4006.

Figures 41A, 41B:
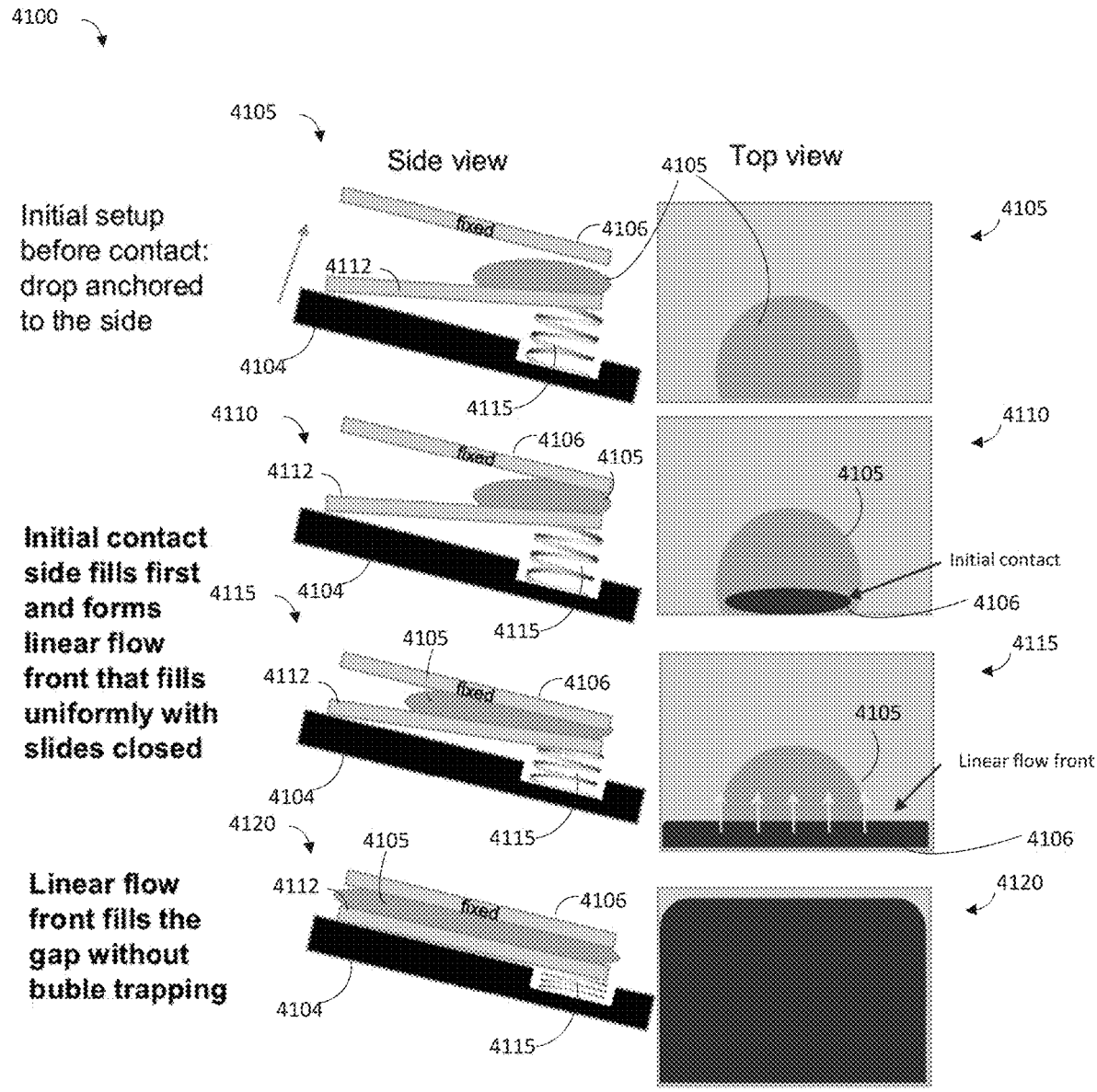
FIG. 41A shows a side view of the angled closure workflow.
FIG. 41B shows a top view of the angled closure workflow.

FIG. 41A is a side view of the angled closure workflow 4100 in accordance with some example implementations. FIG. 41B is a top view of the angled closure workflow 4100 in accordance with some example implementations. As shown at 4105 and in accordance with FIGS. 40C-40D, the drop of reagent medium 4105 is positioned to the side of the substrate 4112 contacting the spring 4115.

At step 4110, the dropped side of the angled substrate 4106 contacts the drop of reagent medium 4105 first. The contact of the substrate 4106 with the drop of reagent medium 4105 may form a linear or low curvature flow front that fills uniformly with the slides closed.

At step 4115, the substrate 4106 is further lowered toward the substrate 4112 (or the substrate 4112 is raised up toward the substrate 4106) and the dropped side of the substrate 4106 may contact and may urge the liquid reagent toward the side opposite the dropped side and creating a linear or low curvature flow front that may prevent or reduce bubble trapping between the slides. As further shown, the spring 4115 may begin to compress as the substrate 4106 is lowered.

At step 4120, the drop of reagent medium 4105 fills the gap (e.g., the gap 2307 as shown in FIG. 23) between the substrate 4106 and the substrate 4112. The linear flow front of the liquid reagent may form by squeezing the drop 4105 volume along the contact side of the substrate 4112 and/or the substrate 4106. Additionally, capillary flow may also contribute to filling the gap area. As further shown in step 4120, the spring 4115 may be fully compressed such that the substrate 4106, the substrate 4112, and the base 4104 are substantially parallel to each other.

In some aspects, an angled closure workflow disclosed herein (e.g., FOREMAN HUB FIGS. 39A-39C, 40A-40E, and 41A-41B) may be performed by a sample handling apparatus (e.g., as described in PCT/US2021/050931, which is hereby incorporated by reference in its entirety.

Further details on angled closure workflows, and devices and systems for implementing an angled closure workflow, are described in PCT/US2021/036788 and PCT/US2021/050931, which are hereby incorporated by reference in their entirety.

Additional configurations for reducing or eliminating bubble formation, and/or for reducing unwanted fluid flow, are described in PCT/US2021/036788, which is hereby incorporated by reference in its entirety.

In some embodiments, the reagent medium comprises a permeabilization agent. Suitable agents for this purpose include, but are not limited to, organic solvents (e.g., acetone, ethanol, and methanol), cross-linking agents (e.g., paraformaldehyde), detergents (e.g., saponin, Triton X-100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroylsarcosine sodium salt solution). Exemplary permeabilization reagents are described in in PCT Patent Application Publication No. WO 2020/123320, which is incorporated by reference in its entirety.

In some embodiments, the reagent medium comprises a lysis reagent. Lysis solutions can include ionic surfactants such as, for example, sarkosyl and sodium dodecyl sulfate (SDS). More generally, chemical lysis agents can include, without limitation, organic solvents, chelating agents, detergents, surfactants, and chaotropic agents. Exemplary lysis reagents are described in PCT Patent Application Publication No. WO 2020/123320, which is incorporated by reference in its entirety.

In some embodiments, the reagent medium comprises a protease. Exemplary proteases include, e.g., pepsin, trypsin, pepsin, elastase, and proteinase K. Exemplary proteases are described in PCT Patent Application Publication No. WO 2020/123320, which is incorporated by reference in its entirety.

In some embodiments, the reagent medium comprises a detergent. Exemplary detergents include sodium dodecyl sulfate (SDS), sarkosyl, saponin, Triton X-100™, and Tween-20™. Exemplary detergents are described in PCT Patent Application Publication No. WO 2020/123320, which is incorporated by reference in its entirety.

In some embodiments, the reagent medium comprises a nuclease. In some embodiments, the nuclease comprises am RNase. In some embodiments, the RNase is selected from RNase A, RNase C, RNase H, and RNase I. In some embodiments, the reagent medium comprises one or more of sodium dodecyl sulfate (SDS), proteinase K, pepsin, N-lauroylsarcosine, RNAse, and a sodium salt thereof.

The sample holder is compatible with a variety of different schemes for contacting the aligned portions of the biological sample and array with the reagent medium to promote analyte capture. In some embodiments, the reagent medium is deposited directly on the second substrate (e.g., forming a reagent medium that includes the permeabilization reagent and the feature array), and/or directly on the first substrate. In some embodiments, the reagent medium is deposited on the first and/or second substrate, and then the first and second substrates aligned in the sandwich configuration such that the reagent medium contacts the aligned portions of the biological sample and array. In some embodiments, the reagent medium is introduced into the gap 2307 while the first and second substrates are aligned in the sandwich configuration.

In certain embodiments a dried permeabilization reagent is applied or formed as a layer on the first substrate or the second substrate or both prior to contacting the sample and the feature array. For example, a reagent can be deposited in solution on the first substrate or the second substrate or both and then dried. Drying methods include, but are not limited to spin coating a thin solution of the reagent and then evaporating a solvent included in the reagent or the reagent itself. Alternatively, in other embodiments, the reagent can be applied in dried form directly onto the first substrate or the second substrate or both. In some embodiments, the coating process can be done in advance of the analytical workflow and the first substrate and the second substrate can be stored pre-coated. Alternatively, the coating process can be done as part of the analytical workflow. In some embodiments, the reagent is a permeabilization reagent. In some embodiments, the reagent is a permeabilization enzyme, a buffer, a detergent, or any combination thereof. In some embodiments, the permeabilization enzyme is pepsin. In some embodiments, the reagent is a dried reagent (e.g., a reagent free from moisture or liquid). In some instances, the substrate that includes the sample (e.g., a histological tissue section) is hydrated. The sample can be hydrated by contacting the sample with a reagent medium, e.g., a buffer that does not include a permeabilization reagent. In some embodiments, the hydration is performed while the first and second substrates are aligned in a sandwich configuration.

In some instances, the aligned portions of the biological sample and the array are in contact with the reagent medium 2305 for about 1 minute. In some instances, the aligned portions of the biological sample and the array are in contact with the reagent medium 2305 for about 5 minutes. In some instances, the aligned portions of the biological sample and the array are in contact with the reagent medium 1205 in the gap 1207 for about 1 minute, about 5 minutes, about 10 minutes, about 12 minutes, about 15 minutes, about 18 minutes, about 20 minutes, about 25 minutes, about 30 minutes, about 36 minutes, about 45 minutes, or about an hour. In some instances, the aligned portions of the biological sample and the array are in contact with the reagent medium 2305 for about 1-60 minutes. In some instances, the aligned portions of the biological sample and the array are in contact with the reagent medium 2305 for about 30 minutes.

In some embodiments, following initial contact between sample and a permeabilization agent, the permeabilization agent can be removed from contact with sample (e.g., by opening sample holder) before complete permeabilization of sample. For example, in some embodiments, only a portion of sample is permeabilized, and only a portion of the analytes in sample may be captured by feature array. In some instances, the reduced amount of analyte captured and available for detection can be offset by the reduction in lateral diffusion that results from incomplete permeabilization of sample. In general, the spatial resolution of the assay is determined by the extent of analyte diffusion in the transverse direction (i.e., orthogonal to the normal direction to the surface of sample). The larger the distance between the sample on the first substrate and the feature array on the second substrate, the greater the extent of diffusion in the transverse direction, and the concomitant loss of resolution. Analytes liberated from a portion of the sample closest to the feature array have a shorter diffusion path, and therefore do not diffuse as far laterally as analytes from portions of the sample farthest from the feature array. As a result, in some instances, incomplete permeabilization of the sample (by reducing the contact interval between the permeabilization agent and the sample) can be used to maintain adequate spatial resolution in the assay.

In some instances, the device is configured to control a temperature of the first and second substrates. In some embodiments, the temperature of the first and second members is lowered to a first temperature that is below room temperature (e.g., 25 degrees Celsius) (e.g., 20 degrees Celsius or lower, 15 degrees Celsius or lower, 10 degrees Celsius or lower, 5 degrees Celsius or lower, 4 degrees Celsius or lower, 3 degrees Celsius or lower, 2 degrees Celsius or lower, 1 degree Celsius or lower, 0 degrees Celsius or lower, −1 degrees Celsius or lower, −5 degrees Celsius or lower). In some embodiments, the device includes a temperature control system (e.g., heating and cooling conducting coils) to control the temperature of the sample holder. Alternatively, in other embodiments, the temperature of the sample holder is controlled externally (e.g., via refrigeration or a hotplate). In a first step, the second member, set to or at the first temperature, contacts the first substrate, and the first member, set to or at the first temperature, contacts the second substrate, thereby lowering the temperature of the first substrate and the second substrate to a second temperature. In some embodiments, the second temperature is equivalent to the first temperature. In some embodiments, the first temperature is lower than room temperature (e.g., 25 degrees Celsius). In some embodiments, the second temperature ranges from about −10 degrees Celsius to about 4 degrees Celsius. In some embodiments, the second temperature is below room temperature (e.g., 25 degrees Celsius) (e.g., 20 degrees Celsius or lower, 15 degrees Celsius or lower, 10 degrees Celsius or lower, 5 degrees Celsius or lower, 4 degrees Celsius or lower, 3 degrees Celsius or lower, 2 degrees Celsius or lower, 1 degree Celsius or lower, 0 degrees Celsius or lower, −1 degrees Celsius or lower, −5 degrees Celsius or lower).

In an exemplary embodiment, the second substrate is contacted with the permeabilization reagent. In some embodiments, the permeabilization reagent is dried. In some embodiments, the permeabilization reagent is a gel or a liquid. Also in the exemplary embodiment, the biological sample is contacted with buffer. Both the first and second substrates are placed at lower temperature to slow down diffusion and permeabilization efficiency. Alternatively, in some embodiments, the sample can be contacted directly with a liquid permeabilization reagent without inducing an unwanted initiation of permeabilization due to the substrates being at the second temperature. In some embodiments, the low temperature slows down or prevents the initiation of permeabilization. In a second step, keeping the sample holder and substrates at a cold temperature (e.g., at the first or second temperatures) continues to slow down or prevent the permeabilization of the sample. In a third step, the sample holder (and consequently the first and second substrates) is heated up to initiate permeabilization. In some embodiments, the sample holder is heated up to a third temperature. In some embodiments, the third temperature is above room temperature (e.g., 25 degrees Celsius) (e.g., 30 degrees Celsius or higher, 35 degrees Celsius or higher, 40 degrees Celsius or higher, 50 degrees Celsius or higher, 60 degrees Celsius or higher). In some embodiments, analytes that are released from the permeabilized tissue of the sample diffuse to the surface of the second substrate and are captured on the array (e.g., barcoded probes) of the second substrate. In a fourth step, the first substrate and the second substrate are separated (e.g., pulled apart) and temperature control is stopped.

In some embodiments, where either the first substrate or substrate second (or both) includes wells, a permeabilization solution can be introduced into some or all of the wells, and then the sample and the feature array can be contacted by closing the sample holder to permeabilize the sample. In certain embodiments, a permeabilization solution can be soaked into a hydrogel film that is applied directly to the sample, and/or soaked into features (e.g., beads) of the array. When the first and second substrates are aligned in the sandwich configuration, the permeabilization solution promotes migration of analytes from the sample to the array.

In certain embodiments, different permeabilization agents or different concentrations of permeabilization agents can be infused into array features (e.g., beads) or into a hydrogel layer as described above. By locally varying the nature of the permeabilization reagent(s), the process of analyte capture from the sample can be spatially adjusted.

In some instances, migration of the analyte from the biological sample to the second substrate is passive (e.g., via diffusion). Alternatively, in certain embodiments, migration of the analyte from the biological sample is performed actively (e.g., electrophoretic, by applying an electric field to promote migration). In some instances, first and second substrates can include a conductive epoxy. Electrical wires from a power supply can connect to the conductive epoxy, thereby allowing a user to apply a current and generate an electric field between the first and second substrates. In some embodiments, electrophoretic migration results in higher analyte capture efficiency and better spatial fidelity of captured analytes (e.g., on a feature array) than random diffusion onto matched substrates without the application of an electric field (e.g., via manual alignment of the two substrates). Exemplary methods of electrophoretic migration, including those illustrated in FIGS. 7-11C, are described in WO 2020/176788, including at FIGS. 13-15, 24A-24B, and 25A-25C, which is hereby incorporated by reference in its entirety.

Loss of spatial resolution can occur when analytes migrate from the sample to the feature array and a component of diffusive migration occurs in the transverse (e.g., lateral) direction, approximately parallel to the surface of the first substrate on which the sample is mounted. To address this loss of resolution, in some embodiments, a permeabilization agent deposited on or infused into a material with anisotropic diffusion can be applied to the sample or to the feature array. The first and second substrates are aligned by the sample holder and brought into contact. A permeabilization layer that includes a permeabilization solution infused into an anisotropic material is positioned on the second substrate.

In some embodiments, the feature array can be constructed atop a hydrogel layer infused with a permeabilization agent. The hydrogel layer can be mounted on the second substrate, or alternatively, the hydrogel layer itself may function as the second substrate. When the first and second substrates are aligned, the permeabilization agent diffuses out of the hydrogel layer and through or around the feature array to reach the sample. Analytes from the sample migrate to the feature array. Direct contact between the feature array and the sample helps to reduce lateral diffusion of the analytes, mitigating spatial resolution loss that would occur if the diffusive path of the analytes was longer.

Spatial analysis workflows can include a sandwiching process described herein, e.g., a process as described in FIG. 23. In some embodiments, the workflow includes provision of the first substrate comprising the biological sample. In some embodiments, the workflow includes, mounting the biological sample onto the first substrate. In some embodiments wherein the biological sample is a tissue sample, the workflow include sectioning of the tissue sample (e.g., cryostat sectioning). In some embodiments, the workflow includes a fixation step. In some instances, the fixation step can include fixation with methanol. In some instances, the fixation step includes formalin (e.g., 2% formalin).

In some embodiments, the biological sample on the first substrate is stained using any of the methods described herein. In some instances, the biological sample is imaged, capturing the stain pattern created during the stain step. In some instances, the biological sample then is destained prior to the sandwiching process.

The biological sample can be stained using known staining techniques, including, without limitation, Can-Grunwald, Giemsa, hematoxylin and eosin (H&E), hematoxylin, Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes biological staining using hematoxylin. In some embodiments, staining includes identifying analytes using fluorescently-conjugated antibodies, e.g., by immunofluorescence. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample. In some instances, a biological sample on the first substrate is stained.

In some instances, methods for immunofluorescence include a blocking step. The blocking step can include the use of blocking probes to decrease unspecific binding of the antibodies. The blocking step can optionally further include contacting the biological sample with a detergent. In some instances, the detergent can include Triton X-100™. The method can further include an antibody incubation step. In some embodiments, the antibody incubation step effects selective binding of the antibody to antigens of interest in the biological sample. In some embodiments, the antibody is conjugated to an oligonucleotide (e.g., an oligonucleotide-antibody conjugate as described herein). In some embodiments, the antibody is not conjugated to an oligonucleotide. In some embodiments, the method further comprises an antibody staining step. The antibody staining step can include a direct method of immunostaining in which a labelled antibody binds directly to the analyte being stained for. Alternatively, the antibody staining step can include an indirect method of immunostaining in which a first antibody binds to the analyte being stained for, and a second, labelled antibody binds to the first antibody. In some embodiments, the antibody staining step is performed prior to sandwich assembly. In some embodiments wherein an oligonucleotide-antibody conjugate is used in the antibody incubation step, the method does not comprise an antibody staining step.

In some instances, the methods include imaging the biological sample. In some instances, imaging occurs prior to sandwich assembly. In some instances, imaging occurs while the sandwich configuration is assembled. In some instances, imaging occurs during permeabilization of the biological sample. In some instances, image are captured using high resolution techniques (e.g., having 300 dots per square inch (dpi) or greater). For example, images can be captured using brightfield imaging (e.g., in the setting of hematoxylin or H&E stain), or using fluorescence microscopy to detect adhered labels. In some instances, high resolution images are captured temporally using e.g., confocal microscopy. In some instances, a low resolution image is captured. A low resolution image (e.g., images that are about 72 dpi and normally have an RGB color setting) can be captured at any point of the workflow, including but not limited to staining, destaining, permeabilization, sandwich assembly, and migration of the analytes. In some instances, a low resolution image is taken during permeabilization of the biological sample.

In some embodiments, the location of the one or more analytes in a biological sample are determined by immunofluorescence. In some embodiments, one or more detectable labels (e.g., fluorophore-labeled antibodies) bind to the one or more analytes that are captured (hybridized to) by a probe on the first slide and the location of the one or more analytes is determined by detecting the labels under suitable conditions. In some embodiments, one or more fluorophore-labeled antibodies are used to conjugate a moiety that associates with a probe on the first slide or the analyte that is hybridized to the probe on the first slide. In some instances, the location(s) of the one or more analytes is determined by imaging the fluorophore-labeled antibodies when the fluorophores are excited by a light of a suitable wavelength. In some embodiments, the location of the one or more analytes in the biological sample is determined by correlating the immunofluorescence data to an image of the biological sample. In some instances, the tissue is imaged throughout the permeabilization step.

In some instances, the biological samples can be destained. In some instances, destaining occurs prior to permeabilization of the biological sample. By way of example only, H&E staining can be destained by washing the sample in HCl. In some instances, the hematoxylin of the H&E stain is destained by washing the sample in HCl. In some embodiments, destaining can include 1, 2, 3, or more washes in HCl. In some embodiments, destaining can include adding HCl to a downstream solution (e.g., permeabilization solution).

Between any of the methods disclosed herein, the methods can include a wash step (e.g., with SSC (e.g., 0.1×SSC)). Wash steps can be performed once or multiple times (e.g., 1×, 2×, 3×, between steps disclosed herein). In some instances, wash steps are performed for about 10 seconds, about 15 seconds, about 20 seconds, about 30 seconds, or about a minute. In some instances, three washes occur for 20 seconds each. In some instances, the wash step occurs before staining the sample, after destaining the sample, before permeabilization the sample, after permeabilization the sample, or any combination thereof.

In some instances, after the sandwiching process the first substrate and the second substrate are separated (e.g., such that they are no longer aligned in a sandwich configuration, also referred to herein as opening the sandwich). In some embodiments, subsequent analysis (e.g., cDNA synthesis, library preparation, and sequences) can be performed on the captured analytes after the first substrate and the second substrate are separated.

In some embodiments, the process of transferring the ligation product or methylated-adaptor-containing nucleic acid from the first substrate to the second substrate is referred to interchangeably herein as a "sandwich process," "sandwiching process," or "sandwiching". The sandwich process is further described in PCT Patent Application Publication No. WO 2020/123320, PCT/US2021/036788, and PCT/US2021/050931, which are incorporated by reference in its entirety.

(e) Use of Multiplexed Sandwich Makers

This disclosure also provides methods, compositions, devices, and systems for using a single capture probe-containing to detect analytes from different biological samples (e.g., tissues) on different slides using serial sandwich processes. Thus, only one capture probe-containing array is necessary for the methods disclosed herein. In this way, as described herein, analytes from different samples or tissues can be captured serially and demultiplexed by sample-specific index sequences.

The methods include generating a connected probe (e.g., a ligation product) in multiple biological samples (i.e., a first sample, a second sample, a third sample, etc.). Generation of a connected probe (e.g., a ligation product) has been described above, and, the same methods are used herein to generate a connected probe (e.g., a ligation product) from analytes that are either protein analytes or nucleic acid (i.e., mRNA) analytes. That is, in some instances, the multiplexed sandwich maker methods disclosed herein can be used to detect protein analytes. In other instances, the multiplexed sandwich maker methods disclosed herein can be used to detect nucleic acid (i.e., mRNA) analytes.

The methods, compositions, devices, and systems include utilizing an analyte capture agent in multiple biological samples (i.e., a first sample, a second sample, a third sample, etc.). Using analyte capture agents for spatial detection has been described above, and, the same methods are used herein to use an analyte capture agent to identify analytes in a biological sample. In some embodiments, the multiplexed sandwich maker methods disclosed herein can be used to detect protein analytes.

As discussed below, each connected probe (e.g., a ligation product) that is generated or analyte capture agent includes a sample index sequence, which is a nucleotide sequence that is associated with a particular sample of origin in the multiplex sandwich methods. After generation of each connected probe (e.g., a ligation product) or analyte capture agent, each sample is serially sandwiched to an array or slide having a plurality of capture probes that can detect and hybridize to a capture probe binding domain from the connected probe (e.g., a ligation product) or analyte capture agent. During the sandwiching process, the indexed connected probe or analyte capture agent actively or passively migrates from the sample to the array for capture by a capture probe. Then the sandwich is opened, and the next sample is sandwiched with the array. In some embodiments, the array is washed prior to sandwiching with the next sample. Additional samples or tissues (e.g., 2 or more) can then be sandwiched with the array or slide having a plurality of capture probes, wherein connected probes (e.g., ligation products) or analyte capture agents from the additional samples or tissues can be transferred to the array in a similar manner. Because each sample includes a unique sample index, the sample of origin for each connected probe (e.g., a ligation product) or analyte capture agent that is captured on the array can be identified. In addition, the location of the connected probe (e.g., a ligation product) can be identified. In some embodiments, the location of the analyte capture agent can be identified. In some instances, the location is identified using fiducial markers on the gene expression slide (i.e., array) so that location of the ligation probe on the array mirrors the location of the sample on the sample slide. Exemplary fiducial markers are described in PCT Patent Application Publication No. WO 2020/123320, which is incorporated by reference in its entirety.

Such methods, compositions, devices, and systems allow for detection of analytes in multiple samples using only one gene expression slide and can be performed on any slide sample described herein. For example, in some instances, the biological sample is a formalin-fixed, paraffin-embedded (FFPE) sample, a frozen sample, or a fresh sample. In some instances, the biological sample is contacted with one or more stains. In some instances, the one or more stains include hematoxylin and eosin. In some instances, cell markers are detected using methods known in the art (e.g., using one or more optical labels such as fluorescent labels, radioactive labels, chemiluminescent labels, calorimetric labels, or colorimetric labels. In some instances, the biological sample is imaged before generating a connected probe (e.g., a ligation product) and before transferring the connected probe (e.g., a ligation product) to the gene expression slide.

The multiplex sandwich methods, compositions, devices, and systems described herein allow for detection of different types of samples and different analytes. For example in some instances, the samples used in the multiplex sandwich methods are from different species. In some instances, the samples used in the multiplex sandwich methods are from the same species but different individuals in the same species. In some instances, the samples used in the multiplex sandwich methods are from the same individual organism. In some instances, the samples are from different tissues or cell types. In some instances, the samples are from the same tissues or cell types. In some instances, the samples are from the same subject taken at different time points (e.g., before and after treatment). It is appreciated that the samples can be from any source so long as ligated products having sample index sequences unique to each sample are generated.

Multiple samples can be used in the methods described herein. For example, in some instances, at least two samples are used. In some instances, more than two samples (e.g., at least 3, 4, 5, 6, 7, 8, 9, 10, or more) samples are used in the methods disclosed herein. It is appreciated that each sample can be from different sources (e.g., different species, different organisms). In some embodiments, from each sample, the same gene is detected and identified. In some embodiments, for each sample, different genes are detected and identified.

In order to differentiate one sample from another, probe oligonucleotide for each sample in a multiplexed setting can include one or more unique sequences to identify the origin of the connected probe (e.g., a ligation product). In some instances, the unique sequence is a sample index sequence. In some instances, probe oligonucleotides for each sample include one or more (e.g., at least 1, 2, 3, 4, 5, or more) unique sample index sequence to identify the origin of the connected probe (e.g., a ligation product).

In some instances, the sample index is about 5 nucleotides to about 50 nucleotides long (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotides long. In some embodiments, the sample index is about 5-15 nucleotides long. In some embodiments, the sample index is about 10-12 nucleotides long. Both synthetic and/or naturally-occurring nucleotides can be used to generate a sample index sequence. It is appreciated that any sequence can be designed so long as it is unique among other sample index sequences and optionally that it can be distinguished from any sequence in the genome of the sample.

Figure 12A:
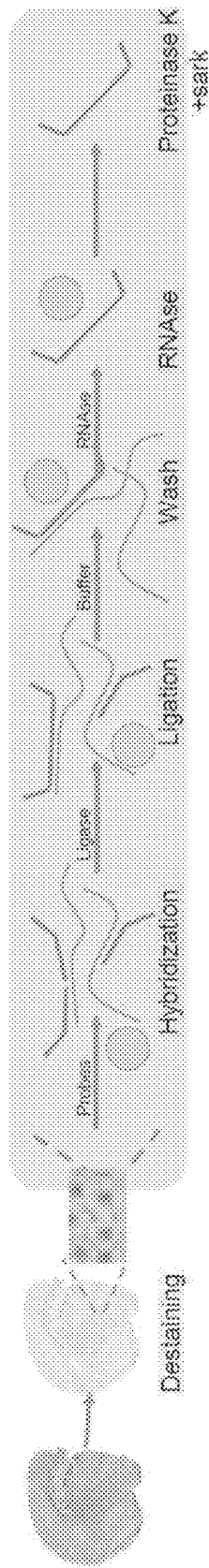
FIG. 12A shows an exemplary workflow for using ligated probes to capture intracellular analytes.

A sample index sequence can be located anywhere on the connected probe (e.g., a ligation product) so long as it does not affect (1) hybridization of the probe oligonucleotides to the analyte, (2) ligation of the probe oligonucleotides to generate the connected probe (e.g., a ligation product), and (3) hybridization of the capture probe binding domain to the capture probe on an array. For example, in some instances, the sample index sequence can be located on the first probe oligonucleotide (e.g., the left hand probe; i.e., as shown in FIG. 12A). In some instances, the sample index is located on the flap of the first probe oligonucleotide that does not hybridize to the analyte. In some instances, the sample index sequence can be located on the second probe oligonucleotide (e.g., the right hand probe; i.e., as shown in FIG. 12A). In some instances, the sample index is located on the flap of the second probe oligonucleotide that does not hybridize to the analyte.

(f) Systems and Kits

Also disclosed herein are systems and kits used for any one of the methods disclosed herein. In some instances, the system of kit is used for analyzing an analyte in a biological sample. In some instances, the system or kit includes a support device configured to retain a first substrate and a second substrate, wherein the biological sample is placed on the first substrate, and wherein the second substrate comprises a plurality of capture probes, wherein a capture probe of the plurality of capture probes comprises: (i) a spatial barcode and (ii) a capture domain. In some instances, the system or kit includes a first probe oligonucleotide and a second probe oligonucleotide, wherein the first probe oligonucleotide and the second probe oligonucleotide each comprise a sequence that is substantially complementary to adjacent sequences of the analyte, wherein the second probe oligonucleotide comprises a capture probe binding domain, and wherein the first probe oligonucleotide and the second probe oligonucleotide are capable of being ligated together to form a connected probe. In some instances, the system or kit includes a plurality of analyte capture agents, wherein an analyte capture agent of the plurality of analyte capture agents comprises an analyte binding moiety and a capture agent barcode domain, wherein the analyte binding moiety specifically binds to the analyte, and wherein the capture agent barcode domain comprises an analyte binding moiety barcode and an capture handle sequence. In some instances, the system or kit further includes a reagent medium comprising a permeabilization agent and optionally an agent for releasing the connected probe. In some instances, the system or kit includes instructions for performing any one of the methods described herein.

In some instances, the permeabilization agent is pepsin or proteinase K. In some instances, the agent for releasing the connected probe is an RNAse, optionally wherein the RNAse is RNAse H.

In some instances, the system or kit further includes an alignment mechanism on the support device to align the first substrate and the second substrate. In some instances, the alignment mechanism comprises a linear actuator and the first substrate comprises a first member and the second substrate comprises a second member. The linear actuator can be configured to move the second member along an axis orthogonal to the plane or the first member and/or the second member. The linear actuator can be configured to move the first member along an axis orthogonal to the plane of the first member and/or the second member. The linear actuator can be configured to move the first member, the second member, or both the first member and the second member at a velocity of at least 0.1 mm/sec. Finally, in some instances, the linear actuator can be configured to move the first member, the second member, or both the first member and the second member with an amount of force of at least 0.1 lbs.

EXAMPLES

Example 1—Methods for Capturing Connected Probes with Sandwich Process a. Methods of Capturing Connected Probes that Hybridize to Analytes in a Mouse Brain and Mouse Kidney Samples Using Probe Pairs that Hybridize to a Fraction of the Mouse Transcriptome.

In a non-limiting example, mouse brain and mouse kidney FFPE sections on standard slides (for sandwich conditions) or gene expression (GEx) slides (for non-sandwich control conditions) were deparaffinized, H&E stained, and imaged. Next, the tissue samples were hematoxylin-destained with three HCl solution washes. The sections were then decrosslinked by incubating at 70° C. for 1 hour in TE pH 9.0. TE was removed and the tissues were incubation in 1×PBS-Tween for 15 minutes.

Individual probe oligonucleotides (e.g., a first probe oligonucleotide, a second probe oligonucleotide) of probe pairs were hybridized to adjacent sequences of an analyte (e.g., an RNA molecule) in the mouse brain tissue. The RTL probe oligonucleotides were then ligated together, thereby creating a connected probe (e.g., a ligation product) (FIG. 12A). The connected probe (e.g., a ligation product) included a capture probe binding domain. The probes were designed to hybridize to part of the mouse transcriptome (e.g., using 5000 total probe pairs) or to hybridize to each transcript in the mouse transcriptome.

Figure 12B:
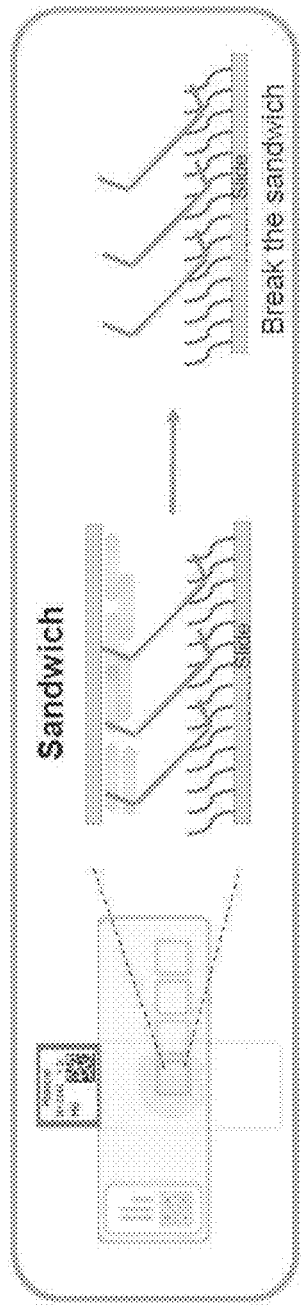
FIG. 12B shows an exemplary schematic illustrating the tissue sample sandwiched between a substrate and a spatially-barcoded capture probe array, wherein the ligated probes are transferred to the spatially-barcoded capture probe array.

After ligation of the RTL probe oligonucleotides, the connected probes were released from the tissue using various conditions: (A) sandwich process with RNase in the reagent medium; (B) sandwich process with RNAse+Proteinase K in the reagent medium; or (C) without sandwich methods (i.e., a control). For sandwich conditions A and B, the tissue mounted standard slides were aligned with a GEx slide and permeabilized in the sandwich configuration as described herein (see, e.g., FIG. 12B). For the non-sandwich condition C, the tissue mounted on the GEx slides were permeabilized directly on the GEx array. Following permeabilization, the capture probes were extended, sequencing libraries were prepared and sequenced, and the results were analyzed computationally.

Table 1 and Table 2 below show results of the mouse brain 5000 probe pair experiment.

TABLE 1

| Conditions | Valid Barcodes | Valid UMIs | Fraction targeted reads usable | Reads Mapped Confidently to Transcriptome | Fraction Reads in Spots Under Tissue | Fraction reads unmapped |
| --- | --- | --- | --- | --- | --- | --- |
| RNAse only (30 mins) mouse brain | 97.5% | 100.0% | 82.8% | 92.0% | 91.9% | 4.8% |
| RNAse + Proteinase K (30 mins) mouse brain | 97.6% | 100.0% | 86.1% | 91.1% | 96.4% | 5.6% |
| RNAse + Proteinase K + Sarkosyl (30 mins) mouse brain | 97.0% | 100.0% | 83.6% | 89.2% | 96.0% | 6.7% |
| Control mouse brain (RTL but no sandwich methods) | 97.1% | 100.0% | 63.8% | 84.2% | 77.9% | 11.6% |

TABLE 2

| Conditions | Median panel genes detected at 260 panel reads per spot | Median panel UMI counts at 250 reads per spot | Median panel genes directed at 1000 panel reads per spot | Median panel UMI counts at 1000 panel reads per spot |
|---|---|---|---|---|
| RNAse only (30 mins) mouse brain | 90 | 123 | 134 | 201 |
| RNAse + Proteinase K (30 mins) mouse brain | 115 | 169 | 192 | 330 |
| RNAse + Proteinase K + Sarkosyl (30 mins) mouse brain | 47 | 63 | 57 | 79 |
| Control mouse brain (RTL but no sandwich methods) | 106 | 149 | 192 | 330 |

As shown in Table 1 and Table 2, the combination of RNAse+Proteinase K using sandwiching methods resulted in increased useable fraction targeted reads, increased reads in spots under tissues, and increased median panel genes and UMI counts.

Figure 13:
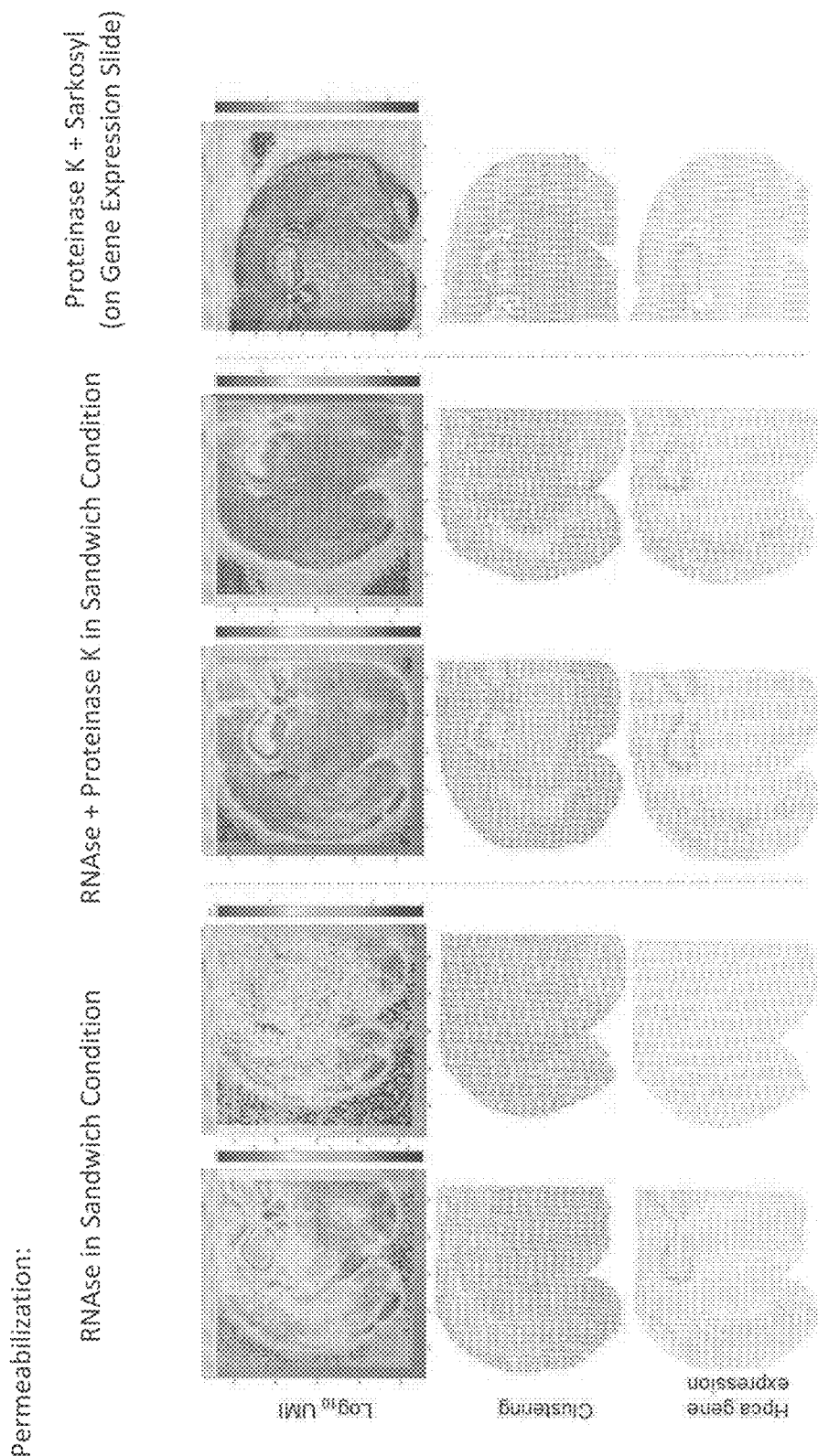
FIG. 13 shows exemplary images of spatially-resolved information of gene expression after analyzing the ligated probes in FFPE mouse brain tissue.

FIG. 13 shows results from the mouse brain 5000 probe experiment. As seen in FIG. 13, analyte detection and clustering was observed on a large scale (e.g., using 5000 probe pairs). Further, individual gene (e.g., Hpca) detection was achieved. Taken together, these data demonstrate the ability to image clusters of genes and even individual genes using these sandwich methods.

Table 3 and Table 4 below show results of the captured ligated probes on mouse kidney in a setting of using probes designed to hybridize to part of the mouse transcriptome (e.g., using partial (i.e., n=5000) total probe pairs).

TABLE 3

| Conditions | Valid Barcodes | Valid UMIs | Fraction targeted reads usable | Reads Mapped Confidently to Transcriptome | Fraction Reads in Spots Under Tissue | Fraction reads unmapped |
|---|---|---|---|---|---|---|
| RNAse only (30 mins) mouse kidney | 96.3% | 100.0% | 79.3% | 88.3% | 91.7% | 8.8% |
| RNAse + Proteinase K (30 mins) mouse kidney | 97.9% | 100.0% | 84.8% | 93.3% | 92.8% | 3.1% |
| RNAse + Proteinase K + Sarkosyl (30 mins) mouse kidney | 96.9% | 100.0% | 79.9% | 91.6% | 89.0% | 4.9% |
| Control mouse kidney | 96.4% | 100.0% | 65.3% | 85.9% | 78.3% | 9.1% |

TABLE 4

| Conditions | Median panel genes detected at 260 panel reads per spot | Median panel UMI counts at 250 reads per spot | Median panel genes directed at 1000 panel reads per spot | Median panel UMI counts at 1000 panel reads per spot |
|---|---|---|---|---|
| RNAse only (30 mins) mouse kidney | 99 | 167 | 166 | 335 |
| RNAse + Proteinase K (30 mins) mouse kidney | 127 | 208 | 283 | 642 |
| RNAse + Proteinase K + Sarkosyl (30 mins) mouse kidney | 79 | 121 | 129 | 226 |
| Control mouse kidney | 103 | 164 | 203 | 411 |

As shown in Table 3 and Table 4, the combination of RNAse+Proteinase K using sandwiching methods resulted in increased useable fraction targeted reads, increased reads in spots under tissues, and increased median panel genes and UMI counts.

Figure 14:
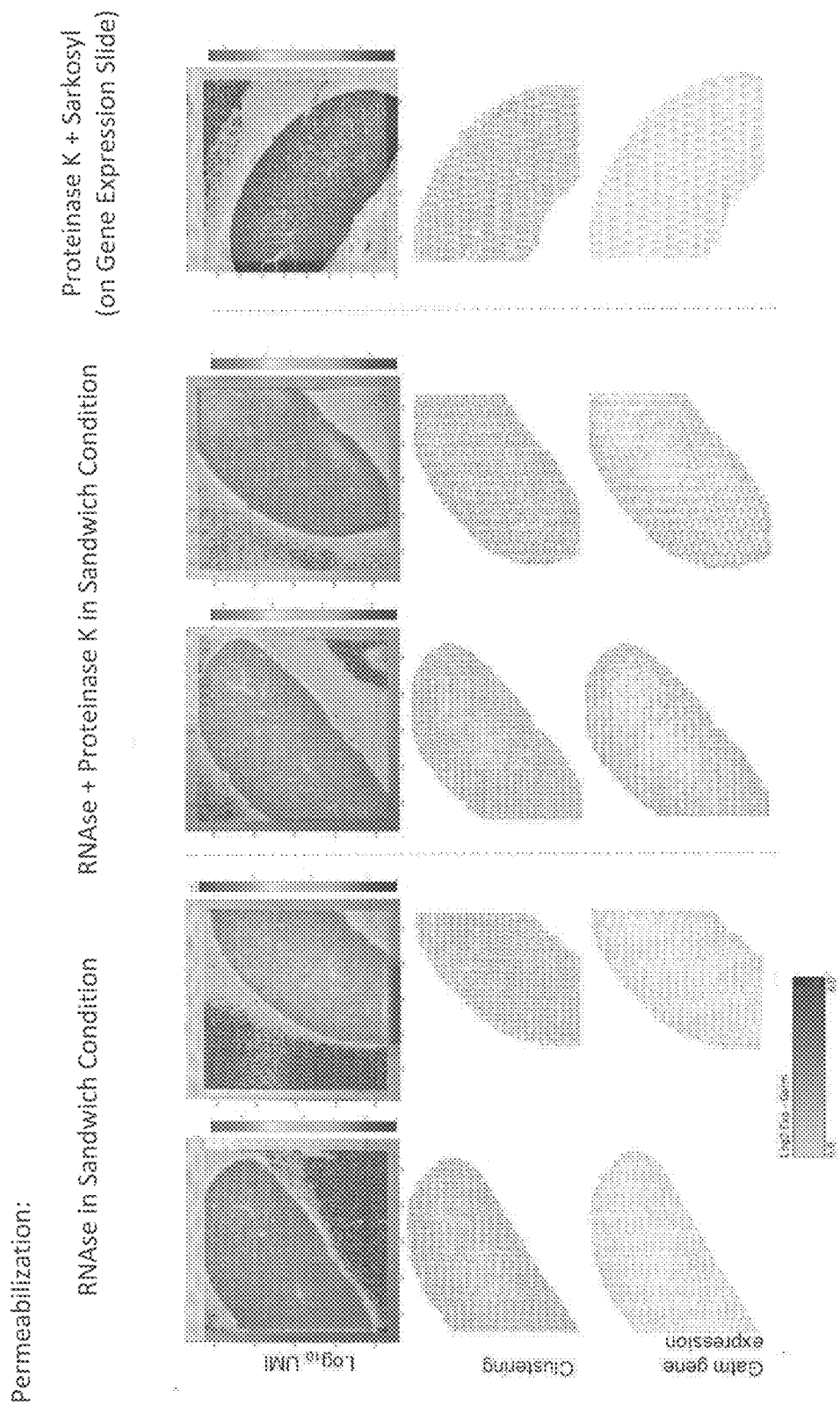
FIG. 14 shows exemplary images of spatially-resolved information of gene expression after analyzing the ligated probes in FFPE mouse kidney tissue.

FIG. 14 shows results from the mouse kidney 5000 probe experiment. As seen in FIG. 14, analyte detection and clustering was observed on a large scale (e.g., using 5000 probe pairs). Further, individual gene (e.g., Gatm) detection was achieved. Taken together, these data demonstrate the ability to image clusters of genes and even individual genes using these sandwich methods.

In addition, as shown in Table 5, other FFPE samples from human brain, human lung, mouse spleen, mouse thymus, and mouse testes were tested using either 3000 probe pairs for human samples or 5000 probe pairs for mouse samples. The samples were sandwiched, and probes were released using a combination of RNAse and Proteinase K.

TABLE 5

| Sample | Fraction Reads in Spots under Tissue | Median Panel Genes Detected at 1000 Panel Reads per Spot | Median Panel UMI Counts at 1000 Panel Reads per Spot |
|---|---|---|---|
| Human Brain (Control—no sandwich) | 97.1% | 247 | 315 |
| Human Brain—RNAse + Proteinase K (30 mins) | 75.6% | 322 | 564 |
| Human Lung (Control – no sandwich) | 42.6% | 569 | 1494 |
| Human Lung—RNAse + Proteinase K (30 mins) | 95.3% | 862 | 1254 |
| Mouse Spleen (Control – no sandwich) | 74.1% | 264 | 799 |
| Mouse Spleen—RNAse + Proteinase K (30 mins) | 90.9% | 317 | 919 |
| Mouse Thymus (Control—no sandwich) | 75.8% | 293 | 639 |
| Mouse Thymus—RNAse + Proteinase K (30 mins) | 76.1% | 359 | 918 |
| Mouse Testes (Control—no sandwich) | 93.0% | 385 | 921 |
| Mouse Testes—RNAse + Proteinase K (30 mins) | 98.6% | 352 | 941 | b. Methods of Capturing Connected Probes that Hybridize to Analytes in a Mouse Brain Samples Using Probe Pairs that Hybridize to Probe Pairs Designed to Cover the Entire Mouse Transcriptome.

The methods of Example 1a were repeated in a second set of mouse brain samples, except that probe pairs that cover the entire mouse transcriptome were used (21,000 probe pairs). Table 6 shows results of capture of connected probes using probe pairs designed to cover the entire mouse transcriptome.

Example 2—Methods for Spatial Analysis of RNA and Protein with Sandwich Process In a non-limiting example, methods for spatial analysis of RNA and protein were performed. In brief, mouse brain FFPE sections on standard slides (for sandwich conditions) or gene expression (GEx) slides (for non-sandwich control conditions) were decrosslinked according to the steps in Example ca. Probe hybridization using mouse-specific probe sets to the mouse partial transcriptome (n=5000 probe pairs)

TABLE 6

| Sample | Valid Barcodes | Valid UMIs | Fraction Targeted reads usable | Reads mapped confidently to transcriptome | Fraction Reads in Spots under Tissue | Fraction Reads Unmapped | Median Panel Genes detected at 10000 panel reads per spot | Median Panel UMI counts at 10000 panel reads per spot |
|---|---|---|---|---|---|---|---|---|
| Control mouse brain (RTL but no sandwich methods) | 97.2% | 100.0% | 57.9% | 67.5% | 88.2% | 2.6% | 2542 | 4746 |
| RNAse + Proteinase K (30 mins) mouse brain | 97.2% | 100.0% | 88.8% | 94.7% | 96.3% | 1.8% | 3484 | 7753 |

Figure 15:
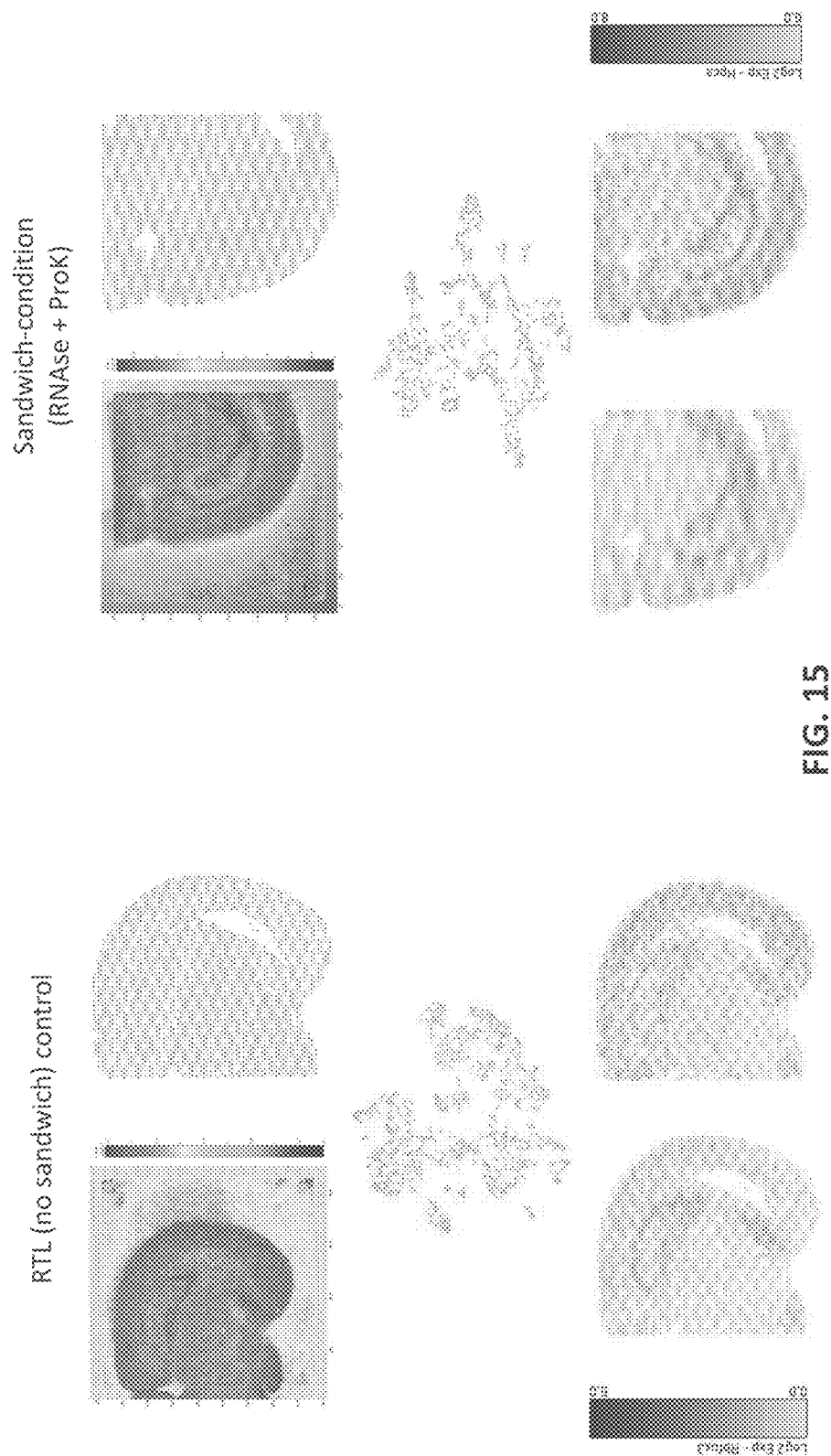
FIG. 15 shows exemplary images of spatially-resolved information of gene expression after analyzing the ligated probes in FFPE mouse brain tissue.

As shown in FIG. 15, analyte detection was observed in both sandwich and non-sandwich methods, demonstrating the ability to detect analytes in both settings. Further, individual gene (e.g., Rbfox3; Hpca) detection was achieved. Taken together, these data demonstrate the ability to image clusters of genes and even individual genes using these sandwich methods.

Table 7 shows results of capture of connected probes using probe pairs designed to cover human transcriptome (3000 probe panel) or mouse transcriptome (5000 probe panel) with different types of tissue samples.

was performed, followed by RTL probe ligation as described in Example 1. The sections were then incubated with totalseq B oligo-tagged antibodies for NeuN and Gfap, followed by washing. The antibodies were tagged with oligonucleotides that have a sequence complementary to a capture probe capture domain of a GEx slide and a barcode sequence that uniquely identifies the antibody. The connected probes and antibody oligonucleotide tags were released from the tissue under sandwich conditions as described herein or under non-sandwich conditions. For both conditions, the reagent medium included RNase and Proteinase K. For the

TABLE 7

Figure 16B:
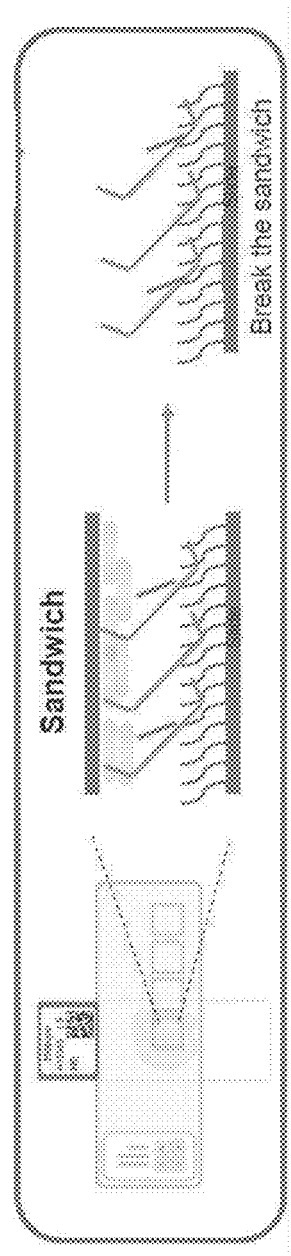
FIG. 16B shows an exemplary schematic illustrating the tissue sample sandwiched between a substrate and a spatially-barcoded capture probe array, wherein the ligated probes and capture agent barcode domains are transferred to the spatially-barcoded capture probe array.

| Tissue type | Sample | Fraction Reads in Spots Under Tissue | Median panel genes detected at 1000 panel reads per spot | Median panel UMI counts at 1000 panel reads per spot |
|---|---|---|---|---|
| Human brain | Control—no sandwich | 97.1% | 247 | 315 |
|  | RNase + Proteinase K | 75.6% | 322 | 564 |
| Human lung | Control—no sandwich | 42.6% | 569 | 1494 |
|  | RNase + Proteinase K | 95.3% | 862 | 1254 |
| Mouse spleen | Control—no sandwich | 74.1% | 264 | 799 |
|  | RNase + Proteinase K | 90.9% | 317 | 919 |
| Mouse thymus | Control—no sandwich | 75.8% | 293 | 639 |
|  | RNase + Proteinase K | 76.1% | 359 | 918 |
| Mouse testes | Control—no sandwich | 93.0% | 385 | 921 |
|  | RNase + Proteinase K | 98.6% | 352 | 941 | sandwich conditions, the tissue-mounted slides were aligned with a GEx slide and permeabilized in the sandwich configuration as described herein (see, e.g., FIG. 16B). For the non-sandwich condition, the tissue mounted on the GEx slide was permeabilized directly on the GEx array. Following permeabilization, the capture probes were extended, sequencing libraries were prepared and sequenced, and the results were analyzed computationally.

Table 8 shows mRNA analysis results. Table 9 shows antibody analysis results.

TABLE 8

| Sample | Valid Barcodes | Valid UMIs | Fraction Targeted reads usable | Reads mapped confidently to transcriptome | Fraction Reads in Spots under Tissue | Fraction Reads Unmapped | Median Panel Genes detected at 10000 panel reads per spot | Median Panel UMI counts at 10000 panel reads per spot |
|---|---|---|---|---|---|---|---|---|
| Control mouse brain (RTL but no sandwich methods) | 98.9% | 100.0% | 69.9 | 73.5% | 96.2% | 12.2% | 216 | 366 |
| RNAse + Proteinase K (30 mins) mouse brain | 99.0% | 100.0% | 91.3% | 97.1% | 95.0% | 2.2% | 391 | 814 |

TABLE 9

| Sample | Valid Barcodes | Valid UMIs | Fraction Targeted reads usable | Reads mapped confidently to transcriptome |
|---|---|---|---|---|
| Control mouse brain (RTL but no sandwich methods) | 88% | 61% | 12% | 70% |
| RNAse + Proteinase K (30 mins) mouse brain | 74% | 68% | 26% | 93% |

Figure 18A:
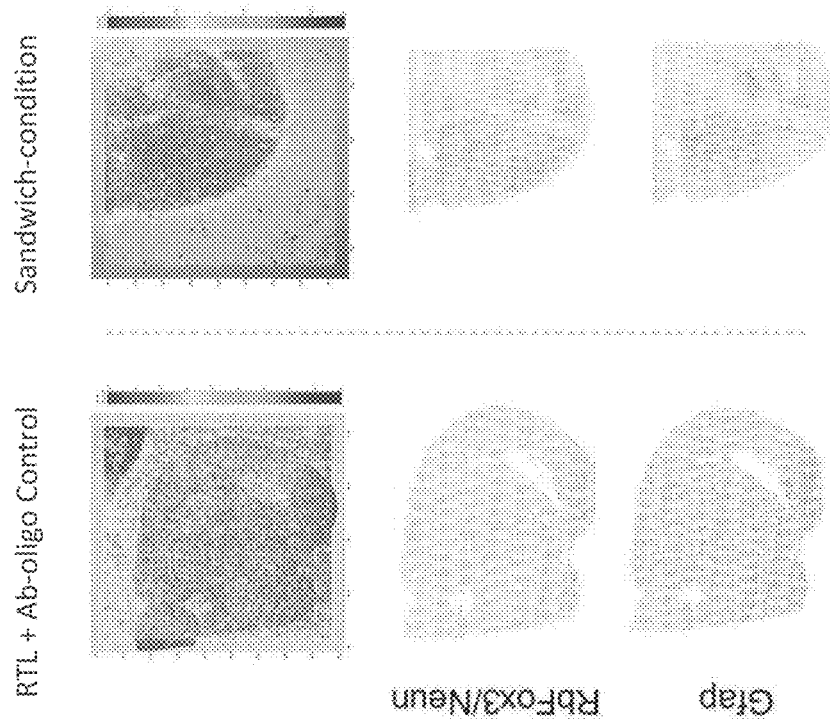
FIGS. 18A and 18B shows exemplary images of spatially-resolved information of gene expression after analyzing the ligated probes in FFPE mouse brain tissue.
Figure 18B:
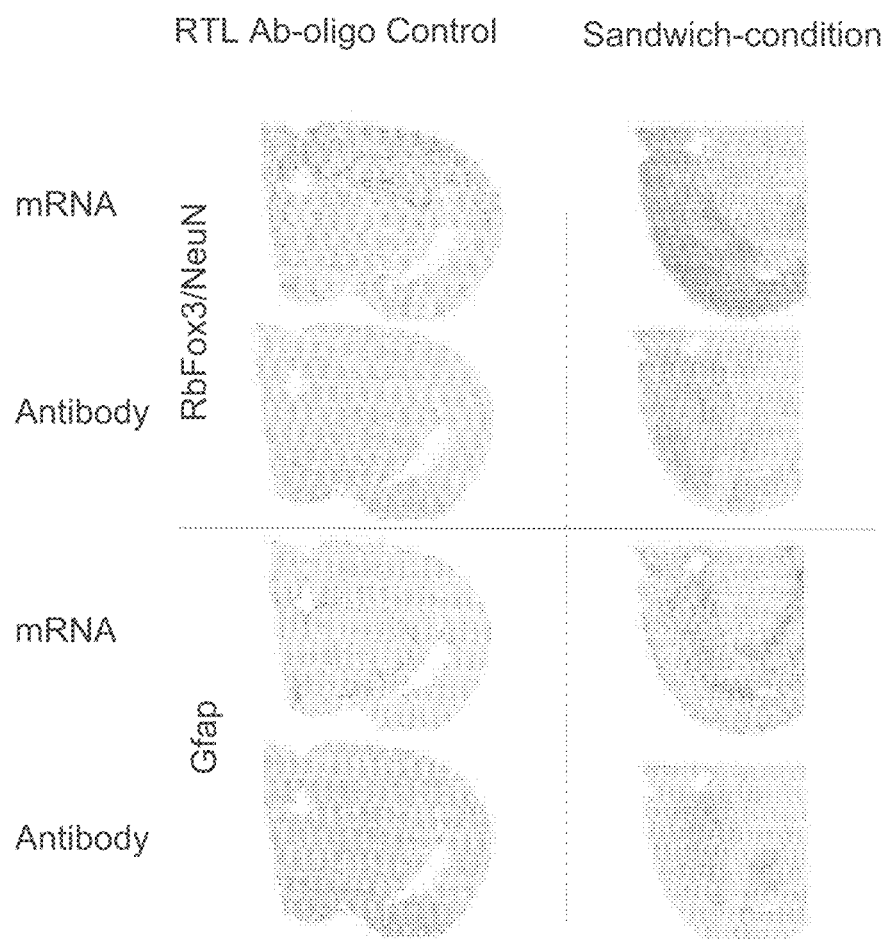

As shown in FIG. 18A-18B, mRNA and protein analyte detection was observed in both sandwich and non-sandwich methods, demonstrating the ability to detect analytes in both settings. Further, individual gene (e.g., RbFox3/NeuN; Gfap) detection was achieved. Taken together, these data demonstrate the ability to image clusters of protein or mRNA analytes and even individual protein or mRNA analytes using these sandwich methods.

Example 3—Methods for Spatial Transcriptomics Analysis Utilizing Sandwich Process In a non-limiting example, the sandwich process can be utilized for a downstream analytical step in spatial transcriptomics analysis workflows as described herein.

FIG. 19A shows an exemplary workflow of spatial analysis assays using fresh frozen tissue samples. For example, a tissue section is (a) fixed and stained (e.g., hematoxylin and eosin staining, fluorescent antibody staining); (b) imaged to evaluate the quality of the antibody staining; (c) destaining and unmounting the tissue section; (d) permeabilizing the tissue section with Proteinase K and sarkosyl prior to performing the sandwich process; and (e) performing a reverse transcription protocol and generating an analyte library.

FIG. 19B shows an exemplary workflow of spatial analysis assays using formalin-fixation and paraffin-embedded (FFPE) tissue samples. For example, a FFPE tissue section is (a) deparaffinized, wherein the paraffin-embedding material is removed; (b) fixed and stained (e.g., hematoxylin and eosin staining, fluorescent antibody staining); (b) imaged to evaluate the quality of the antibody staining; (c) destaining and unmounting the tissue section; (d) permeabilizing the tissue section with RNase, Proteinase K and sarkosyl prior to performing the sandwich process; and (e) performing a reverse transcription protocol and generating an analyte library.

Example 4—Methods for Spatial Transcriptomics Analysis Utilizing Serial Sandwich Process In a non-limiting example, the sandwich process can be repeated using serial biological sections with transfer to the same substrate comprising a plurality of capture probes.

To demonstrate the ability to capture analytes from multiple biological samples, connected probes were generated on separate slides, with each slide comprising a different biological sample. Briefly, in Biological Sample 1, a mouse sample was used. In Biological Sample 2, a human sample was used. In particular, mouse thymus or mouse testes biological samples were used as Biological Sample 1, and human lung or human breast cancer samples were used for Biological Sample 2. Probes were designed to hybridize to mouse-specific mRNA analytes or human-specific analytes. In some embodiments, partial transcriptome probe panels were used. In some embodiments, mouse transcriptome probe panels were used. In some embodiments, human transcriptome probe pairs were used.

Individual probe oligonucleotides (e.g., a first probe oligonucleotide, a second probe oligonucleotide) in a probe pair hybridized to adjacent sequences of an analyte (e.g., an RNA molecule) in each biological sample. The RTL probe oligonucleotides were then ligated together, thereby creating a connected probe. After ligation of the RTL probe oligonucleotides, RNase H was added to release the ligated product from the analyte, and proteinase K was added to the samples to permeabilize the biological samples.

During the permeabilization step, each sample (i.e., Biological Sample 1 and Biological Sample 2) was serially added to the second substrate (i.e., the substrate comprising capture probes that capture the connected probes. The poly (A) sequence on the connected probe hybridized to the poly(T) sequence of the capture probe domain. After hybridization of the connected probes from Biological Sample 1, Biological Sample 1 was removed from the capture probe-containing substrate. The capture-probe-containing substrate was washed briefly with 1×SSC, dried quickly, and this sandwich-transfer method was repeated for Biological Sample 2.

Figure 21A:
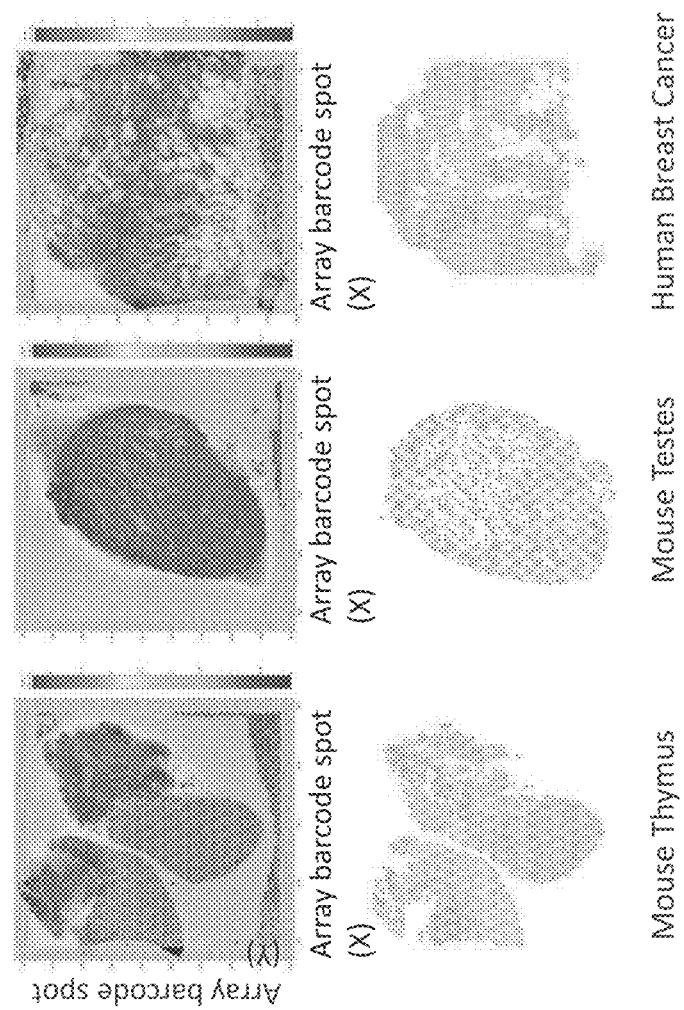
FIG. 21A shows heat maps and clustering images of mouse thymus, mouse testes, and human breast cancer samples using non-sandwiching techniques.
Figure 21B:
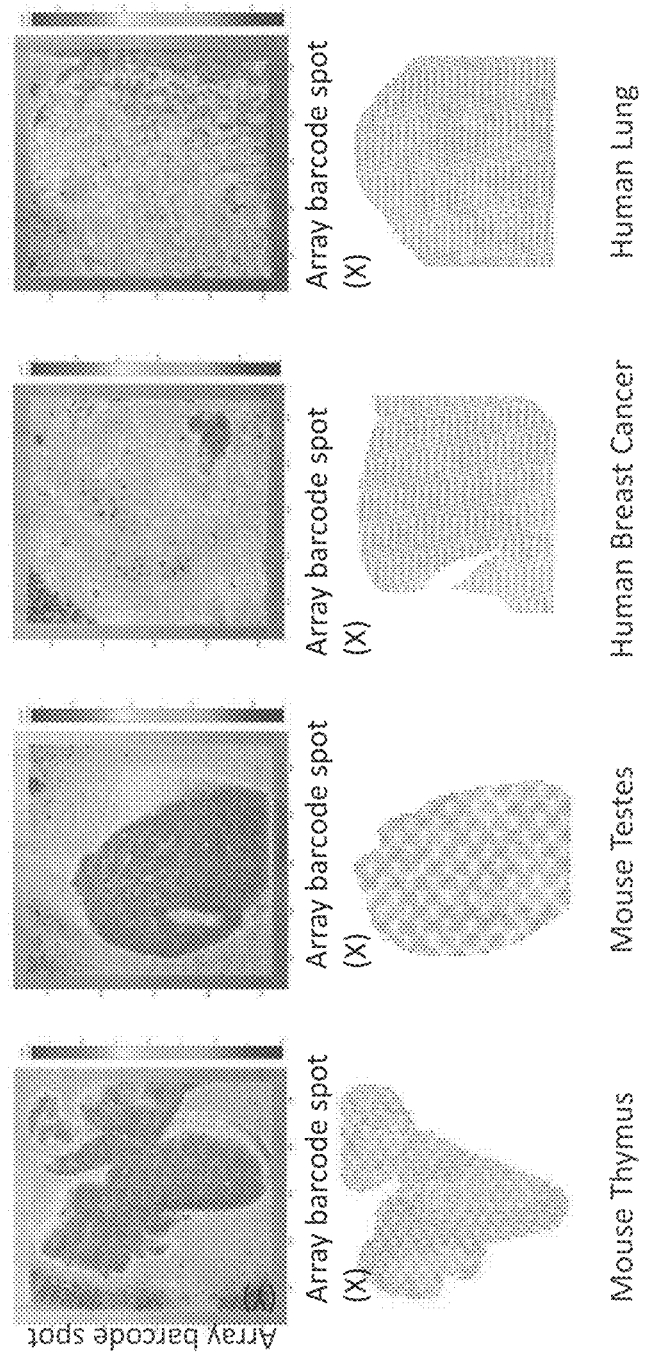
FIG. 21B shows heat maps and clustering images of mouse thymus, mouse testes, and human breast cancer samples using single-sample-sandwiching techniques.

As shown in FIG. 20, human RTL connected probes were detected, demonstrating that serial transfer of multiple probes can be achieved. As controls, biological samples (i.e., mouse thymus, mouse testes, and human breast cancer) in which no sandwiching methods were used (FIG. 21A), and biological samples in which a single sandwiching transfer was used (FIG. 21B). In each control, as shown in the heat maps and clustering images (FIGS. 21A-21B), connected probes were captured and detected on the array.

Figure 22A:
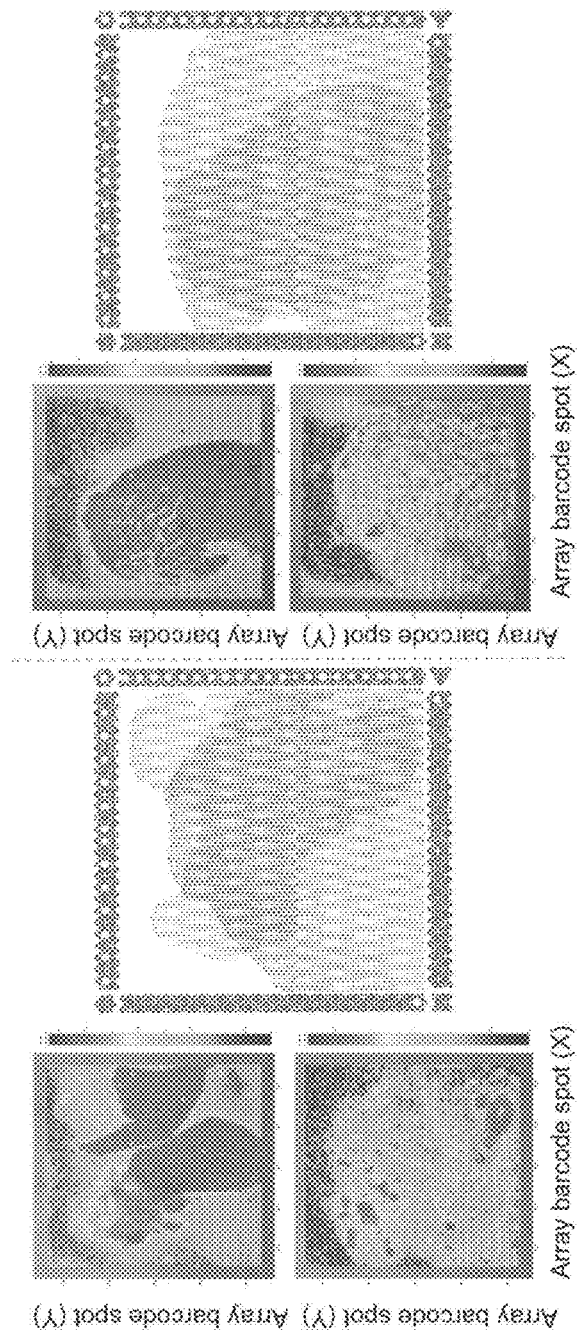
FIGS. 22A and 22B show heat maps and clustering images mouse and human samples using multiple-sample-sandwiching techniques.
Figure 22B:
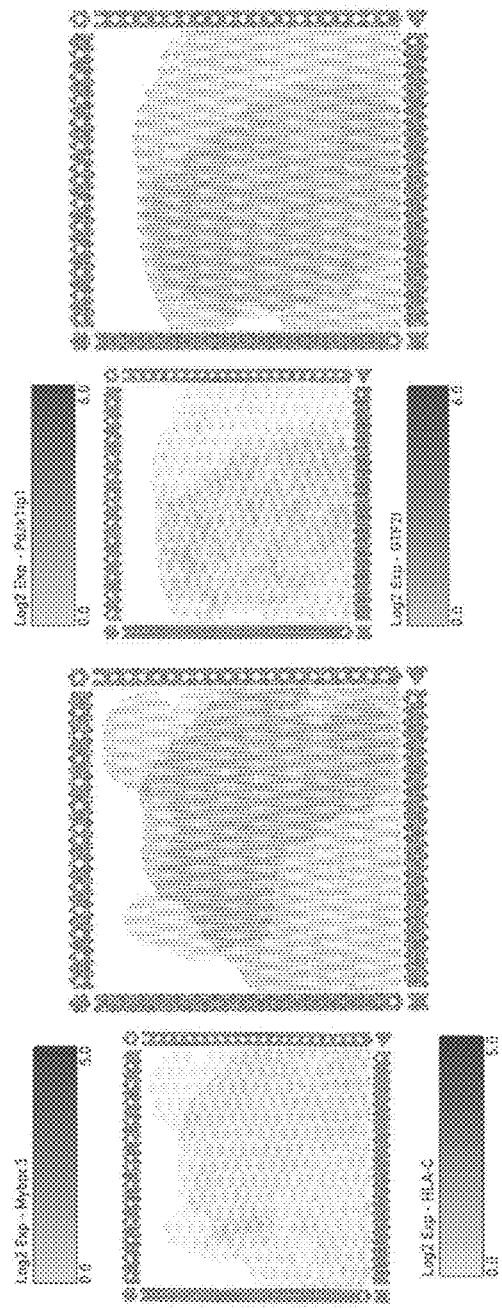

FIGS. 22A-22B show heat maps for each sample type, demonstrating the location and saturation of the sequenced reads in the second substrate. FIGS. 22A-22B also show the clustering and spatiality of reads under the tissue in an overlay utilizing the loupe file fiducials. It is assumed that regions of the tissue that have similar gene expression will be clustered together and represented by the same color in these images. The overlay of the clustered reads suggest that reads from both mouse and human tissues were captured. The pattern of the reads under tissue seen in the heat map are represented for each tissue type in the overlaid clustered reads.

The results demonstrate the ability to serially capture analytes from different biological samples on the same array. The results also demonstrate the ability to demultiplex the samples computationally.

Example 5—Efficient Analyte Capture from Slide-Mounted Fresh Frozen Mouse Brain Sections onto Spatial Array Slides In a non-limiting example, analyte capture onto spatially barcoded arrays and subsequent sequencing was demonstrated under sandwich and non-sandwich conditions. For the test (sandwiching) condition, archived tissue-mounted standard glass slides containing hematoxylin/eosin stained fresh frozen mouse brain sections were used. For control (non-sandwich) condition, gene expression (GEx) array slides with hematoxylin/eosin stained fresh frozen mouse brain sections mounted directly onto the array area were used. Under both conditions, tissue sections were subjected to a hematoxylin destaining step. Slides processed according to the "sandwiching" condition were briefly dried at 37° C., then mounted in an instrument along with a GEx slide and a permeabilization buffer comprising sarkosyl and proteinase K. Upon sandwich closure in the instrument, the tissue sections were permeabilized for 1 minute. For the tissue-mounted GEx slides processed according to the non-sandwich condition, sections were permeabilized for 5 minutes using the same permeabilization buffer without sandwiching. For both conditions, following permeabilization, captured polyA-containing mRNA transcripts on the GEx slides were reverse transcribed into cDNA, followed by standard sequencing library preparation and sequencing.

Results depicting median genes per spot and median UMI counts per spot are shown in FIG. 24.

Figure 25:
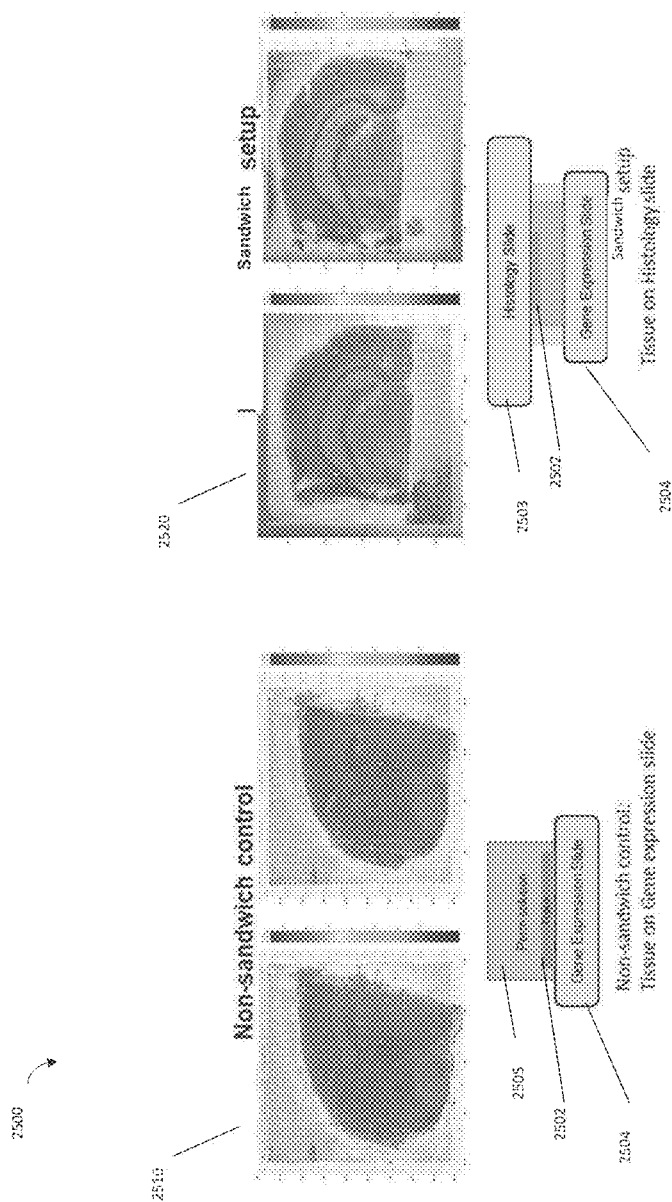
FIG. 25 shows an exemplary comparison between a non-sandwich control and a sandwich configuration permeabilization condition.

Visual heat map results showing Log 10 UMIs are shown in FIG. 25. Spatial patterns of the Log 10 UMI counts were similar across the sandwich and non-sandwich conditions.

Figure 26:
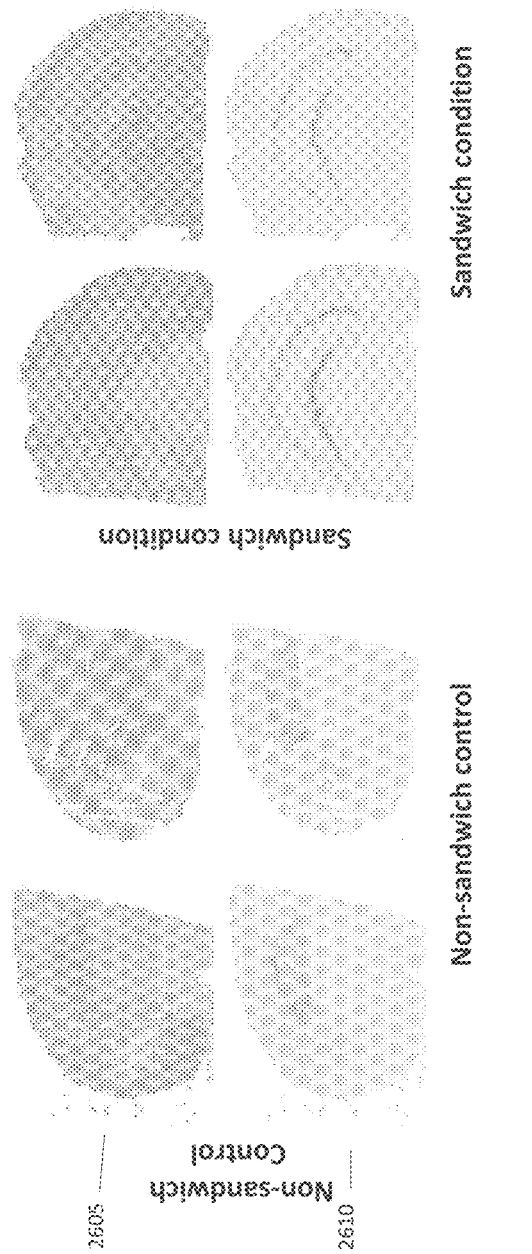
FIG. 26 shows exemplary images of spatial clustering analysis and analysis of hippocampal transcript Hpca, comparing non-sandwich control and sandwich configuration permeabilization conditions.

Spatial clustering analysis (top row 2605) and analysis of hippocampal transcript Hpca (bottom row 2610) are depicted in FIG. 26. Spatial patterns were comparable across the sandwich and non-sandwich conditions.

Example 6—Efficient Analyte Capture from Slide-Mounted FFPE Human Brain and Human Breast Sections onto Spatial Array Slides In a non-limiting example, human brain and human breast FFPE sections on standard slides (for sandwich conditions) or gene expression (GEx) slides (for non-sandwich control conditions) were deparaffinized, H&E stained, and imaged. Next, the tissue samples were hematoxylin-destained with three HCl solution washes and then decrosslinked according to the steps in Example 1a.

Probe hybridization was performed, followed by RTL probe ligation as described in Example 1. The sections were then incubated with totalseq B oligo-tagged antibodies for NeuN and Gfap, followed by washing. The antibodies were tagged with oligonucleotides that have a sequence complementary to a capture probe capture domain of a GEx slide and a barcode sequence that uniquely identifies the antibody. The connected probes and antibody oligonucleotide tags were released from the tissue under sandwich conditions as described herein or under non-sandwich conditions. For both conditions, the reagent medium included RNase and Proteinase K. For the sandwich conditions, the tissue-mounted slides were aligned with a GEx slide and permeabilized in the sandwich configuration as described herein (see, e.g., FIG. 16B). For the non-sandwich condition, the tissue mounted on the GEx slide was permeabilized directly on the GEx array. Following permeabilization, the capture probes were extended, sequencing libraries were prepared and sequenced, and the results were analyzed computationally.

Visual heat map results showing Log 10 UMIs for human brain and human breast tissues are shown in FIGS. 27A and 27B, respectively. Spatial patterns of the Log 10 UMI counts were similar across the sandwich and non-sandwich conditions. Spatial clustering analysis of the human brain and human breast tissues are depicted in FIGS. 27A and 27B, respectively. These data demonstrate that spatial clustering was comparable across the sandwich and non-sandwich conditions.

Example 7—Efficient Multiplexed Analyte Capture from Slide-Mounted Mouse Spleen, Brain, Head, and Torso Sections onto Spatial Array Slides In a non-limiting example, FFPE mouse spleen samples, FFPE mouse brain samples, FFPE mouse embryo torso samples, and FFPE mouse embryo head sections samples were placed onto standard slides (for sandwich conditions) or spatial expression (GEx) slides (as non-sandwich conditions). GEx slides included an array of spatially barcoded capture probes. Briefly, tissues were sectioned and were mounted on slides and dried overnight in a desiccator. The following day, the tissues were heated to 60° C., followed by deparaffinization and rehydration. H&E staining was performed and tissues were imaged. Tissues were destained using HCl and decrosslinked for 1 hour in citrate buffer (pH 6.0) at 95° C. After decrosslinking, tissues were incubated overnight with whole mouse transcriptome RTL (templated ligation) probe sets at 50° C. The following day, tissues were washed to remove un-hybridized probes, then treated with ligase to ligate together the RTL probes. After another wash step, the tissues were blocked with antibody blocking buffer. Tissues were incubated overnight with a library of conjugated antibodies (e.g., a library comprising a plurality of analyte capture agents, each comprising an antigen-specific antibody conjugated to an oligonucleotide). The following day, tissues were subjected to sandwiching or non-sandwich conditions as follows.

Tissues placed on standard slides for the sandwiching conditions were washed with PBS-T, subjected to an eosin retain, and washed with SSC. These tissues were subjected to sandwiching conditions described herein. Briefly, the tissue slides were mounted in an instrument along with a GEx slide and a reagent solution including RNase and proteinase K in buffer. Upon sandwich closure in the instrument, the tissue sections were permeabilized for 30 minutes, allowing the ligation products and oligonucleotides from analyte capture agents to migrate to the GEx slide for capture by the capture probes. Following permeabilization and capture, the GEx slides were removed from the instrument.

Tissues placed on the GEx slides for non-sandwiching conditions were washed with PBST, and washed with SSC. The tissues were subjected to a 30 minute probe release step with RNase, followed by a 1 hour permeabilization step with a permeabilization buffer including Proteinase K and detergent. Accordingly, the ligation products and analyte capture agents were captured by the capture probes of the GEx slide.

Regardless of condition, GEx slides were washed twice with 2xSSC and subjected to probe extension, denaturation, and pre-amplification followed by amplification and sequencing of the templated ligation and analyte capture agent libraries.

After sequencing, the quality, sensitivity, and detection under each conditions (sandwiching and non-sandwiching conditions) were evaluated. As shown in Table 10, the quality, sensitivity, and detection of globally-detected transcripts (i.e., mRNA) and proteins were comparable across the sandwich and non-sandwich conditions.

TABLE 10

| | Metric | Sandwiching Conditions | Non-Sandwiching Conditions |
|---|---|---|---|
| Templated Ligation Quality | Valid barcodes | 99.00% | 98.90% |
| | Fraction reads on target | 85.60% | 82.10% |
| | Fraction reads usable | 79.80% | 78.70% |
| | Fraction reads in spots | 81.60% | 81.00% |
| | Fraction reads unmapped | 0.90% | 1.00% |
| Templated Ligation Sensitivity | Median genes (20K prps) | 4856 | 4705 |
| | Median UMIs (20K prps) | 16966 | 15156 |
| Protein Detection using Analyte Capture Agents | Fraction reads usable | 75.20% | 67.10% |
| | Fraction reads in spot | 78.70% | 70.10% |
| | Fraction unknown | 3.70% | 3.60% |
| | Median UMIs per spot (5K reads usable per spot) | 4632 | 4114 |
| | Correlation of selected Templated Ligation/Analyte Capture Agent | 0.77 | 0.76 |

Images were generated to evaluate overlap of gene expression and gene product (e.g., protein) profiles in mouse spleen tissue and mouse brain tissue for individual biomarkers. For instance, CD45, which is expressed in both spleen and brain, was evaluated. As shown in FIG. 28A (sandwiching conditions) and FIG. 28C (non-sandwiching conditions), protein tyrosine phosphatase receptor type C (Ptprc; e.g., Ensembl: ENSMUSG00000026395) mRNA expression was detected in a spleen tissue sample. Further, gene product (e.g., protein) CD45R was also detected both in sandwiching conditions (FIG. 28B) and in non-sandwiching conditions (FIG. 28D). CD45R is the protein name of Ptprc, and it was determined whether there was overlap of mRNA expression of Ptprc and protein expression of CD45R. As shown in FIGS. 28A-28B and FIGS. 28C-28D, both sandwiching (77% correlation) and non-sandwiching conditions (76% correlation), respectively, demonstrated overlap of transcript and protein, indicating that transcript (i.e., mRNA) and protein detection (1) was identified in similar areas of the tissues, and the (2) was comparable across the sandwich and non-sandwich conditions in mouse spleen samples.

Mouse brain samples were also evaluated. In particular, the quality, sensitivity, and detection under each conditions (sandwiching and non-sandwiching conditions) were evaluated globally in mouse brain samples. As shown in Table 11, the quality, sensitivity, and detection of globally-detected transcripts (i.e., mRNA) and proteins were comparable across the sandwich and non-sandwich conditions in mouse brain samples.

TABLE 11

| | Metric | Sandwiching Conditions | Non-Sandwiching Conditions |
|---|---|---|---|
| Templated Ligation Quality | Valid barcodes | 99.00% | 98.90% |
| | Fraction reads on target | 92.00% | 87.30% |
| | Fraction reads usable | 88.80% | 72.30% |
| | Fraction reads in spots | 91.80% | 79.10% |
| | Fraction reads unmapped | 1.10% | 1.90% |

TABLE 11-continued

| | Metric | Sandwiching Conditions | Non-Sandwiching Conditions |
|---|---|---|---|
| Templated Ligation Sensitivity | Median genes (10K prps) | 4405 | 3185 |
| | Median UMIs (10K prps) | 9386 | 5553 |
| Protein Detection using Analyte Capture Agents | Fraction reads usable | 80.70% | 62.30% |
| | Fraction reads in spot | 84.40% | 65.10% |
| | Fraction unknown | 3.70% | 3.70% |
| | Median UMIs per spot (5K reads usable per spot) | 3232 | 3221 |
| | Correlation of selected Templated Ligation/Analyte Capture Agent | 0.63 | 0.63 |

Similar to the mouse spleen sample images described above, individual gene expression and protein products were evaluated in mouse brain samples. As shown in FIG. 29A (sandwiching conditions) and FIG. 29C (non-sandwiching conditions), tyrosine hydroxylase (Th; e.g., Ensembl: ENSMUSG00000000214) mRNA expression was detected in brain. Further, the gene product (e.g., protein) TH was also detected in sandwiching conditions (FIG. 29B) and non-sandwiching conditions (FIG. 29D). Since TH is the protein made by Th, it was determined whether there was overlap of mRNA expression of Th and protein expression of TH. As shown in FIGS. 29A-29B and FIGS. 29C-29D, both sandwiching (63% correlation) and non-sandwiching conditions (63% correlation), respectively, saw overlap of transcript and protein, demonstrating that transcript (i.e., mRNA) and protein detection was comparable across the sandwich and non-sandwich conditions in mouse brain samples.

Additional experiments using the same methods (i.e., testing sandwiching conditions versus non-sandwiching control conditions while detecting both RNA and protein) were performed on embryo torso and head sections. In addition to conditions in which both RNA and protein were detected, a third condition was included as a control. This third condition (Conditions 3 in Tables 12 and 13) detected the presence and abundance of only RNA. In each condition, RNA was detected using templated ligation as previously described herein. For Conditions 1 and 2 as shown in Tables 12 and 13 below, protein was also detected using analyte capture agent methods described herein. The quality, sensitivity, and detection under each condition (sandwiching versus non-sandwiching conditions) were evaluated in mouse embryo torso and head/upper torso samples. As shown in Tables 12 and 13, the quality, sensitivity, and detection of globally-detected transcripts (i.e., mRNA) and proteins were comparable across the sandwich and non-sandwich conditions in mouse embryo torso and head samples. Further, the quality, sensitivity, and detection of globally-detected transcripts (i.e., mRNA) was roughly the same between Conditions 1 and 3, demonstrating that both protein capture and sandwiching methods did not interfere with RNA capture using templated ligation methods.

TABLE 12

Mouse Embryo Torso Sample Data

| | Metric | Condition 1: Sandwiching Conditions Detecting both RNA and Protein | Condition 2: Non-Sandwiching Conditions Detecting both RNA and Protein | Condition 3: Non-Sandwiching Conditions Detecting RNA |
|---|---|---|---|---|
| Templated Ligation Quality | Valid barcodes | 98.9% | 99.0% | 98.5% |
| | Fraction reads on target | 88.5% | 88.5% | 87.9% |
| | Fraction reads usable | 81.5% | 77.7% | 84.8% |
| | Fraction reads in spots | 84.0% | 79.9% | 88.4% |
| | Fraction reads unmapped | 1.0% | 1.0% | 1.4% |
| Templated Ligation Sensitivity | Median genes (10K prps) | 4144 | 4356 | 3562 |
| | Median UMIs (10K prps) | 8767 | 8176 | 6121 |
| Protein Detection using Analyte Capture Agents | Fraction reads usable | 77.3% | 72.6% | — |
| | Fraction reads in spot | 80.8% | 75.9% | — |
| | Fraction unknown | 3.7% | 3.7% | — |
| | Median UMIs per spot (5K reads usable per spot) | 3358 | 3264 | — |
| | Correlation of selected Templated Ligation/Analyte Capture Agent | 0.90 | 0.80 | — |

TABLE 13

Mouse Embryo Head/Upper Torso Sample Data

| | Metric | Condition 1: Sandwiching Conditions Detecting both RNA and Protein | Condition 2: Non-Sandwiching Conditions Detecting both RNA and Protein | Condition 3: Non-Sandwiching Conditions Detecting RNA |
|---|---|---|---|---|
| Templated Ligation Quality | Valid barcodes | 99.0% | 99.0% | 98.5% |
| | Fraction reads on target | 89.1% | 89.4% | 89.0% |
| | Fraction reads usable | 86.7% | 82.9% | 82.2% |

TABLE 13-continued

Mouse Embryo Head/Upper Torso Sample Data

|  | Metric | Condition 1: Sandwiching Conditions Detecting both RNA and Protein | Condition 2: Non-Sandwiching Conditions Detecting both RNA and Protein | Condition 3: Non-Sandwiching Conditions Detecting RNA |
|---|---|---|---|---|
|  | Fraction reads in spots | 89.5% | 85.2% | 85.2% |
|  | Fraction reads unmapped | 1.0% | 1.0% | 1.5% |
| Templated | Median genes (10K prps) | 4400 | 4708 | 3562 |
| Ligation | Median UMIs (10K prps) | 9077 | 8431 | 6571 |
| Sensitivity |  |  |  |  |
| Protein | Fraction reads usable | 84.3% | 77.9% | — |
| Detection | Fraction reads in spot | 88.2% | 81.5% | — |
| using Analyte | Fraction unknown | 3.7% | 3.8% | — |
| Capture | Median UMIs per spot (5K | 3358 | 3349 | — |
| Agents | reads usable per spot) |  |  |  |
|  | Correlation of selected Templated Ligation/Analyte Capture Agent | 0.72 | 0.59 | — |

Figure 30A:
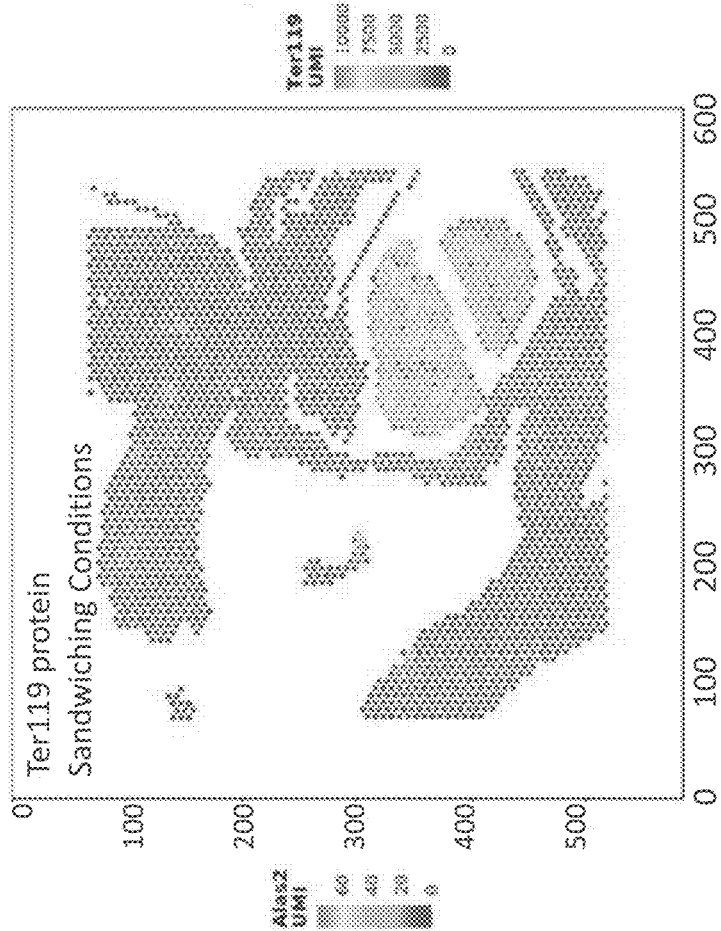
FIG. 30A shows an exemplary image of spatially-resolved information of gene expression of Ter119 RNA using ligated probes in FFPE mouse embryo torso tissue under sandwich configuration conditions.
Figure 30B:
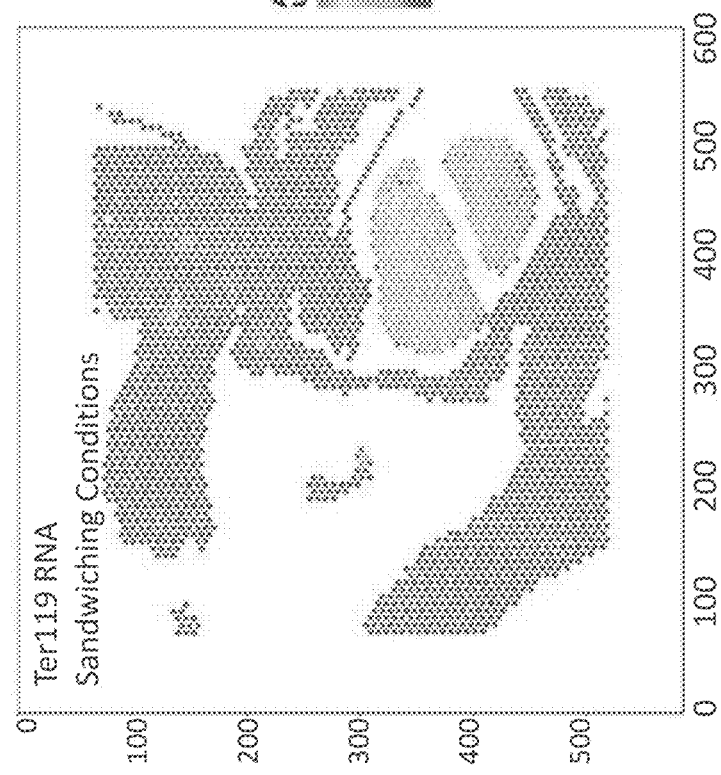
FIG. 30B shows an exemplary image of spatially-resolved information of protein expression of Ter119 using analyte capture agents in FFPE mouse embryo torso tissue under sandwich configuration conditions.
Figure 31A:
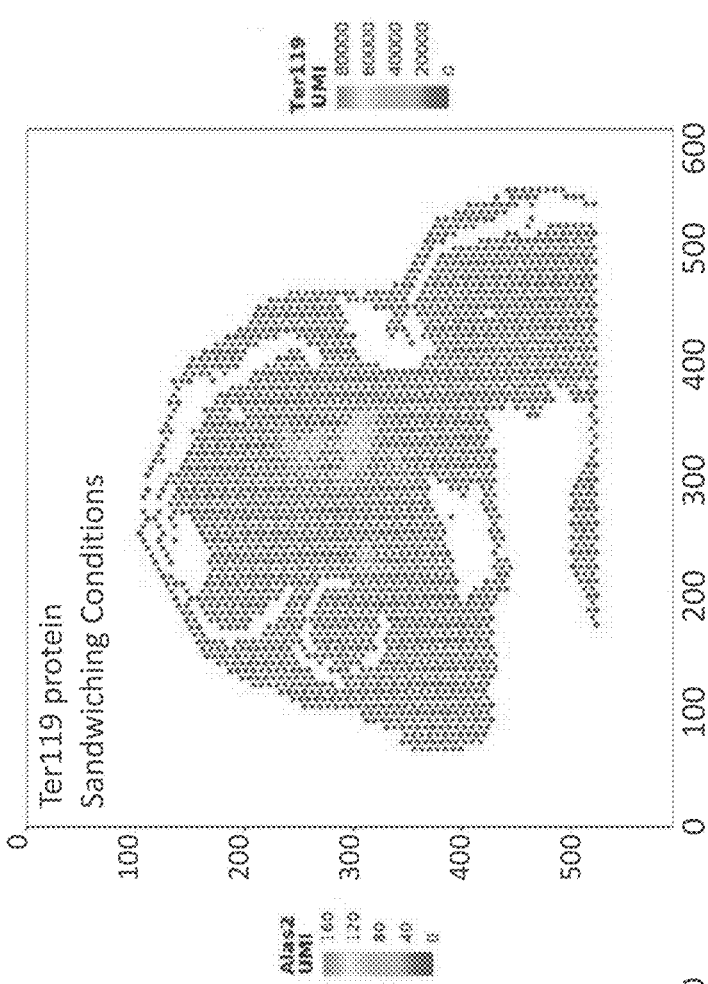
FIG. 31A shows an exemplary image of spatially-resolved information of gene expression of Ter119 RNA using ligated probes in FFPE mouse embryo head and upper torso tissue under sandwich configuration conditions.
Figure 31B:
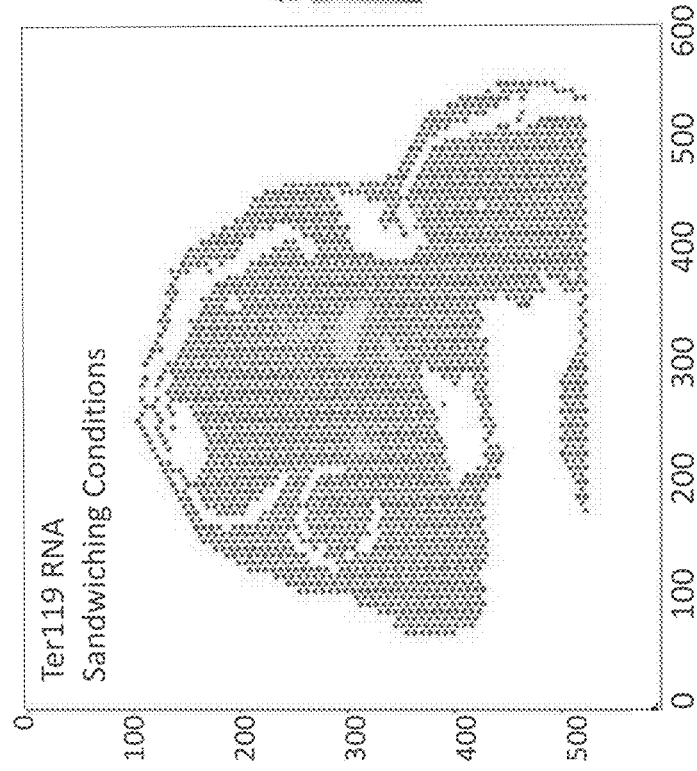
FIG. 31B shows an exemplary image of spatially-resolved information of protein expression of Ter119 using analyte capture agents in FFPE mouse embryo head and upper torso tissue under sandwich configuration conditions.

In addition to performing global expression analysis on each group, individual targets were analyzed for the location and abundance of transcript (i.e., mRNA) and protein of a single target in the mouse embryo torso and head/upper torso samples. FIGS. 30A-30B show mRNA (FIG. 30A) and protein (FIG. 30B) detection of lymphocyte antigen 76 (Ter119) (e.g., NCBI Gene ID: 104231), of mouse embryo torso samples in Condition 1 (i.e., in sandwiching conditions). FIGS. 30C-30D show mRNA (FIG. 30C) and protein (FIG. 30D) detection of Ter119 of mouse embryo torso samples in Condition 2 (i.e., in non-sandwiching conditions). FIGS. 31A-31B show mRNA (FIG. 31A) and protein (FIG. 31B) detection of Ter119 of mouse embryo head samples in Condition 1 (i.e., in sandwiching conditions). FIGS. 31C-31D show mRNA (FIG. 31C) and protein (FIG. 31D) detection of Ter119 of mouse embryo head/upper torso samples in Condition 2 (i.e., in non-sandwiching conditions). As shown in FIGS. 30A-31D, Ter119 mRNA and protein was readily detected with considerable overlap of mRNA and protein detection in both sandwiching conditions and non-sandwiching conditions, demonstrating the adaptability and reproducibility of the methods regardless of condition.

Additional single biomarkers were analyzed in the mouse embryo torso and head samples. As shown in FIGS. 32A-32I, metallophosphoesterase domain containing 1 (Mpped1; e.g., Ensembl: ENSMUSG00000041708) mRNA and protein was analyzed. Mpped1 was readily detected in the brain region of mouse embryo head samples. FIG. 32A shows detection of Mpped1 RNA in a mouse embryo head sample using sandwiching conditions (Condition 1 of Tables 12 and 13). FIG. 32B shows detection of Mpped1 protein in a mouse embryo head sample using sandwiching conditions (Condition 1 of Tables 12 and 13). However, Mpped1 mRNA was not readily detected in a mouse embryo torso sample. Consistent with these observations, Mpped1 has metallophosphoesterase activity, which could have a role in brain development. Consistent with the sandwiching conditions data, Mpped1 RNA and protein was detected in non-sandwiching conditions in the head (FIG. 32D (mRNA) and FIG. 32E (protein)) but not in the torso (FIG. 32F (mRNA) and FIG. 32G (protein)). Similarly, in non-sandwiching conditions in which only RNA was detected, Mpped1 RNA was detected in the head (FIG. 32H) but not in the torso (FIG. 32I). As such, regardless of conditions, both gene and protein expression, down to the single biomarker level, can be detected concurrently in the same sample.

Four additional biomarkers-troponin C1, slow skeletal and cardiac type (Tnnc1, e.g., Ensembl: ENSMUSG00000091898); fibroblast growth factor 15 (Fgf15, e.g., Ensembl: ENSMUSG00000031073); epiphycan (Epyc, e.g., Ensembl: ENSMUSG00000019936); and serine (or cysteine) peptidase inhibitor, clade A, member 1E (Serpina1e, e.g., Ensembl: ENSMUSG00000072849)—were examined in head/upper torso and torso mouse embryo samples under Conditions 1, 2, and 3 from Tables 12 and 13. See FIGS. 33A-36I. Tnnc1 is involved in muscle contraction regulation and its expression was readily detected in all samples under each Condition. See FIGS. 33A-33I. Fgf15 functions in retinal neurogenesis and as a cell fate determination factor. Indeed, its expression was found in the eye of the embryo in each head sample, but was not detected in the torso. See FIGS. 34A-34I. Epyc functions in bone formation and in cartilage structure and was detected in each sample (head and torso). See FIGS. 35A-35I. Finally, Serpina1e is active in the liver as it functions in alpha-1 antitrypsin protein production. As shown in FIGS. 36A-36I, Serpina1e was detected in the torso of mouse embryos but was not detected in the head/upper torso samples. Consistent among each of these biomarker images was that sandwiching methods readily detected individual mRNA or protein biomarkers compared to non-sandwiching methods. As such, using sandwiching or non-sandwiching conditions, both gene and protein expression, down to the single biomarker level, can be detected concurrently across multiple tissue types using the methods described herein.

What is claimed is:

1. A method for processing a nucleic acid analyte in a biological sample mounted on a first substrate, the method comprising:
   (a) hybridizing a first probe and a second probe to the nucleic acid analyte, wherein the first probe and the second probe each comprise a sequence that is substantially complementary to sequences of the nucleic acid analyte, and wherein the second probe comprises a capture probe binding domain;
   (b) coupling the first probe and the second probe, thereby generating a connected probe;
   (c) aligning the first substrate with a second substrate comprising an array, such that at least a portion of the biological sample is aligned with at least a portion of the array, wherein the array comprises a plurality of capture probes, wherein a capture probe of the plurality of capture probes comprises: (i) a spatial barcode and (ii) a capture domain;

(d) releasing the connected probe from the nucleic acid analyte when at least a portion of the biological sample is aligned with at least a portion of the array; and (e) hybridizing the connected probe to the capture domain of the capture probe on the array.

2. The method of claim 1, wherein the first probe and the second probe hybridize to adjacent sequences.

3. The method of claim 1, wherein the first probe and the second probe hybridize to sequences that are at least 1, 2, 3, 4, 5, 6, 7, 8, 9, 10, or more nucleotides away from one another.

4. The method of claim 3, further comprising (i) generating an extended first probe, wherein the extended first probe comprises a sequence complementary to a sequence between the sequence hybridized to the first probe and the sequence hybridized to the second probe; or (ii) an extended second probe using a polymerase, wherein the extended second probe comprises a sequence complementary to a sequence between the sequence hybridized to the first probe and the sequence hybridized to the second probe.

5. The method of claim 1, wherein the coupling the first probe and the second probe comprises ligating the first probe and the second probe.

6. The method of claim 4, wherein the coupling the first probe and the second probe comprises ligating:
the first probe and the extended second probe; or
the extended first probe and the second probe.

7. The method of claim 5, wherein the ligating is performed via a ligase.

8. The method of claim 7, wherein the ligase is selected from a *Chlorella* virus DNA ligase, a single-stranded DNA ligase, or a T4 DNA ligase.

9. The method of claim 1, wherein the aligning comprises:
mounting the first substrate on a first member of a support device, the first member configured to retain the first substrate;
mounting the second substrate on a second member of the support device;
applying a reagent medium to the first substrate and/or the second substrate; and
operating an alignment mechanism of the support device to move the first member and/or the second member such that at least a portion of the biological sample is aligned with at least a portion of the array, and such that the portion of the biological sample and the portion of the array contact the reagent medium.

10. The method of claim 9, wherein the alignment mechanism is coupled to the first member, the second member, or both the first member and the second member.

11. The method of claim 9, wherein the alignment mechanism comprises a linear actuator, optionally wherein:
the linear actuator is configured to move the second member along an axis orthogonal to the plane or the first member and/or the second member, and/or
the linear actuator is configured to move the first member along an axis orthogonal to the plane of the first member and/or the second member, and/or
the linear actuator is configured to move the first member, the second member, or both the first member and the second member at a velocity of at least 0.1 mm/sec, and/or the linear actuator is configured to move the first member, the second member, or both the first member and the second member with an amount of force of at least 0.1 lbs.

12. The method of claim 9, wherein at least one of the first substrate and the second substrate further comprise a spacer disposed on the first substrate or the second substrate, wherein when at least the portion of the biological sample is aligned with at least a portion of the array such that the portion of the biological sample and the portion of the array contact the reagent medium, the spacer is disposed between the first substrate and the second substrate and is configured to maintain the reagent medium within a chamber formed by the first substrate, the second substrate, and the spacer, and to maintain a separation distance between the first substrate and the second substrate, wherein the spacer is positioned to surround an area on the first substrate on which the biological sample is disposed and/or the array disposed on the second substrate, wherein the area of the first substrate, the spacer, and the second substrate at least partially encloses a volume comprising the biological sample.

13. The method of claim 1, wherein the releasing step (d) comprises contacting the biological sample with a reagent medium comprising a permeabilization agent and an agent for releasing the connected probe, thereby permeabilizing the biological sample and releasing the connected probe from the nucleic acid analyte.

14. The method of claim 13, wherein the agent for releasing the connected probe comprises a nuclease.

15. The method of claim 14, wherein the nuclease comprises an RNase, optionally wherein the RNase is selected from RNase A, RNase C, RNase H, or RNase I.

16. The method of claim 13, wherein the permeabilization agent comprises a protease.

17. The method of claim 16, wherein the protease is selected from trypsin, pepsin, elastase, or proteinase K.

18. The method of claim 1, further comprising determining (i) all or a part of the sequence of the connected probe, or a complement thereof, and (ii) the spatial barcode, or a complement thereof, and using the determined sequence of (i) and (ii) to determine a location of the nucleic acid analyte in the biological sample.

19. The method of claim 18, wherein the determining comprises sequencing (i) all or a part of the sequence of the connected probe, or a complement thereof, and (ii) the sequence of the spatial barcode, or a complement thereof.

20. The method of claim 1, wherein the capture probe comprises a poly(T) sequence, one or more functional domains, a unique molecular identifier (UMI), a cleavage domain, or combinations thereof.

21. The method of claim 1, wherein the nucleic acid analyte is RNA.

22. The method of claim 21, wherein the RNA is mRNA.

23. The method of claim 1, further comprising processing a different type of analyte in the biological sample.

24. The method of claim 23, wherein the processing the different type of analyte comprises:
before (c), contacting the biological sample with a plurality of analyte capture agents, wherein an analyte capture agent of the plurality of analyte capture agents comprises an analyte binding moiety and a capture agent barcode domain, wherein the analyte binding moiety specifically binds to the different type of analyte, and wherein the capture agent barcode domain comprises an analyte binding moiety barcode and a capture handle sequence; and hybridizing the capture handle sequence to the capture domain of the capture probe on the array.

25. The method of claim 24, further comprising determining (i) all or part of the sequence of the capture agent barcode domain; and (ii) the spatial barcode, or a complement thereof, and using the determined sequence of (i) and (ii) to analyze the different type of analyte in the biological sample.

26. The method of claim 24, further comprising a releasing step, wherein the capture agent barcode domain is released from the different type of analyte.

27. The method of claim 24, wherein the different type of analyte is a protein analyte.

28. The method of claim 1, wherein the biological sample is a tissue sample.

29. The method of claim 1, wherein the biological sample is a formalin fixed paraffin embedded (FFPE) tissue sample.

30. The method of claim 29, wherein the tissue sample is fixed and stained prior to step (a).

\* \* \* \* \*